(12) United States Patent
Nutzman et al.

(10) Patent No.: US 6,321,114 B1
(45) Date of Patent: Nov. 20, 2001

(54) IMPLANTABLE MEDICAL DEVICE HAVING FLAT ELECTROLYTIC CAPACITOR WITH CONSOLIDATED ELECTRODE TABS AND CORRESPONDING FEEDTHROUGHS

(75) Inventors: Thomas M. Nutzman, Andover; Mark D. Breyen, Plymouth; William L. Johnson, Vadnais Heights; Joseph F. Lessar, Coon Rapids; Anthony R. Rorvick, Brooklyn Park; Kurt J. Casby, Eagan, all of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/359,183

(22) Filed: Jul. 22, 1999

Related U.S. Application Data

(62) Division of application No. 09/103,876, filed on Jun. 24, 1998.
(60) Provisional application No. 60/080,564, filed on Apr. 3, 1998.

(51) Int. Cl.[7] ................................................. A61N 1/362
(52) U.S. Cl. ............................................................ 607/5
(58) Field of Search ................................ 607/4, 5, 6, 7, 607/8, 9

(56) References Cited

U.S. PATENT DOCUMENTS

| | | |
|---|---|---|
| 3,398,333 | 8/1968 | Zeppieri . |
| 3,789,502 | 2/1974 | Callins et al. ........................ 29/570 |
| 4,041,956 | 8/1977 | Purdy et al. ........................ 128/419 P |
| 4,183,600 | 1/1980 | Schroeder ........................ 339/218 R |
| 4,385,342 | 5/1983 | Puppolo et al. ........................ 361/433 |
| 4,521,830 | 6/1985 | Aultman et al. ........................ 361/433 |
| 4,546,415 | 10/1985 | Kent et al. ........................ 361/433 |
| 4,663,824 | 5/1987 | Kenmochi ........................ 29/570 |
| 4,692,147 | 9/1987 | Duggan ........................ 604/93 |
| 4,942,501 | 7/1990 | MacFarlane et al. ........................ 361/523 |
| 4,987,519 | 1/1991 | Hutchins et al. ........................ 361/518 |
| 5,086,374 | 2/1992 | MacFarlane et al. ........................ 361/525 |
| 5,131,388 | 7/1992 | Pless et al. ........................ 128/419 D |
| 5,146,391 | 9/1992 | MacFarlane et al. ........................ 361/525 |
| 5,153,820 | 10/1992 | MacFarlane et al. ........................ 361/525 |
| 5,324,910 | 6/1994 | Isawa ........................ 219/118 |
| 5,370,663 | 12/1994 | Lin ........................ 607/5 |
| 5,380,341 | 1/1995 | Matthews et al. ........................ 29/25.03 |
| 5,456,698 | 10/1995 | Byland et al. ........................ 607/36 |
| 5,522,851 | 6/1996 | Fayram ........................ 607/5 |
| 5,545,184 | 8/1996 | Dougherty ........................ 607/5 |
| 5,584,890 | 12/1996 | MacFarlane et al. ........................ 29/25.03 |
| 5,628,801 | 5/1997 | MacFarlane et al. ........................ 29/25 |
| 5,660,737 | 8/1997 | Elias et al. ........................ 216/6 |

*Primary Examiner*—Scott M. Getzow
(74) *Attorney, Agent, or Firm*—Thomas F. Woods; Harold R. Patton; Girma Wolde-Michael

(57) ABSTRACT

An implantable medical device such as a defibrillator is described. The device includes an hermetically sealed housing containing a flat electrolytic capacitor and an energy source such as a battery. The battery is connected to the capacitor and provides charge thereto. The capacitor stores the charge at a relatively high voltage. The charge stored in the capacitor is discharged through a defibrillation lead to a site on or in the heart when fibrillation of the heart is detected by the implantable medical device. Methods of making and using the implantable medical device, the capacitor, and their various components are disclosed.

43 Claims, 31 Drawing Sheets

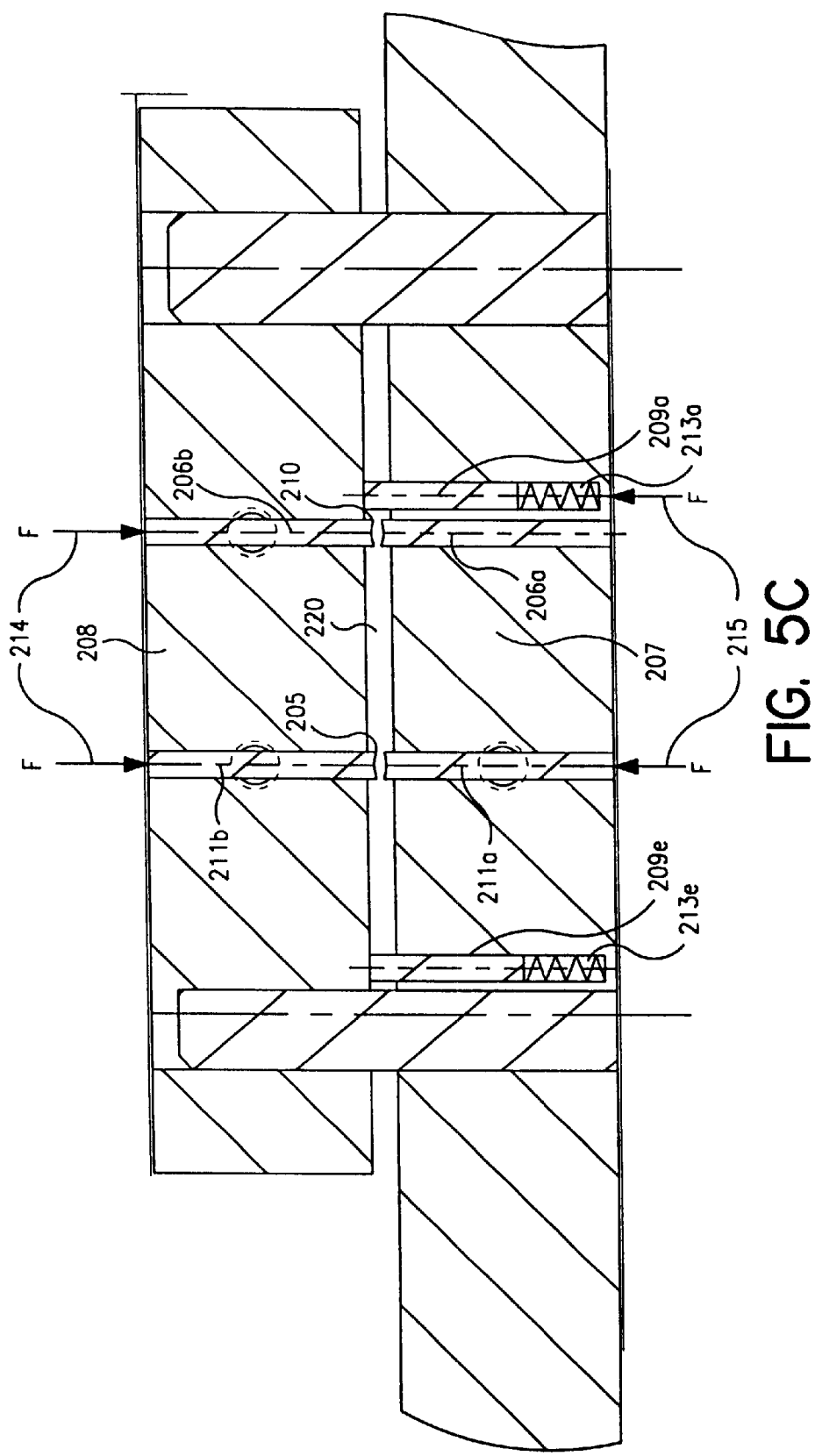

ized cardioverter, such as that described in "Clinical Application of Cardioversion" in *Cardiovascular Clinics*, 1970, Vol. 2, pp. 239–260 by Douglas P. Zipes. This type of external device provides cardioversion shocks synchronized with ventricular depolarization to ensure that the cardioverting energy is not delivered during the vulnerable T-wave portion of the cardiac cycle.

IMPLANTABLE MEDICAL DEVICE HAVING FLAT ELECTROLYTIC CAPACITOR WITH CONSOLIDATED ELECTRODE TABS AND CORRESPONDING FEEDTHROUGHS

RELATED APPLICATION

This application is a divisional application of U.S. patent application Ser. No. 09/103,876 filed Jun. 24, 1998 entitled "Implantable Medical Device Having Flat Capacitor With Consolidated Electrode Tabs and Corresponding Feedthroughs" to Nutzman et al.

This application claims priority and other benefits from U.S. Provisional patent application Ser. No. 60/080,564 filed Apr. 3, 1998 entitled "Flat Aluminum Electrolytic Capacitor."

FIELD OF THE INVENTION

This invention relates to implantable medical devices such as defibrillators and AIDs, and their various components, including flat electrolytic capacitors for same, and corresponding methods of making and using same.

BACKGROUND OF THE INVENTION

Implantable medical devices for therapeutic stimulation of the heart are well known in the art. In U.S. Pat. No. 4,253,466 issued to Hartlaub et al., for example, a programmable demand pacemaker is disclosed. The demand pacemaker delivers electrical energy, typically ranging in magnitude between about 5 and about 25 micro Joules, to the heart to initiate the depolarization of cardiac tissue. This stimulating regime is used to treat heart block by providing electrical stimulation in the absence of naturally occurring spontaneous cardiac depolarizations.

Another form of implantable medical device for therapeutic stimulation of the heart is an automatic implantable defibrillator (AID), such as those described in U.S. Pat. No. Re. 27,757 to Mirowski et al. and U.S. Pat. No. 4,030,509 to Heilman et al. Those AID devices deliver energy (about 40 Joules) to the heart to interrupt ventricular fibrillation of the heart. In operation, an AID device detects the ventricular fibrillation and delivers a nonsynchronous high-voltage pulse to the heart through widely spaced electrodes located outside of the heart, thus mimicking transthoracic defibrillation. The technique of Heilman et al. requires both a limited thoracotomy to implant an electrode near the apex of the heart and a pervenous electrode system located in the superior vena cava of the heart.

Another example of a prior art implantable cardioverter includes the pacemaker/cardioverter/defibrillator (PCD) disclosed in U.S. Pat. No. 4,375,817 to Engle et al. This device detects the onset of tachyarrhythmia and includes means to monitor or detect the progression of the tachyarrhythmia so that progressively greater energy levels may be applied to the heart to interrupt a ventricular tachycardia or fibrillation.

Another device is an external synchronized cardioverter, such as that described in "Clinical Application of Cardioversion" in *Cardiovascular Clinics*, 1970, Vol. 2, pp. 239–260 by Douglas P. Zipes. This type of external device provides cardioversion shocks synchronized with ventricular depolarization to ensure that the cardioverting energy is not delivered during the vulnerable T-wave portion of the cardiac cycle.

Another example of a prior art implantable cardioverter includes the device disclosed in U.S. Pat. No. 4,384,585 to Douglas P. Zipes. This device includes circuitry to detect the intrinsic depolarizations of cardiac tissue and pulse generator circuitry to deliver moderate energy level stimuli (in the range of about 0.1 to about 10 Joules) to the heart synchronously with the detected cardiac activity.

The functional objective of such a stimulating regimen is to depolarize areas of the myocardium involved in the genesis and maintenance of re-entrant or automatic tachyarrhythmias at lower energy levels with greater safety than was possible with nonsynchronous cardioversion. Nonsynchronous cardioversion always incurs the risk of precipitating ventricular fibrillation and sudden death. Synchronous cardioversion delivers the shock at a time when the bulk of cardiac tissue is already depolarized and is in a refractory state. Other examples of automatic implantable synchronous cardioverters include those of Charms in U.S. Pat. No. 3,738,370.

It is expected that the increased safety deriving from use of lower energy levels and their attendant reduced trauma to the myocardium, as well as the smaller size of implantable medical devices, will expand indications for use beyond the existing patient base of automatic implantable defibrillators. Since many episodes of ventricular fibrillation are preceded by ventricular (and in some cases, supraventricular) tachycardias, prompt termination of the tachycardia may prevent ventricular fibrillation.

Consequently, current devices for the treatment of tachyarrhythmias include the possibility of programming staged therapies of antitachycardia pacing regimens, along with cardioversion energy and defibrillation energy shock regimens in order to terminate the arrhythmia with the most energy-efficient and least traumatic therapies, when possible. In addition, some current implantable tachycardia devices are capable of delivering single or dual chamber bradycardia pacing therapies, as of which are described, for example, in U.S. Pat. No. 4,800,833 to Winstrom, U.S. Pat. No. 4,830,006 to Haluska et al., and U.S. patent application Ser. No. 07/612,758 to Keimel for "Apparatus for Delivering Single and Multiple Cardioversion and Defibrillation Pulses" filed Nov. 14, 1990, and incorporated herein by reference in its entirety. Furthermore, and as described in the foregoing '833 and '006 patents and the '758 application, considerable study has been undertaken to devise the most efficient electrode systems and shock therapies.

Initially, implantable cardioverters and defibrillators were envisioned as operating with a single pair of electrodes applied on or in the heart. Examples of such systems are disclosed in the aforementioned '757 and '509 patents, wherein shocks are delivered between an electrode is placed in or on the right ventricle and a second electrode placed outside the right ventricle. Studies have indicated that two electrode defibrillation systems often require undesirably high energy levels to effect defibrillation.

In an effort to reduce the amount of energy required to effect defibrillation, numerous suggestions have been made with regard to multiple electrode systems. Some of those suggestions are set forth in U.S. Pat. No. 4,291,699 to Geddes et al., U.S. Pat. No. 4,708,145 to Tacker et al., U.S. Pat. No. 4,727,877 to Kallock, and U.S. Pat. No. 4,932,407 issued to Williams where sequential pulse multiple electrode systems are described. Sequential pulse systems operate based on the assumption that sequential defibrillation pulses delivered between differing electrode pairs have an additive effect such that the overall energy requirements to achieve defibrillation are less than the energy levels required to accomplish defibrillation using a single pair of electrodes.

An alternative approach to multiple electrode sequential pulse defibrillation is disclosed in U.S. Pat. No. 4,641,656 to Smits and also in the above-cited '407 patent. This defibrillation method may conveniently be referred to as a multiple electrode simultaneous pulse defibrillation method, and involves the simultaneous delivery of defibrillation pulses between two different pairs of electrodes. For example, one electrode pair may include a right ventricular electrode and a coronary sinus electrode, and a second electrode pair may include a right ventricular electrode and a subcutaneous patch electrode, with the right ventricular electrode serving as a common electrode to both electrode pairs. An alternative multiple electrode, single path, biphasic pulse system is disclosed in U.S. Pat. No. 4,953,551 to Mehra et al., which employs right ventricular, superior vena cava and subcutaneous patch electrodes.

In the above-cited prior art simultaneous pulse multiple electrode systems, delivery of simultaneous defibrillation pulses is accomplished by simply coupling two electrodes together. For example, in the above-cited '551 patent, the superior vena cava and subcutaneous patch electrodes are electrically coupled together and a pulse is delivered between those two electrodes and the right ventricular electrode. Similarly, in the above-cited '407 patent, the subcutaneous patch and coronary sinus electrodes are electrically coupled together, and a pulse is delivered between these two electrodes and a right ventricular electrode. See also U.S. Pat. Nos. 5,411,539; 5,620,477; 5,6589,321; 5,545,189 and 5,578,062, where active can electrodes are discussed.

The aforementioned '758 application discloses a pulse generator for use in conjunction with an implantable cardioverter/defibrillator which is capable of providing all three of the defibrillation pulse methods described above, with a minimum of control and switching circuitry. The output stage is provided with two separate output capacitors which are sequentially discharged during sequential pulse defibrillation and simultaneously discharged during single or simultaneous pulse defibrillation. The complexity of those stimulation therapy regimens require rapid and efficient charging of high voltage output capacitors from low voltage battery power sources incorporated within the implantable medical device.

Typically, the electrical energy required to power an implantable cardiac pacemaker is supplied by a low voltage, low current drain, long-lived power source such as a lithium iodine pacemaker battery of the type manufactured by Wilson Greatbatch, Ltd. or Medtronic, Inc. While the energy density of such power sources is typically relatively high, they are generally not capable of being rapidly and repeatedly discharged at high current drains in the manner required to directly cardiovert the heart with cardioversion energies in the range of 0.1 to 10 Joules. Moreover, the nominal voltage at which such batteries operate is generally too low for cardioversion applications. Higher energy density battery systems are known which can be more rapidly or more often discharged, such as lithium thionyl chloride power sources. Neither of the foregoing battery types, however, may have the capacity or the voltage required to provide an impulse of the required magnitude on a repeatable basis to the heart following the onset of tachyarrhythmia.

Generally speaking, it is necessary to employ a DC-DC converter to convert electrical energy from a low voltage, low current power supply to a high voltage energy level stored in a high energy storage capacitor. A typical form of DC-DC converter is commonly referred to as a "flyback" converter which employs a transformer having a primary winding in series with the primary power supply and a secondary winding in series with the high energy capacitor. An interrupting circuit or switch is placed in series with the primary coil and battery. Charging of the high energy capacitor is accomplished by inducing a voltage in the primary winding of the transformer creating a magnetic field in the secondary winding. When the current in the primary winding is interrupted, the collapsing field develops a current in the secondary winding which is applied to the high energy capacitor to charge it. The repeated interruption of the supply current charges the high energy capacitor to a desired level over time.

In U.S. Pat. No. 4,548,209 to Wielders et al. and in the above-referenced '883 patent, charging circuits are disclosed which employ flyback oscillator voltage converters which step up the power source voltage and apply charging current to output capacitors until the capacitor voltage reaches a programmed shock energy level.

In charging circuit 34 of FIG. 4 in the '209 patent, two series-connected lithium thionyl chloride batteries 50 and 52 are connected to primary coil 54 of transformer 56 and to power FET transistor switch 60. Secondary coil 58 is connected through diode 62 to cardioversion energy storage capacitor 64. In this circuit, the flyback converter works generally as follows: When switch 60 is closed, current $I_p$ passing through primary winding 54 increases linearly as a function of the formula $V_p=L_p dI/dt$. When FET 60 is opened, the flux in the core of transformer 56 cannot change instantaneously, and so complimentary current $I_s$ (which is proportional to the number of windings in primary and secondary coils 54 and 58, respectively) starts to flow in secondary winding 58 according to the formula $I_s=(N_p/N_s)I_p$. Simultaneously, voltage in the secondary winding is developed according to the function $V_s=L_s dI_s/dt$, thereby causing charging of cardioversion energy storage capacitor 64 to a programmed voltage.

The Power FET 60 is switched "on" at a constant frequency of 32 KHz for a duration or duty cycle that varies as a function of the voltage of the output capacitor reflected back into the primary coil 54 circuit. The on-time of power FET 60 is governed by the time interval between the setting and resetting of flip-flop 70, which in turn is governed either by current $1_p$ flowing through primary winding 54 or as a function of a time limit circuit containing further circuitry to vary the time limit with battery impedance (represented schematically by resistor 53). In both cases, the on-time varies from a maximum to a minimum interval as the output circuit voltage increases to its maximum value.

The aforementioned '883 and '006 patents disclose a variable duty cycle flyback oscillator voltage converter, where the current in the primary coil circuit (in the case of the '883 patent) or the voltage across a secondary coil (in the case of the '006 patent) is monitored to control the duty cycle of the oscillator. In the '883 circuit the "on" time of the oscillator is constant and the "off" time varies as a function of the monitored current through the transformer.

In the '006 patent, a secondary coil is added to power a high voltage regulator circuit that provides V+ to a timer circuit and components of the high voltage oscillator. This high voltage power source allows the oscillator circuit to operate independently of the battery source voltage (which may deplete over time). The inclusion of a further secondary winding on an already relatively bulky transformer is disadvantageous from size and efficiency standpoints.

Energy, volume, thickness and mass are critical features in the design of implantable cardiac defibrillators (ICDs). One of the components important to optimization of those features is the high voltage capacitors used to store the energy required for defibrillation. Such capacitors typically deliver energy in the range of about 25 to 40 Joules, while ICDs typically have a volume of about 40 to about 60 cc, a thickness of about 13 mm to about 16 mm and a mass of approximately 100 grams.

It is desirable to reduce the volume, thickness and mass of such capacitors and devices without reducing deliverable energy. Doing so is beneficial to patient comfort and minimizes complications due to erosion of tissue around the device. Reductions in size of the capacitors may also allow for the balanced addition of volume to the battery, thereby increasing longevity of the device, or balanced addition of new components, thereby adding functionality to the device. It is also desirable to provide such devices at low cost while retaining the highest level of performance.

Most ICDs employ commercial photoflash capacitors similar to those described by Troup in "Implantable Cardioverters and Defibrillators," Current Problems in Cardiology, Volume XIV, Number 12, December 1989, Year Book Medical Publishers, Chicago, and U.S. Pat. No. 4,254,775 for "Implantable Defibrillator and Package Therefor". The electrodes in such capacitors are typically spirally wound to form a coiled electrode assembly. Most commercial photoflash capacitors contain a core of separator paper intended to prevent brittle anode foils from fracturing during coiling. The anode, cathode and separator are typically wound around such a paper core. The core limits both the thinness and volume of the ICDs in which they are placed. The cylindrical shape of commercial photoflash capacitors also limits the volumetric packaging efficiency and thickness of an ICD made using same.

As noted above, electrodes and separators used in the assembly of photoflash capacitors are typically coiled, with a resulting cylindrical capacitor geometry. Anodes employed in photoflash capacitors typically comprise one or two layers of a high purity (99.99%), porous, highly etched, anodized aluminum foil. Cathode layers in such capacitors are formed of a nonporous, highly etched aluminum foil which may be somewhat less pure (99.7%) respecting aluminum content than the anode layers. The thickness of such foils is on the order of 100 micrometers and 20 micrometers for anode foils and cathode foils, respectively. The capacitance of the cathode is balanced respecting that of the anode to ensure reliable performance over the life of the device. Separating the anode and cathode is a separator material that typically comprises two layers of Kraft paper.

Prior art electrolytic capacitors generally include a laminate comprising an etched aluminum foil anode, an aluminum foil of film cathode and a Kraft paper or fabric gauze spacer impregnated with a solvent based liquid electrolyte interposed therebetween. A layer of oxide is formed on the aluminum anode, preferably during passage of electrical current through the anode. The oxide layer functions as a dielectric layer. The entire laminate is rolled up into the form of a substantially cylindrical body and encased, with the aid of suitable insulation, in an aluminum tube or can subsequently sealed with a rubber material.

The energy of the capacitor is stored in the electromagnetic field generated by opposing electrical charges separated by an aluminum oxide layer disposed on the surface of the anode. The energy so stored is proportional to the surface area of the aluminum anode. Thus, to minimize the overall volume of the capacitor one must maximize anode surface area per unit volume without increasing the capacitor's overall (i.e., external) dimensions. Separator material, anode and cathode terminals, internal packaging and alignment features and cathode material further increase the thickness and volume of a capacitor. Consequently, those and other components in a capacitor limit the extent to which its physical dimensions may be reduced.

Recently developed flat aluminum electrolytic capacitors have overcome some disadvantages inherent in commercial cylindrical capacitors. For example, U.S. Pat. No. 5,131,388 to Pless et. al. discloses a relatively volumetrically efficient flat capacitor having a plurality of planar layers arranged in a stack. Each layer contains an anode layer, a cathode layer and means for separating the anode layers and cathode layers (such as paper). The anode layers and the cathode layers are electrically connected in parallel.

In a recent paper "High Energy Density Capacitors for Implantable Defibrillators" presented at CARTS 96: 16th Capacitor and Resistor Technology Symposium, Mar. 11–15, 1996, several improvements in the design of flat aluminum electrolytic capacitors are described. Described are the use of a solid adhesive electrolyte for strengthening the separator and allowing use of a thinner separator. Also described are a triple anode formed from a non-porous foil disposed between two porous foils. By increasing the number of anode foils per anode layer, the total number of separator and cathode layers in a given stack assembly is reduced, thereby decreasing thickness and volume. Next described are an embedded anode layer tab, where a notch is cut in the anode and a tab of the same thickness as the center anode is placed in the notch. Three anode layers are welded to one another and to the tabs by a cold welding process. See also U.S. Pat. Nos. 5,562,801; 5,153,820; 5,146,391; 5,086,374; 4,942,501; 5,628,801 and 5,584,890 to MacFarlane et al.

In U.S. Pat. No. 5,522,851 to Fayram, manufacturing improvements in flat capacitors relating to the use of internal alignment elements are disclosed. Internal alignment elements are employed as a means for controlling the relative edge spacing of electrode layers and the housing. In the absence of such alignment elements, precision assembly by hand may be required, thereby increasing manufacturing costs. The housing size must also be increased to provide tolerance for alignment errors, resulting in a bulkier device. The '851 patent also describes the use of an electrically conductive housing for grounding some capacitor elements, such as the cathode terminal.

A segment of today's ICD market employs flat capacitors to overcome some of the packaging and volume disadvantages associated with cylindrical photoflash capacitors. Examples of such flat capacitors are described in the '388 patent to Pless et al. for "Implantable Cardiac Defibrillator with Improved Capacitors," and the '851 patent to Fayram for "Capacitor for an Implantable Cardiac Defibrillators" Additionally, flat capacitors are described in a paper entitled "High Energy Density Capacitors for Implantable Defibrillators" by P. Lunsmann and D. MacFarlane presented at the 16th Capacitor and Resistor Technology Symposium.

Anodes and cathodes of aluminum electrolytic capacitors generally have tabs extending beyond their perimeters to facilitate electrical connection in parallel. In U.S. Pat. No. 4,663,824 to Kenmochi, tab terminal connections for a wound capacitor are described as being laser welded to feedthrough terminals. Wound capacitors usually contain two or no tabs joined together by crimping or riveting. Termination of larger numbers of anode tabs is described in the '851 patent as being accomplished through laser welding of the free ends of the tabs, followed by welding of the tabs to an inner terminal. In the '851 patent, cathode tabs are connected by ultrasonic welding to a step in the capacitor housing.

In assembling a capacitor, it is necessary that the anode and cathode remain separated electrically to prevent short circuiting. It is also important that a minimum separation between the anode and cathode be maintained to prevent arcing between the anode and cathode, or between the anode and the case. In cylindrical capacitors, such spacing is typically maintained at the electrode edges or peripheries by providing separator overhang at the top and bottom of the anode and cathode winding. In addition, the anode and cathode are aligned precisely and coiled tightly to prevent movement of the anode, cathode and separator during subsequent processing and use. In flat capacitors, anode to cathode alignment is typically maintained through the use of internal alignment posts (as described, for example, in the '851 patent to Pless et al.) screws (see the '851 patent to Pless et al.) or by using an adhesive electrolyte (see the patents to MacFarlane, supra).

Sealing of capacitor housings is typically accomplished in a variety of ways. Aultman et al. in U.S. Pat. No. 4,521,830 describes a typical aluminum electrolytic capacitor construction employed from about 1960 to about 1985. Those typical constructions employed a plastic header with two molded-in threaded aluminum terminals of the type shown in Collins et al. in U.S. Pat. No. 3,789,502, where plastic is molded around the terminals. Zeppieri in U.S. Pat. No. 3,398,333 and Schroeder in U.S. Pat. No. 4,183,600 teach prior art capacitors in which an aluminum serrated shank terminal extends through a thermal plastic header. In both patents the aluminum terminal is resistance-heated to a temperature such that the length of the terminal is collapsed and the center diameter is increased to press the serrations into the melted plastic. Aultman teaches a header design employing a compression-fit set of terminals disposed in a polymer header.

Hutchins et al. in U.S. Pat. No. 4,987,519 describe a glass-to-metal seal terminal connection with a tantalum outer ring being laser welded into an aluminum case. Kenmochi in U.S. Pat. No. 4,663,824 describes the use of a resin casing that has been previously formed from epoxy, silicon resin, polyoxybenzylene, polyether etherkeytone, or polyether sulfone, and that has high heat resistance. The terminals perforate the walls by molding them into the casing.

Pless et al. in U.S. Pat. No. 5,131,388 describe the use of a polymer envelope for encasement of the stack and feedthroughs. A silicon adhesive is used to seal the envelope at the seams. The polymer-enveloped flat stack is then disposed within a stainless steel or Titanium case. Aluminum capacitor terminals are described as being crimped or welded to the feedthroughs. Fayram in U.S. Pat. No. 5,522, 851 does not specifically address the issue of feedthrough design. An anode post is described as being electrically insulated from the housing.

U.S. Pat. No. 4,041,956 to Purdy et al. for "Pacemakers of Low Weight and Method of Making Such Pacemakers"; U.S. Pat. No. 4,692,147 to Duggan for "Drug Administration Device"; and U.S. Pat. No. 5,456,698 to Byland et al. for "Pacemaker" disclose various means of hermetically sealing housings for implantable medical devices, including laser welding means.

Various types of flat and spirally-wound capacitors are known in the art, some examples of which may be found in the issued U.S. Patents listed in Table 1 below.

TABLE 1

Prior Art Patents

| U.S. Pat. No. | Title |
| --- | --- |
| 3,398,333 | Electrical Component End Seal |
| 3,789,502 | Fused Cathode Electrolytic Capacitors and Method of Making the Same |
| 4,183,600 | Electrolytic Capacitor Cover-Terminal Assembly |
| 4,385,342 | Flat Electrolytic Capacitor |
| 4,521,830 | Low Leakage Capacitor Header and Manufacturing Method Therefor |
| 4,546,415 | Heat Dissipation Aluminum Electrolytic Capacitor |
| 4,663,824 | Aluminum Electrolytic Capacitor and a Manufacturing Method Therefor |
| 4,942,501 | Solid Electrolyte Capacitors and Methods of Making the Same |
| 4,957,519 | Hermetically Sealed Aluminum Electrolytic Capacitor |
| 5,086,374 | Aprotic Electrolyte Capacitors and Methods of Making the Same |
| 5,131,388 | Implantable Cardiac Defibrillator with Improved Capacitors |
| 5,146,391 | Crossiinked Electrolyte Capacitors and Methods of Making the Same |
| 5,153,820 | Crosslinked Electrolyte Capacitors and Methods of Making the Same |
| 5,324,910 | Welding Method of Aluminum Foil |
| 5,370,663 | Implantable Cardio-Stimulator with Flat Capacitor |
| 5,380,341 | Solid State Electrochemical Capacitors and Their Preparation |
| 5,545,184 | Cardiac Defibrillator with High Energy Storage Antiferroelectric Capacitor |
| 5,522,851 | Capacitor for an Implantable Cardiac Defibrillator |
| 5,584,890 | Methods of Making Multiple Anode Capacitors |
| 5,628,801 | Electrolyte Capacitor and Method of Making the Same |
| 5,660,737 | Process for Making a Capacitor Foil with Enhanced Surface Area |

As those of ordinary skill in the art will appreciate readily upon reading the Summary of the Invention, Detailed Description of the Preferred Embodiments and Claims set forth below, at least some of the devices and methods disclosed in the patents of Table 1 and elsewhere herein may be modified advantageously in accordance with the teachings of the present invention.

SUMMARY OF THE INVENTION

The present invention has certain objects. That is, the present invention provides solutions to many problems existing in the prior art respecting flat electrolytic capacitors for implantable medical devices. Those problems generally include one or more of the following: (a) out-gassing or fluid leakage from capacitor cases, resulting in damage to electronic circuitry contained within implantable medical devices; (b) poor or insufficient recharging times in discharged capacitors; (c) insufficient or marginal overall capacitor capacities; (d) decreasing voltage or capacity of capacitors with age; (e) volumetrically inefficient electrode packaging in capacitors; (f) heavy capacitor weights; (g) large physical sizes and volumes of capacitors; (h) expensive manufacturing processes; (i) difficulty in registering capacitor electrode assembly elements, and (j) expensive and unreliable capacitor sealing methods and structures.

Some embodiments of the invention have certain features generally, including at least one of: (a) an implantable cardiac defibrillator comprising an energy source, a flat electrolytic capacitor and means coupled to the energy source for charging the capacitor; (b) a capacitor comprising a planar layered structure of anode layers, cathode layers and separator layers separating the anode layers from the cathode layers; (c) a plurality of anode sub-assemblies electrically connected in parallel, and a plurality of cathode layers electrically connected in parallel.; (d) a plurality of anode sub-assemblies and the plurality of cathode layers that are interleaved, separated by interposed separator layers and impregnated or covered with a solid or liquid electrolyte to form an electrode assembly; (e) an anode sub-assembly comprising at least two anode layers; (f) at least one anode layer in an anode sub-assembly having a registration tab extending from a perimeter thereof; (g) at least one cathode layer having a registration tab extending from a perimeter thereof; (h) registration tabs for connecting anode sub-assemblies or cathode layers in parallel electrically; (i) registration tabs for connecting anode sub-assemblies or cathode layers to feedthroughs; (j) anode and cathode layers comprising aluminum foil; (k) separator layers comprising paper; (k) an aluminum case having an open end for receiving an electrode assembly therewithin; and (l) a case crimpingly or weldingly sealed with a cover.

Particular aspects of the various methods and apparatus of the present invention have at least some of the objects, features and advantages described below.

A first apparatus and corresponding methods of the present invention provide at least some solutions to problems existing in prior art capacitors for AIDs, including prior art capacitors that: (a) are prone to electrical shorting between adjacent anode and cathode layers due to the presence of burrs along the edges of cut electrode layers; (b) are prone to electrical shorting between adjacent anode and cathode layers due to the generation of metal particulates during electrode layer cutting processes; and (c) are costly to manufacture due to the large number of components they contain and the relatively slow manufacturing techniques employed to construct them.

Some embodiments of the first apparatus and corresponding methods of the present invention have certain features, including at least one of: (a) very low clearance dies for cutting capacitor electrode foil materials to form electrode layers; (b) die punches having faces not parallel to the corresponding floor of a cutting die for cutting capacitor electrode foil materials to form electrode layers; (c) upward die punch motions to cut capacitor foil materials to form electrode layers; and (d) use of air, gas or vacuum systems to clear debris from cut electrode layers.

In respect of known flat electrolytic capacitors, the first apparatus and corresponding methods of the present invention provide advantages, including one or more of: (a) formed electrode layers having a minimum number and size of edge burrs; (b) electrode foil material cutting and electrode layer forming methods well suited for high speed manufacturing methods; (c) electrode foil material cutting and electrode layer forming methods resulting in reduced cutting debris; and (d) electrode foil material and electrode layer forming methods producing reduced amounts of cutting debris on the surfaces of the electrode layers.

A second apparatus and corresponding methods of the present invention provide at least some solutions to problems existing in prior art capacitors for AIDs, including capacitors that: (a) add extra, inert volume in the form of alignment elements disposed within the capacitor case for registering electrode layers and assemblies; (b) provide means for aligning electrode layers that are too imprecise to permit the amount of paper overhang in electrode layers to be reduced; (c) may not be manufactured using high speed manufacturing techniques; (d) include many piece parts and therefore increase manufacturing costs.

Some embodiments of the second apparatus and corresponding methods of the present invention have certain features, including at least one of: (a) tooling and corresponding methods for capturing and aligning electrode tabs and aligning electrode layers; (b) robotic assembly methods for constructing electrode assemblies; (c) a capacitor design that does not require the use of inactive or inert alignment elements disposed within the capacitor case.

In respect of known flat electrolytic capacitors, the second apparatus and corresponding methods of the present invention provide advantages, including one or more of: (a) a more volumetrically efficient mechanical design providing lower volume and higher energy density; (b) a mechanical design and method for constructing electrode assemblies that permits the use of high speed manufacturing techniques; (c) lower cost capacitors owing to increased manufacturing efficiencies; (d) simple electrode layer and assembly plate geometries, resulting in fewer piece parts and lower cost; and (e) a case having fewer points from which electrolyte may leak.

A third apparatus and corresponding methods of the present invention provide at least some solutions to problems existing in prior art capacitors for AIDs, including capacitors that: (a) have electrode assemblies having electrode and separator layers that must be mechanically secured together by relatively large volume, inert mechanical means; (b) have electrode assemblies prone to movement within the case of the capacitor; (c) have feedthrough connections that may be affected by movement of the electrode assembly within the case.

Some embodiments of the third apparatus and corresponding methods of the present invention have certain features, including at least one of: (a) an electrode assembly secured together by a low-volume electrode assembly wrap and corresponding adhesive strip; (b) an electrode assembly secured together by low-volume electrode assembly clamps, bands or wraps disposed about the periphery of the assembly; (c) an electrode assembly which expands and is secured against the interior portions of a capacitor can by electrolyte-swelled separator layers; and (d) separator layers which envelop or are disposed between electrode layers, the separator layers having perimeters and surface areas which exceed those of the electrode layers.

In respect of known flat electrolytic capacitors, the third apparatus and corresponding methods of the present invention provide advantages, including one or more of: (a) a capacitor having higher energy density owing to more electrode material of greater surface area being disposed therewithin; (b) electrode layers having no holes for registration disposed therethrough, and therefore having increased surface area; (c) a capacitor not having elaborate, volume-consuming mechanisms for retaining or securing the electrode assembly disposed therewithin, and (d) highly reliable feedthrough connections owing to the electrode assembly being tightly secured and retained within the case of the capacitor.

A fourth apparatus and corresponding methods of the present invention provide at least some solutions to problems existing in prior art capacitors for AIDs, including capacitors that: (a) contain anode or cathode tab terminal connections that are difficult to laser weld or otherwise connect or connect to; (b) have tab terminals prone to fracturing during manufacturing; (c) require a two step, and therefore more costly, method for connecting electrode tabs and for connecting feedthroughs thereto; and (d) require an excessive number of components for connecting electrode tab bundles to feedthroughs, thereby increasing cost and volume and decreasing volumetric efficiency.

Some embodiments of the fourth apparatus and corresponding methods of the present invention have certain features, including at least one of: (a) direct consolidation and connection of multiple electrode layer tabs to a single feedthrough or feedthrough attachment means; (b) direct consolidation and connection of multiple electrode layer tabs to a coiled distal end of a single feedthrough or feedthrough attachment means; (c) welded feedthrough and electrode tab connections using, for example, laser spot welds, seam welds, ultrasonic welds or resistance welds; (d) an intermediate component disposed between electrode tabs and a feedthrough for providing strain relief.

In respect of known flat electrolytic capacitors, the fourth apparatus and corresponding methods of the present invention provide advantages, including one or more of: (a) a one-step method for connecting electrode tabs and feedthroughs; (b) a minimum number of components for connecting electrode tabs to feedthroughs; (c) highly reliable feedthrough connections; and (d) lower component and manufacturing costs.

A fifth apparatus and corresponding methods of the present invention provide at least some solutions to problems existing in prior art capacitors for AIDs, including capacitors that: (a) are susceptible to damage of internal capacitor components resulting from laser beams entering the interior of the capacitor case when welding the cover to the case of the capacitor; (b) require means incorporated into the capacitor for aligning the cover to the case during sealing operations that add inert, unusable volume to the capacitor; (c) require separate means for clamping the case and cover together during welding of the case and cover, thereby increasing manufacturing cycle time and cost; (d) have aluminum cases and covers that are difficult to laser weld together in a cost-effective manner yet still produce an hermetic seal; and (e) do not incorporate into the capacitor means for performing leaktightness testing.

Some embodiments of the fifth apparatus and corresponding methods of the present invention have certain features, including at least one of: (a) self-alignment and self-engagement elements or structures disposed along the joint between the case and the cover and incorporated into the capacitor to facilitate holding the case and cover together during welding and sealing; (b) case and corresponding cover weld joint and crimp configurations that eliminate or reduce laser beam damage to electrode assemblies during welding; (c) an optimized set of welding parameters for joining and sealing the case and cover of a capacitor; (d) an electrolyte fill port that permits standard helium leaktightness testing of the integrity of the capacitor seal.

In respect of known flat electrolytic capacitors, the fifth apparatus and corresponding methods of the present invention provide advantages, including one or more of: (a) not being damaged internally by laser beams employed to weld the case to the cover; (b) having means for aligning and maintaining the positions of the case and cover during welding and sealing that add no volume to the capacitor and that require no additional steps during the welding process; (c) providing a relatively wide window of cost-effective laser welding parameters for hermetically welding the case to the cover; (d) a flat capacitor that may be checked for leaktightness using cost-effective standard helium leak rate test methods.

A sixth apparatus and corresponding methods of the present invention provide at least some solutions to problems existing in prior art capacitors for AIDs, including capacitors that: (a) have no means for making simple crimped connections to the device; (b) have no hermetic seals for feedthroughs; (c) have external terminal or feedthrough interconnections that are susceptible to breaking or fracturing when the capacitor is dropped or vibrated excessively during handling or shipping; (d) have no or limited means for providing cost-effective electrically isolated feedthroughs; (e) have no cost-effective means for connecting external devices or circuits to the terminals of the capacitor; (f) have no flexible strain-relieving means for connecting electrodes to feedthroughs, or feedthroughs to external devices or circuits; (g) are prone to loss of electrolyte; and (h) susceptible to degradation of electrical properties over time.

Some embodiments of the sixth apparatus and corresponding methods of the present invention have certain features, including at least one of: (a) a wire harness assembly having a distal end that permits a wide variety of connection configurations; (b) crimp or slide contacts for device level connections; (c) a connector module mounted on, attached to or engaging the external surface of a capacitor can or cover; (d) an epoxy- or adhesive-sealed feedthrough; (e) feedthrough ferrules and corresponding wire guides; (f) a capacitor case, cover, ferrules, feedthroughs and fill port providing a high degree of hermeticity; and (g) means for connecting capacitor feedthroughs to external devices or circuits that are located away from the case of the capacitor.

In respect of known flat electrolytic capacitors, the sixth apparatus and corresponding methods of the present invention provide advantages, including one or more of: (a) fewer manufacturing steps and related lower assembly costs when placing the capacitor within an implantable medical device; (b) crimp contact or sliding feedthrough contacts that are easy to connect at the device level; (c) no or little loss of electrolyte from the capacitor owing to its high degree of hermeticity; (d) a capacitor having electrical properties which do not degrade over the lifetime of the implantable medical device within which the capacitor is disposed; and (e) highly flexible means for accomplishing device level interconnection without major redesign of the capacitor terminal structure.

A seventh apparatus and corresponding methods of the present invention provide at least some solutions to problems existing in prior art capacitors for AIDs, including capacitors that: (a) contain means for cold welding electrode layers and tabs to electrode layers that add significant thickness to an electrode assembly, thereby increasing overall thickness of the capacitor and its corresponding implantable medical device; and (b) means for cold welding electrode layers that are not adaptable to high speed manufacturing techniques.

Some embodiments of the seventh apparatus and corresponding methods of the present invention have certain features, including at least one of: (a) means for restricting out-of-plane material flow in flat electrode layers during cold welding steps; (b) means for cold welding electrode layers to one another, and for cold welding separator layers to electrode layers, that are adaptable to high speed manufacturing methods; and (c) means for monitoring individual cold weld processing parameters.

In respect of known flat electrolytic capacitors, the seventh apparatus and corresponding methods of the present invention provide advantages, including one or more of: (a) low clearance cold welds in electrode and separator layers, thereby decreasing the thickness of the capacitor and corresponding implantable medical device; and (b) adaptability to high speed manufacturing techniques.

An eighth apparatus and corresponding methods of the present invention provide at least some solutions to problems existing in prior art capacitors for AIDs, including capacitors that: (a) have high equivalent series resistances; and (b) have relatively low total capacitances.

Some embodiments of the eighth apparatus and corresponding methods of the present invention have certain features, including at least one of: (a) a capacitor having relatively low equivalent series resistance; (b) a capacitor having relatively high total capacitance; and (c) a capacitor containing a liquid electrolyte that has undergone successive cycles of being subjected to a vacuum and no vacuum while the electrolyte is presented to the cell interior to thereby efficiently and relatively completely saturate the electrode layers of the capacitor.

In respect of known flat electrolytic capacitors, the eighth apparatus and corresponding methods of the present invention provide advantages, including one or more of: (a) a capacitor that is capable of delivering high amounts of charge and energy; (b) a capacitor that recharges quickly and efficiently; and (c) a capacitor having charge and discharge performance that does not appreciably degrade over the lifetime of its corresponding implantable medical device Those of ordinary skill in the art will understand immediately upon referring to the drawings, detailed description of the preferred embodiments and claims hereof that many objects, features and advantages of the capacitors and methods of the present invention will find application in the fields other than the field of implantable medical devices.

BRIEF DESCRIPTION OF THE DRAWINGS

Reference is now made to the accompanying detailed drawings of the preferred embodiments in which like reference numerals represent like or similar parts throughout, wherein:

FIG. 5(c) shows a cross-sectional view of the cold welding apparatus of FIGS. 5(a) and 5(b) in which anode layers of the electrode sub-assembly of FIG. 4 are cold-welded therein;

DETAILED DESCRIPTION OF THE PREFERRED EMBODIMENTS

Figure 1:
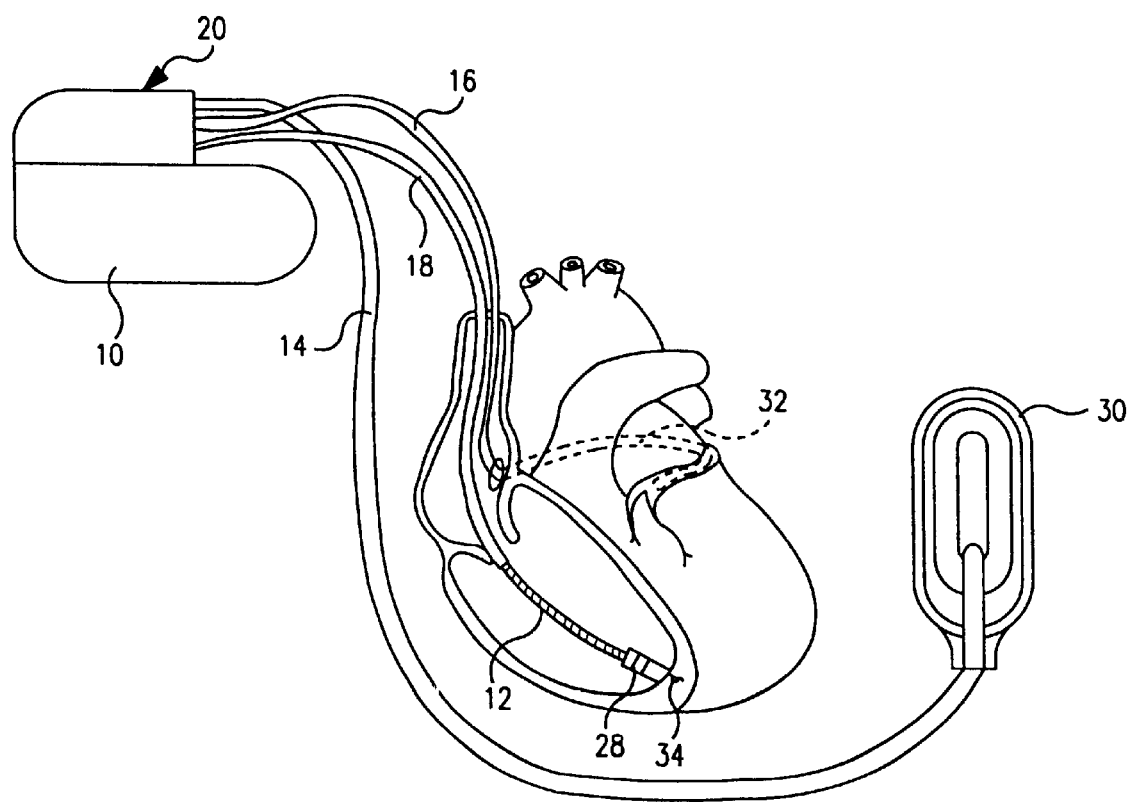
FIG. 1 illustrates the physical components of one embodiment of a pacemaker/cardioverter/defibrillator (PCD) and lead system of one embodiment of the present invention.

FIG. 1 illustrates one embodiment of implantable PCD 10 of the present invention, its associated electrical leads 14, 16 and 18, and their relationship to a human heart 12. The leads are coupled to PCD 10 by means of multi-port connector block 20, which contains separate connector ports for each of the three leads illustrated. Lead 14 is coupled to subcutaneous electrode 30, which is intended to be mounted subcutaneously in the region of the left chest. Lead 16 is a coronary sinus lead employing an elongated coil electrode which is located in the coronary sinus and great vein region of the heart. The location of the electrode is illustrated in broken line format at 32, and extends around the heart from a point within the opening of the coronary sinus to a point in the vicinity of the left atrial appendage.

Lead 18 is provided with elongated electrode coil 28 which is located in the right ventricle of the heart. Lead 18 also includes stimulation electrode 34 which takes the form of an advanceable helical coil which is screwed into the myocardial tissue of the right ventricle. Lead 18 may also include one or more additional electrodes for near and far field electrogram sensing. A more detailed description of the leads illustrated can be found in the aforementioned '407 patent. However, the invention is also believed workable in the context of multiple electrode systems employing different sets of electrodes, including superior vena cava electrodes and epicardial patch electrodes.

In the system illustrated, cardiac pacing pulses are delivered between helical electrode 34 and elongated electrode 28. Electrodes 28 and 34 are also employed to sense electrical signals indicative of ventricular contractions. As illustrated, it is anticipated that the right ventricular electrode 28 will serve as the common electrode during sequential and simultaneous pulse multiple electrode defibrillation regimens. For example, during a simultaneous pulse defibrillation regimen, pulses would simultaneously be delivered between electrode 28 and electrode 30 and between electrode 28 and electrode 32. During sequential pulse defibrillation, it is envisioned that pulses would be delivered sequentially between subcutaneous electrode 30 and electrode 28 and between coronary sinus electrode 32 and right ventricular electrode 28. Single pulse, two electrode defibrillation pulse regimens may be also provided, typically between electrode 28 and coronary sinus electrode 32. Alternatively, single pulses may be delivered between electrodes 28 and 30. The particular interconnection of the electrodes to an implantable PCD will depend somewhat on which specific single electrode pair defibrillation pulse regimen is believed more likely to be employed.

Figure 2:
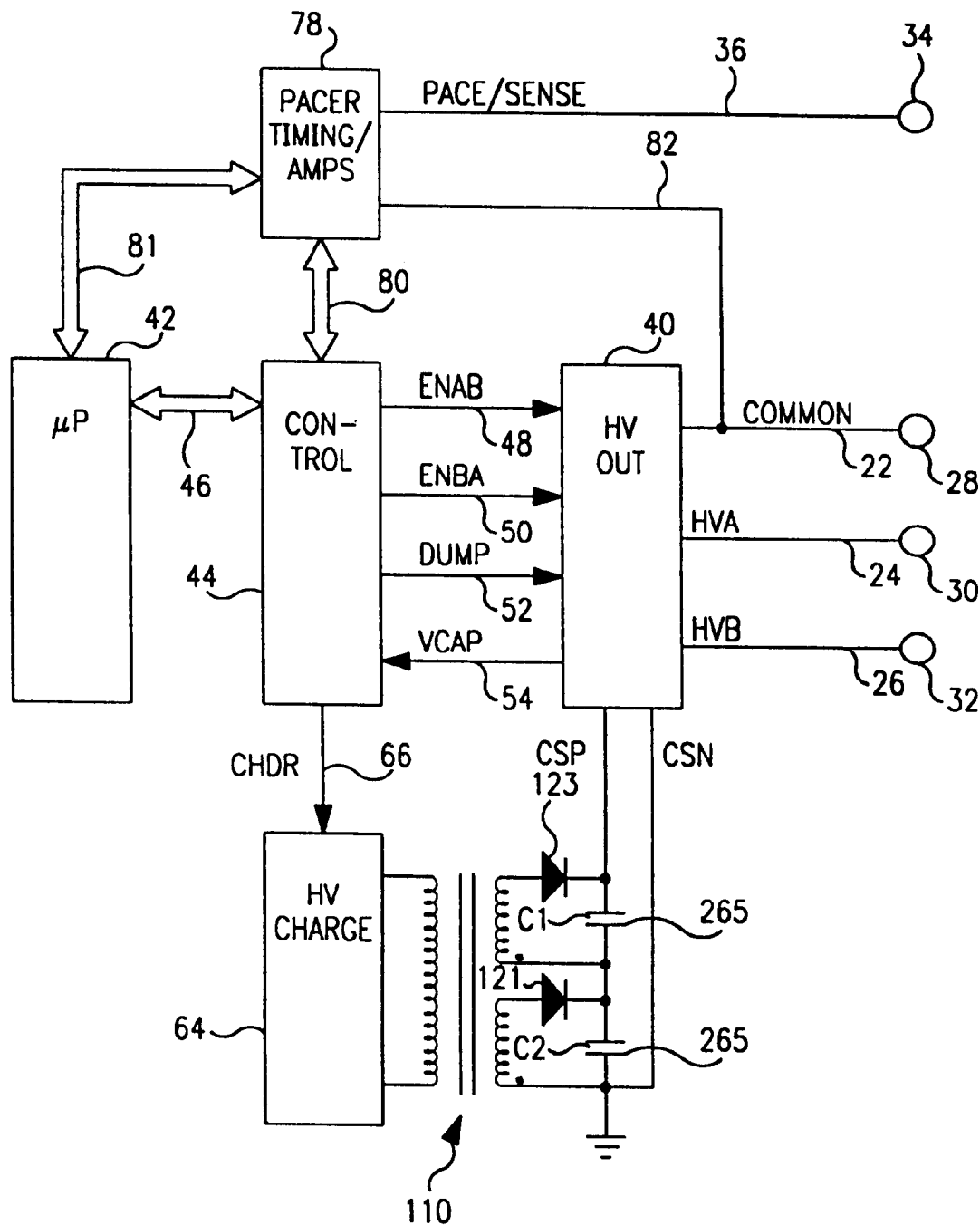
FIG. 2 shows a functional block diagram illustrating the interconnection of voltage conversion circuitry of one embodiment of the present invention with primary functional components of one type of an implantable PCD.

FIG. 2 is a block diagram illustrating the interconnection of high voltage output circuit 40, high voltage charging circuit 64 and capacitors 265 according to one embodiment of the present invention with a prior art implantable PCD. As illustrated, the device is controlled by means of a stored program in microprocessor 42, which performs all necessary computational functions within the device. Microprocessor 42 is linked to control circuitry 44 by means of bidirectional data/control bus 46, and thereby controls operation of the output circuitry 40 and the high voltage charging circuitry 64. On reprogramming of the device or on the occurrence of signals indicative of delivery of cardiac pacing pulses or of the occurrence of cardiac contractions, pace/sense circuitry 78 will awaken microprocessor 42 to perform any necessary mathematical calculations, to perform tachycardia and fibrillation detection procedures and to update the time intervals controlled by the timers in pace/sense circuitry 78.

The basic operation of such a system in the context of an implantable PCD may correspond to any of the systems known in the art. More particularly, the flat aluminum electrolytic capacitor of the present invention may be employed generally in conjunction with the various systems illustrated in the aforementioned '209, '585, '006, '883 and '817 patents, or in conjunction with the various systems or components disclosed in U.S. Pat. No. 4,693,253 to Adams, U.S. Pat. No. 5,188,105 to Keimel, U.S. Pat. No. 5,591,212 to Keimel, U.S. Pat. No. 5,383,909 to Keimel, U.S. Pat. No. 5,354,316 to Keimel, U.S. Pat. No. 5,336,253 to Gordon et al., U.S. Pat. No. 4,384,585 to Zipes, U.S. Pat. No. 4,949,719 to Pless et al., U.S. Pat. No. 4,374,817 to Engle et al., U.S. Pat. No. 4,577,633 to Berkowitz, U.S. Pat. No. 4,880,005 to Pless et al., U.S. Pat. No. 4,726,380 to Vollmann et al., U.S. Pat. No. 4,587,970 to Holley et al., U.S. Pat. No. 5,447,519 to Peterson, U.S. Pat. No. 4,476,868 to Thompson, U.S. Pat. No. 4,556,063 to Thompson, U.S. Pat. No. 4,379,459 to Stein, U.S. Pat. No. 5,312,453 to Wyborny, U.S. Pat. No. 5,545,186 to Olson, U.S. Pat. No. 5,345,316 to Keimel, U.S. Pat. No. 5,314,430 to Bardy, U.S. Pat. No. 5,131,388 to Pless, U.S. Pat. No. 3,888,260 to Fischell, U.S. Pat. No. 5,411,537 to Munshi et al. and U.S. Pat. No. 4,821,723 to Baker et al. All the foregoing patents are hereby incorporated herein by reference in their respective entireties.

Control circuitry 44 provides three signals of primary importance to output circuitry 40 of the present invention. Those signals include the first and second control signals discussed above, labeled here as ENAB, line 48, and ENBA, line 50. Also of importance is DUMP line 52 which initiates discharge of the output capacitors and VCAP line 54 which provides a signal indicative of the voltage stored on the output capacitors C1, C2, to control circuitry 44. Defibrillation electrodes 28, 30 and 32 illustrated in FIG. 1, above, are shown coupled to output circuitry 40 by means of conductors 22, 24 and 26. For ease of understanding, those conductors are also labeled as "COMMON", "HVA" and "HVB". However, other configurations are also possible. For example, subcutaneous electrode 30 may be coupled to HVB conductor 26, to allow for a single pulse regimen to be delivered between electrodes 28 and 30. During a logic signal on ENAB, line 48, a cardioversion/defibrillation pulse is delivered between electrode 30 and electrode 28. During a logic signal on ENBA, line 50, a cardioversion/ defibrillation pulse is delivered between electrode 32 and electrode 28.

The output circuitry of the present invention includes a capacitor bank, including capacitors C1 and C2 and diodes 121 and 123, used for delivering defibrillation pulses to the electrodes. Alternatively, the capacitor bank may include a further set of capacitors as depicted in the above referenced '758 application. In FIG. 2, capacitors 265 are illustrated in conjunction with high voltage charging circuitry 64, controlled by the control/timing circuitry 44 by means of CHDR line 66. As illustrated, capacitors 265 are charged by means of a high frequency, high voltage transformer 110. Proper charging polarities are maintained by means of the diodes 121 and 123. VCAP line 54 provides a signal indicative of the voltage on the capacitor bank, and allows for control of the high voltage charging circuitry and for termination of the charging function when the measured voltage equals the programmed charging level.

Pace/sense circuitry 78 includes an R-wave amplifier according to the prior art, or more advantageously as disclosed in co-pending, commonly assigned U.S. patent application. Ser. No. 07/612,670 to Keimel et al. for "Apparatus for Monitoring Electrical Physiological Signals," filed Nov. 14, 1990, which is hereby incorporated herein by reference in its entirety. The present invention is believed workable, however, in the context of any known R-wave amplification system. Pace/sense circuitry 78 also includes a pulse generator for generating cardiac pacing pulses, which may also correspond to any known cardiac pacemaker output circuitry and includes timing circuitry for defining ventricular pacing intervals, refractory intervals and blanking intervals, under control of microprocessor 42 via controvdata bus 80.

Control signals triggering generation of cardiac pacing pulses by pace/sense circuitry 78 and signals indicative of the occurrence of R-waves, from pace/sense circuitry 78 are communicated to control circuitry 44 by means of a bi-directional data bus 81. Pace/sense circuitry 78 is coupled to helical electrode 34 illustrated in FIG. 1 by means of a conductor 36. Pace/sense circuitry 78 is also coupled to ventricular electrode 28, illustrated in FIG. 1, by means of a conductor 82, allowing for bipolar sensing of R-waves between electrodes 34 and 28 and for delivery of bipolar pacing pulses between electrodes 34 and 28, as discussed above.

Figure 3A:
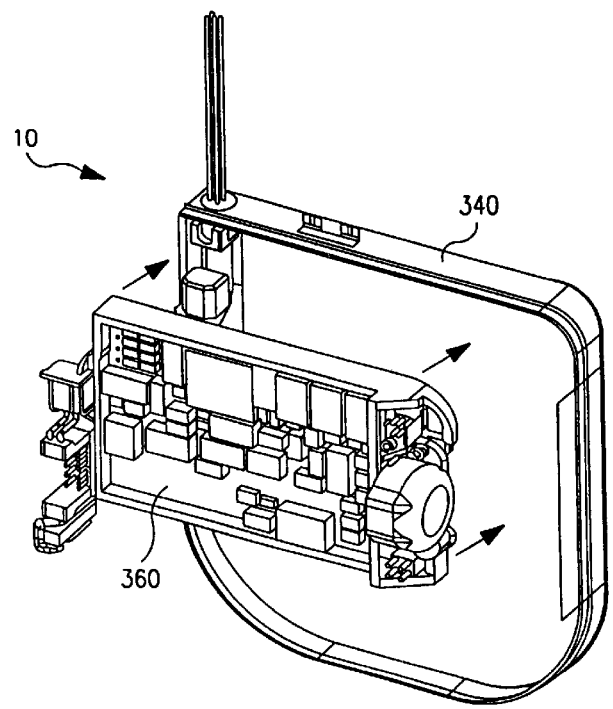
FIGS. 3A–3G are an exploded perspective views of the various components of one embodiment of the present invention as they are disposed within the housing of implantable PCD.
Figure 3B:
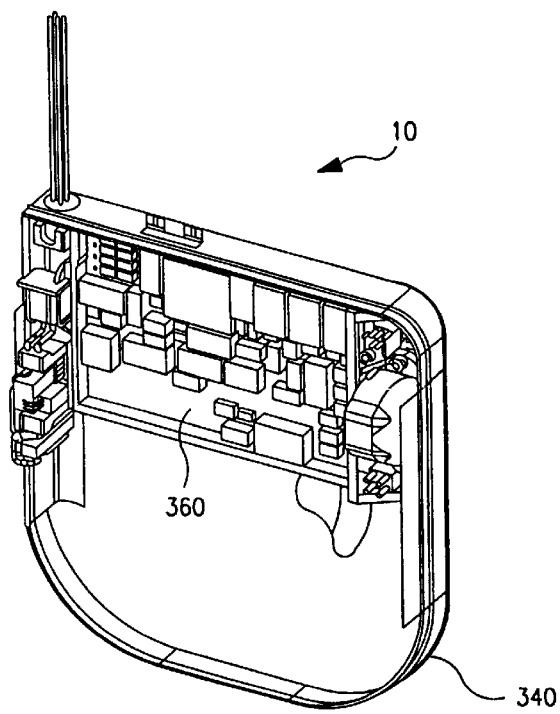

FIGS. 3(a) through 3(g) show perspective views of various components of implantable PCD 10 of the present invention, including one embodiment of the capacitor of the present invention, as those components are placed successively within the housing of PCD 10. In FIG. 3(a), electronics module 360 is placed in right-hand shield 340 of PCD 10. FIG. 3(b) shows PCD 10 once electronics module 360 has been seated in right-hand shield 340.

Figure 3C:
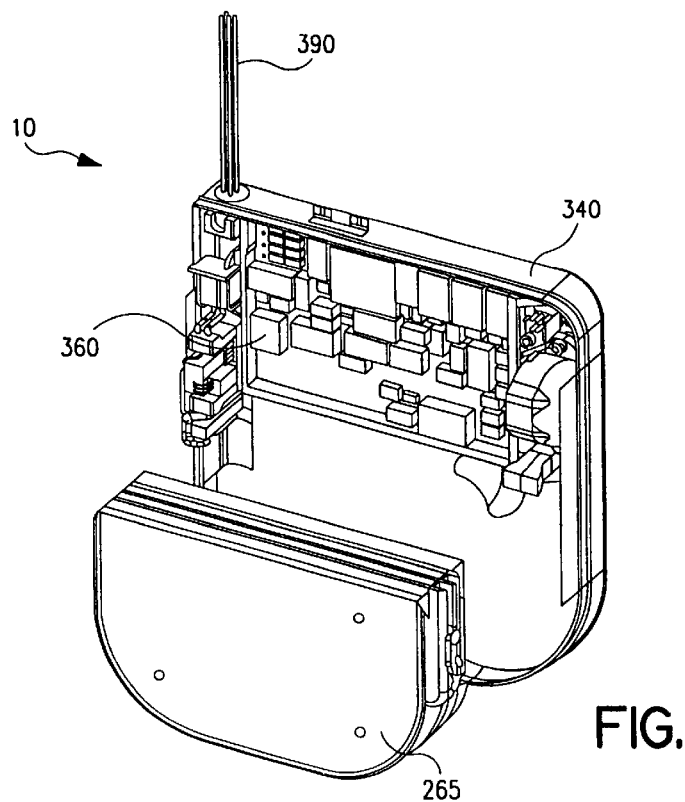
Figure 3D:
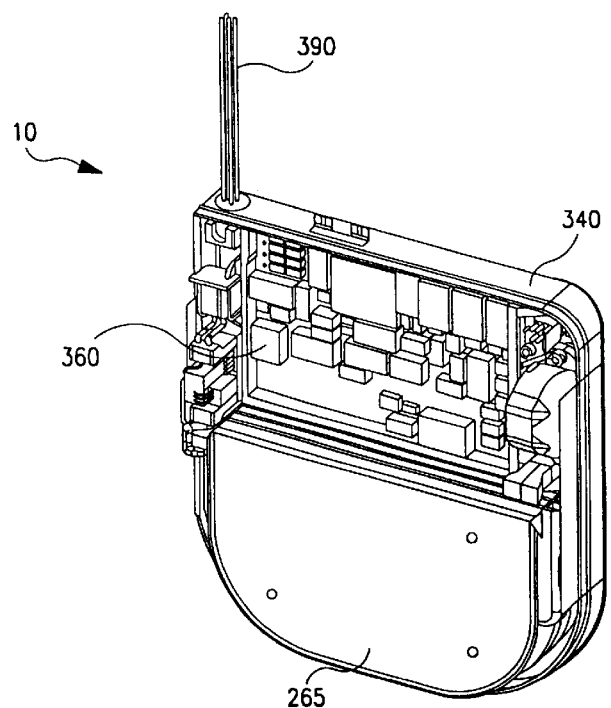

FIG. 3(c) shows a pair of capacitors 265 of the present invention prior to being placed within right-hand shield 340, the capacitors being connected electrically in series by interconnections in electronics module 340. FIG. 3(d) shows PCD 10 once the pair of capacitors 265 has been placed within right-hand shield 340.

Figure 3E:
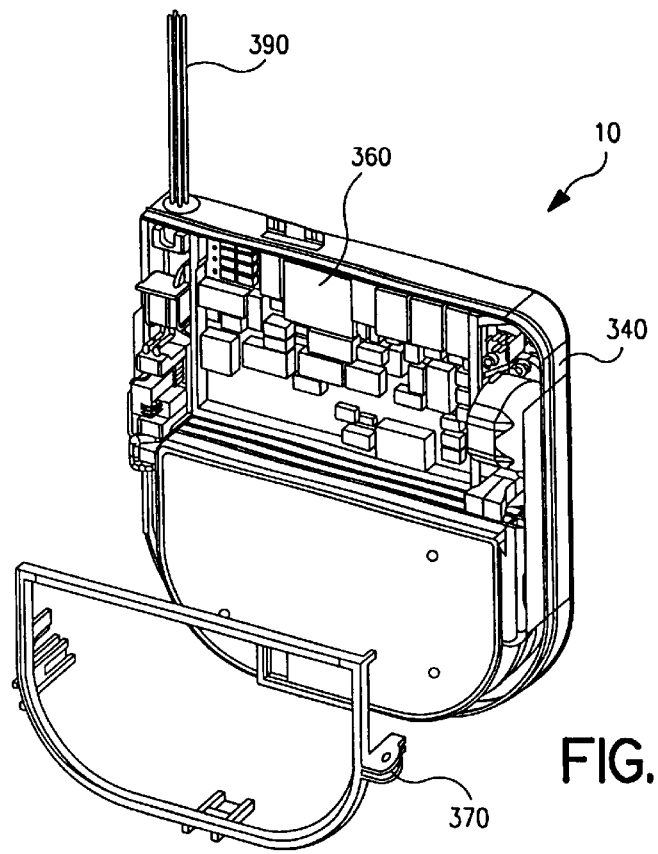
Figure 3F:
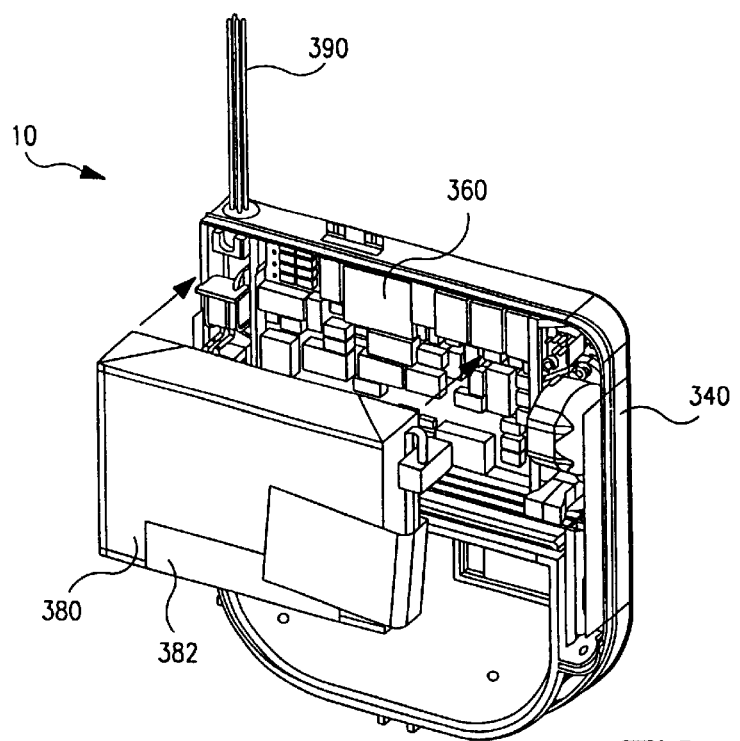
Figure 3G:
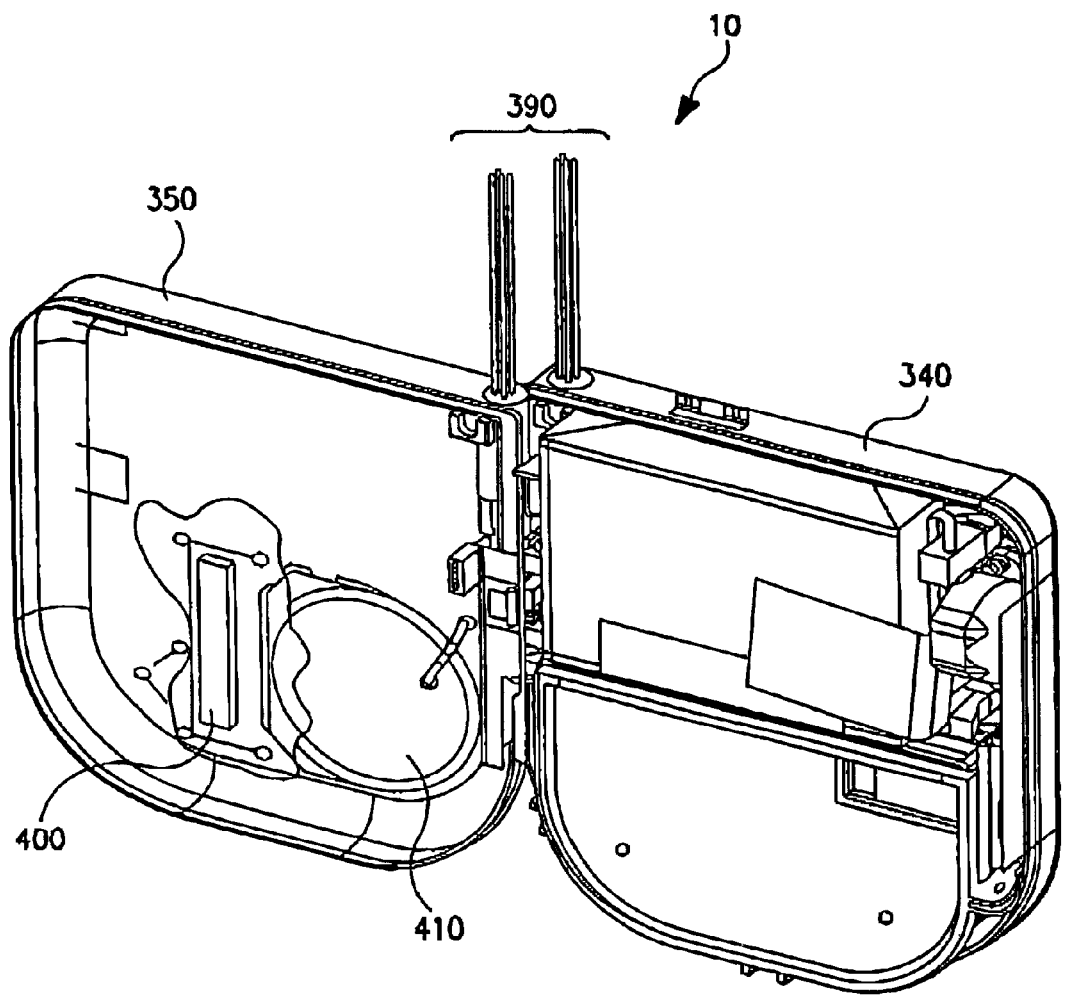

FIG. 3(e) shows insulator cup 370 prior to its placement atop capacitors 265 in right-hand shield 340. FIG. 3(f) shows electrochemical cell or battery 380 having insulator 382 disposed therearound prior to battery 380's placement in shield 340. Battery 380 provides the electrical energy required to charge and re-charge capacitors 265, and also powers electronics module 360.

Battery 380 is most preferably a high-capacity, high-rate, spirally-wound battery of the type disclosed in U.S. Pat. No. 5,439,760 to Howard et al. for "High Reliability Electrochemical Cell and Electrode Assembly Therefor" and U.S. Pat. No. 5,434,017 to Berkowitz et al. for "High Reliability Electrochemical Cell and Electrode Assembly Therefor," the disclosures of which are hereby incorporated by reference herein in their respective entireties.

Battery 380 may less preferably be a battery having spirally-wound, stacked plate or serpentine electrodes of the types disclosed, for example, in U.S. Pat. Nos. 5,312,458 and 5,250,373 to Muffoletto et al. for "Internal Electrode and Assembly Method for Electrochemical Cells;" U.S. Pat. No. 5,549,717 to Takeuchi et al. for "Method of making Prismatic Cell;" U.S. Pat. No. 4,964,877 to Kiester et al. for "Non-Aqueous Lithium Battery;" U.S. Pat. No. 5,147,737 to Post et al. for "Electrochemical Cell with Improved Efficiency Serpentine Electrode" and U.S. Pat. No. 5,468,569 to Pyszczek et al. for "Use of Standard Uniform Electrode Components in Cells of Either High or Low Surface Area Design," the disclosures of which are hereby incorporated by reference herein in their respective entireties.

High-rate hybrid cathode cells are particularly suitable for use in conjunction with the capacitor of the present invention. Examples of hybrid cathode batteries and cells having cathodes comprising lithium anodes and cathodes containing mixtures of various types of silver vanadium oxide and $(CF_x)_n$, are disclosed in U.S. Pat. No. 5,114,810 to Frysz et al.; U.S. Pat. No. 5,180,642 to Weiss et al.; U.S. Pat. No. 5,624,767 to Muffoletto et al.; U.S. Pat. No. 5,639,577 to Takeuchi et al., and U.S. Pat. No. 5,667,916 to Ebel et al., all of which patents are hereby incorporated by reference herein in their respective entireties.

In preferred embodiments of batteries suitable for use in conjunction with the capacitor of the present invention, it has been discovered that the electrolyte most preferably comprises about 1.0 M $LiBF_4$, the anode most preferably comprises lithium metal, the cathode most preferably comprises about 90% by weight active materials (i.e., 90% by weight of a mixture of $(CF_x)_n$ and SVO), about 7% by weight polymer binder and about 3% conductive carbon.

The SVO employed in cells and batteries employed to charge and recharge the capacitor of the present invention is most preferably of the type known as "combination silver vanadium oxide" or "CSVO" as disclosed in U.S. Pat. Nos. 5,221,453; 5,439,760 and 5,306,581 and U.S. patent application. Ser. No. 08/792,413 filed Feb. 3, 1997 to Crespi et al., hereby incorporated by reference herein, each in its respective entirety.

It is to be understood, however, that any type of suitable silver vanadium oxide (or SVO) may be employed in cathodes and cells used to charge and recharge capacitors of the present invention, including, but not limited to, substitute SVO as disclosed by Takeuchi et al. in U.S. Pat. No. 5,472,810 and as disclosed by Leising et al. in U.S. Pat. No. 5,695,892, SVO made by the decomposition method as disclosed by Liang et al. in U.S. Pat. Nos. 4,310,609 and 4,391,729, amorphous SVO as disclosed by Takeuchi et al. in U.S. Pat. No. 5,498,494, SVO prepared by the sol-gel method as disclosed by Takeuchi et al. in U.S. Pat. No. 5,558,680, and SVO prepared by the hydrothermal process.

Additionally, it is preferred that batteries used in conjunction with the capacitor of the present invention be cathode limited to permit accurate, reliable prediction of battery end-of-life on the basis of observing voltage discharge curves since the discharge characteristics of cathode-limited cells are relatively uniform.

In its more general aspects, the capacitor of the present invention may be employed in conjunction with electrochemical cells in which the anode comprises any active metal above hydrogen in the EMF series, such as an alkali or alkaline earth metal or aluminum. Lithium is a preferred anode material.

Cathode materials in electrochemical cells suitable for use in conjunction with the capacitor of the present invention are most preferably solid and comprise as active components thereof metal oxides such as vanadium oxide ($V_6O_{13}$), silver vanadium oxide ($Ag_2V_4O_{11}$), or manganese dioxide. Of those cathode materials, thermally treated electrolytic manganese dioxide is most preferred. As mentioned above, the cathode of the electrochemical cell may also comprise carbon monofluoride (CFx) and hybrids thereof, e.g., $CF_x$+ $MnO_2$, or any other known active electrolytic components in combination. By "solid" cathodes, we mean pressed porous solid cathodes, as known in the art. Such cathodes are typically made by mixing one or more active components with carbon and poly (tetrafluorethylene) and pressing those components to form a porous solid structure.

It is to be understood, however, that battery chemical systems other than those set forth explicitly above may be employed in conjunction with the capacitor of the present invention, including, but not limited to, cathode/anode systems such as: silver oxide/lithium; $MnO_2$/lithium; $V_2O_5$/lithium; copper silver vanadium oxide/lithium; copper oxide/lithium; lead oxide/lithium; $CF_x$/lithium; chromium oxide/lithium; bismuth-containing oxides/lithium and lithium ion rechargeable batteries.

FIG. 3(h) shows PCD 10 having left-hand shield 350 connected to right-hand shield 340 and feedthrough 390 projecting upwardly from both shield halves. Activity sensor 400 and patient alert apparatus 410 are shown disposed on the side lower portion of left-hand shield 350. Left-hand shield 350 and right-hand shield 340 are subsequently closed and hermetically sealed (not shown in the Figures).

Figure 4:
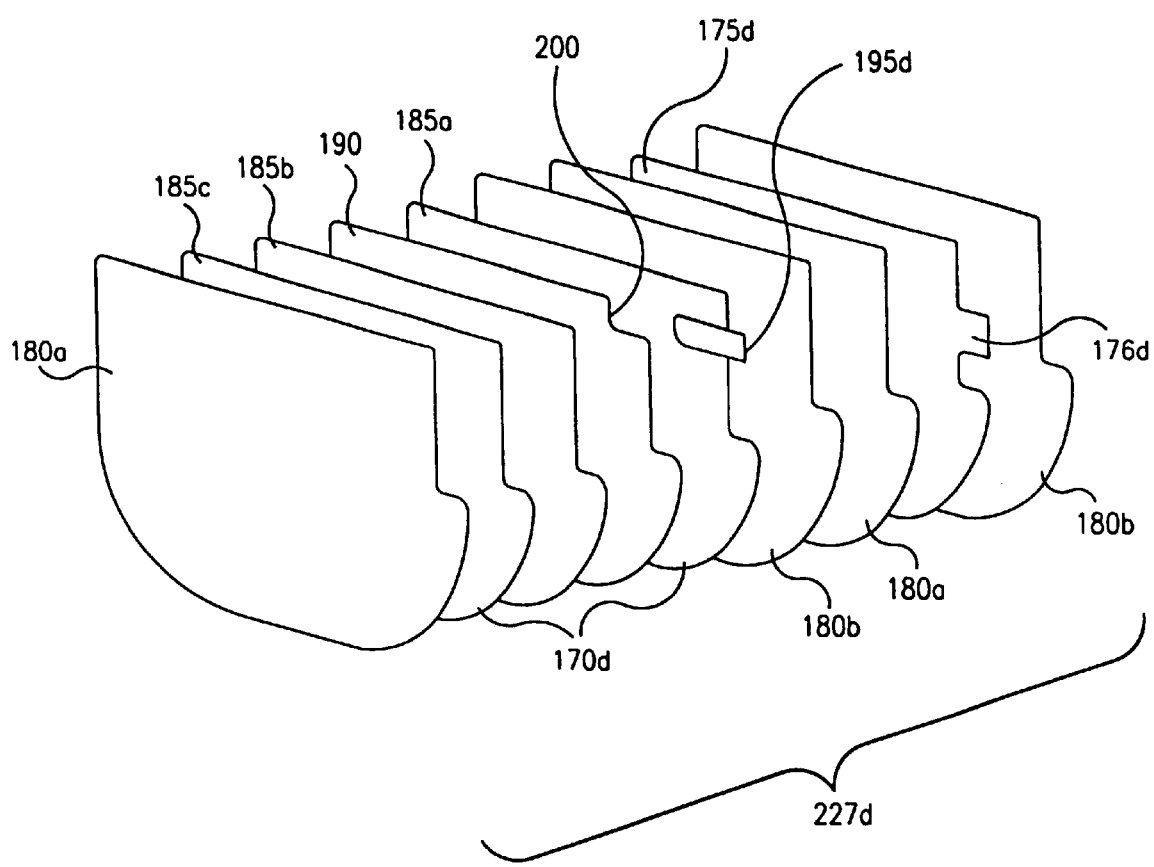
FIG. 4 shows an exploded view of one embodiment of a single electrode sub-assembly of a capacitor of the present invention.

FIG. 4 shows an exploded view of one embodiment of a single anode/cathode sub-assembly 227 capacitor 265 of the present invention. The capacitor design described herein employs a stacked configuration, where anode/cathode sub-assembly 227 comprises alternating substantially rectangularly-shaped anode layers 185 and cathode layers 175, with substantially rectangularly-shaped separator layers 180 being interposed therebetween. In one preferred embodiment of the present invention, two individual separator layers 180 are disposed between anode sub-assembly 170 and cathode layer 175. One anode layer 185a has anode tab 195d attached thereto, more about which we say below. Cathode layer 175d most preferably has cathode tab 176 formed integral thereto and projecting from the periphery thereof.

The shapes of anode layers 185, cathode layers 175 and separator layers 180 are primarily a matter of design choice, and are dictated largely by the shape or configuration of case 90 within which those layers are ultimately disposed. In a die apparatus according to one preferred method of the present invention, the punch and cavity of the present invention employed in forming those layers should be configured to produce layers having a desired predetermined shape, such as those shown in FIG. 4. A principal advantage of the capacitor construction of the present invention is that anode layers 185, cathode layers 175 and separator layers 180 may assume any arbitrary shape to optimize packaging efficiency.

Anode layers 185, cathode layers 175 and separator layers 180 are most preferably formed of materials typically used in high quality aluminum electrolytic capacitors. Individual anode layers 185 are typically somewhat stiff and formed of high-purity aluminum processed by etching to achieve high capacitance per unit area. Cathode layers 175 are preferably high purity and are comparatively flexible. Paper separators 180 are most preferably made slightly larger than cathode layers 175 and anode layers 185 to ensure that a physical barrier is disposed between the anodes and the cathodes of the finished capacitor.

Figure 9:
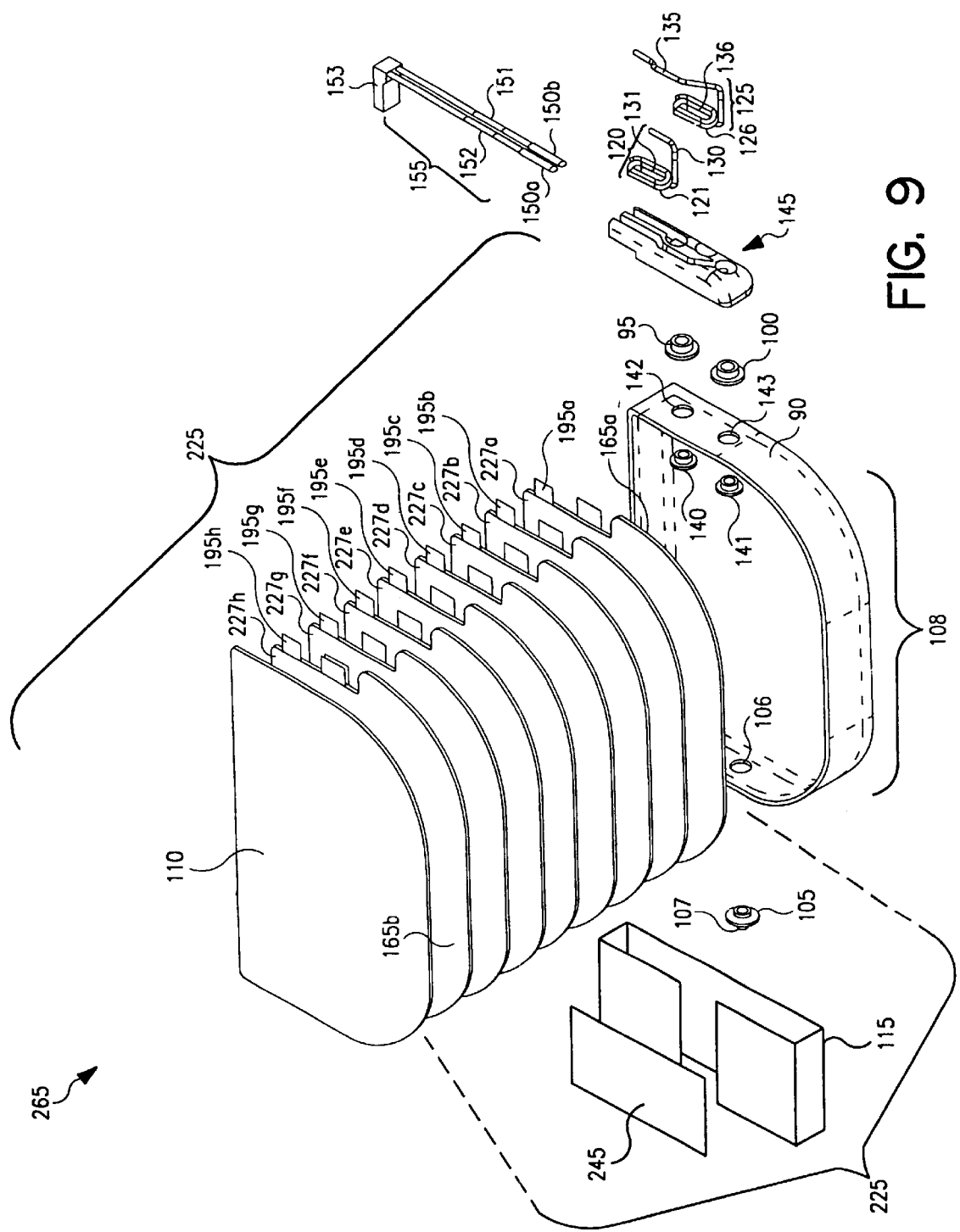
FIG. 9 shows an exploded top perspective view of one embodiment of a capacitor of the present invention employing the electrode assembly of FIGS. 6, 7 and 8 therein.

In one embodiment of capacitor 265 of the present invention, and as shown in FIGS. 6 and 9, sub-assembly 227d shown in FIG. 4 is but one of a plurality of anode/cathode sub-assemblies 227a through 227h disposed within capacitor 265. Likewise, a plurality of anode layers 185 and separator layers 180 is most preferably disposed within each sub-assembly, while a single cathode layer 175 is disposed within each sub-assembly 227. FIG. 4 shows anode sub-assembly 170d, one of a plurality of anode sub-assemblies disposed in capacitor 265. Anode sub-assembly 170d in FIG. 4 is but one embodiment of anode sub-assembly 170 of the present invention, and is shown therein as most preferably comprising three unnotched anode layers 185, one notched anode layer 190 and one anode tab 195.

It will be understood by those skilled in the art, however, that the precise number of sub-assemblies 227 selected for use in a given embodiment of the present invention will depend upon the energy density, volume, voltage, current, energy output and other requirements placed upon capacitor 265. As few as two anode/cathode sub-assemblies 227 and as many as 50 anode/cathode sub-assemblies 227 are included within the scope of the present invention.

Similarly, it will be understood by those skilled in the art that the precise number of notched and unnotched anode layers 185, anode tabs 195, anode sub-assemblies 170, cathode layers 175 and separator layers 180 selected for use in a given embodiment of anode/cathode sub-assembly 227 of the present invention will depend upon the energy density, volume, voltage, current, energy output and other requirements placed upon capacitor 265.

It will now become apparent that a virtually unlimited number of combinations and permutations respecting the number of anode/cathode sub-assemblies 227, and the number of unnotched and notched anode layers 185 forming anode sub-assembly 170, anode sub-assemblies 170, anode tabs 195, cathode layers 175 and separator layers 180 disposed within each anode/cathode sub-assembly 227, may be selected according to the particular requirements of capacitor 265, and further that such combinations and permutations fall within the scope of the present invention.

Referring to FIG. 4 again, anode sub-assembly 170 most preferably comprises a plurality of non-notched anode layers 185, notched anode layer 190, anode tab 195 and anode tab notch 200. Anode layers 185 and 190 are formed of anode foil 65 (not shown in the Figures). It has been discovered that the anode foil of the present invention is most preferably through-etched, has a high specific capacitance (at least about 0.3, at least about 0.5 or most preferably at least about 0.8 microfarads/$cm^2$), has a dielectric withstand parameter of at least 425 Volts DC, a thickness ranging between about 50 and about 200 micrometers, more preferably between about 75 and 150 micrometers, more preferably yet between about 90 and about 125 micrometers, and most preferably being about 100 micrometers thick, and a cleanliness of about 1.0 mg/$m^2$ respecting projected area maximum chloride contamination.

Thin anode foils are preferred in the present invention, especially if they substantially maintain or increase specific capacitance while reducing the thickness of electrode assembly 225, or maintain the thickness of electrode assembly 225 while increasing overall capacitance. For example, it is contemplated in the present invention that individual anode layers 185 have a thickness of about 10 micrometers, about 20 micrometers, about 30 micrometers, about 40 micrometers, about 50 micrometers, about 60 micrometers, about 70 micrometers, about 80 micrometers, about 90 micrometers, about 100 micrometers, about 110 micrometers, about 120 micrometers, about 130 micrometers, about 140 micrometers and about 150 micrometers.

In one preferred embodiment of the present invention, anode foil 65 has a rated surge voltage of 390 Volts, an initial purity of about 99.99% aluminum, a final thickness of about 104 micrometers, plus or minus about five micrometers, and a specific capacitance of about 0.8 microfarads per square centimeter. Suitable anode foils for practicing the present invention are commercially available on a widespread basis.

Cathode layers 175 are most preferably formed from cathode foil 70 (not shown in the Figures). Some preferred parameters of cathode foil have been discovered to include high surface area (i.e., highly etched cathode foil), high specific capacitance (preferably at least 200 microfarads/$cm^2$, and at least 250 microfarads/$cm^2$ when fresh), a thickness of about 30 micrometers, a cleanliness of about 1.0 mg/$m^2$ respecting projected area maximum chloride contamination, and a purity which may be less than corresponding to the starting foil material from which anode foil 65 is made.

In one preferred embodiment of the present invention, cathode foil 70 has an initial purity of at least 99% aluminum, and more preferably yet of about 99.4% aluminum, a final thickness of about 30 micrometers, and an initial specific capacitance of about 250 microfarads per square centimeter.

In other embodiments of the present invention, cathode foil 70 has a specific capacitance ranging between about 100 and about 500 microfarads/$cm^2$, about 200 and about 400 microfarads/$cm^2$, or about 250 and about 350 microfarads/$cm^2$, a thickness ranging between about 10 and about 150 micrometers, about 15 and about 100 micrometers, about 20 and about 50 micrometers, or about 25 and about 40 micrometers.

It is generally preferred that the specific capacitance of cathode foil 70 be as high as possible, and that cathode layer 175 be as thin as possible. For example, it is contemplated in the present invention that individual cathode layers 175 have specific capacitances of about 100 microfarads/$cm^2$, about 200 microfarads/$cm^2$, about 300 microfarads/$cm^2$, about 400 microfarads/$cm^2$, about 500 microfarads/$cm^2$, about 600 microfarads/$cm^2$, about 700 microfarads/$cm^2$, about 800 microfarads/$cm^2$, about 900 microfarads/$cm^2$, or about 1,000 microfarads/$cm^2$. Suitable cathode foils for practicing the present invention are commercially available on a widespread basis.

In still other embodiments of the present invention, cathode foil 70 is formed of materials or metals in addition to aluminum, aluminum alloys and "pure" aluminum.

Separator layers 180 are most preferably made from a roll or sheet of separator material 75. In one preferred embodiment, separator material 75 is a pure cellulose, very low halide or chloride content Kraft paper having a thickness of about 0.0005 inches, a density of about 1.06 grams/$cm^3$, a dielectric strength of 1,400 ac Volts per 0.001 inches thickness, and a low number of conducting paths (about 0.4/$ft^2$ or less). Separator layers 180 are preferably cut slightly larger than anode layers 170 and cathode layers 175 to accommodate misalignment during the stacking of layers and to prevent subsequent shorting between electrodes of opposite polarity.

It is preferred that separator layers 180 be formed of a material that: (a) is chemically inert; (b) is chemically compatible with the selected electrolyte; (c) may be impregnated with the electrolyte to produce a low resistance path between adjoining anode and cathode layers, and (d) physically separates adjoining anode and cathode layers. Separator layers 180 may also be formed of materials other than Kraft paper, such as Manila paper, porous polymeric materials or fabric gauze materials. For example, porous polymeric materials may be disposed between anode and cathode layers of like those disclosed in U.S. Pat. Nos. 3,555,369 and 3,883,784 in some embodiments of the present invention.

In a preferred embodiment of the present invention, a liquid electrolyte saturates or wets separator layers 180 and is disposed within case 90. It is to be understood, however, that various embodiments of the present invention include within their scope a solid or adhesive electrolyte such as those disclosed in U.S. Pat. Nos. 5,628,801; 5,584,890; 4,942,501 and its continuations, U.S. Pat. Nos. 5,146,391 and 5,153,820. Note that in some embodiments of the present invention, an appropriate inter-electrode adhesives/electrolyte layer may be employed in place of paper, gauze or porous polymeric materials to form separator layer 180.

It will also be understood by those skilled in the art that there exist many different types and methods for making anode 65, cathode foil 70 and separator material 75. What we disclose herein, therefore, are only preferred materials, methods and apparatus for making a preferred embodiment of capacitor 265 of the present invention, and its various components, and not all the materials, methods and apparatus suitable for practicing the present invention and falling within the scope thereof.

Continuing to refer to FIG. 4, a first preferred step in assembling a flat aluminum electrolytic capacitor is to cut anode layers 185 and 190, anode tabs 195, cathode layers 175 and separator layers 180. Those components are most preferably cut to shape using dies having low wall-to-wall clearance, where inter-wall spacing between the substantially vertically-oriented corresponding walls of the punch and die is most preferably on the order of about 6 millionths of an inch per side. Larger or smaller inter-wall spacings between the substantially vertically-oriented corresponding walls of the punch and cavity, such as about 2, about 4, about 5, about 7, about 8, about 10 and about 12 millionths of an inch may also be employed in the present invention but are less preferred.

Such low clearance results in smooth, burr free edges being formed along the peripheries of anode layers 185 and 190, anode tabs 195, cathode layers 175 and separator layers 180. Smooth, burr free edges on the walls of the dies have been discovered to be critical respecting reliable performance of a capacitor.

The presence of burrs along the peripheries of anode layers 185 and 190, anode tabs 195, cathode layers 175 and separator layers 180 may result in short circuit and failure of the capacitor. The means by which anode foil, cathode foil and separator materials are cut or formed in the present invention may have a significant impact on the lack or presence of burrs and other cutting debris disposed about the peripheries of the formed or cut members. We have found that the use of low clearance dies produces an edge superior to that of other cutting methods, such as steel rule dies. The shape, flexibility and speed of a low clearance die has been discovered to be superior to that of laser or blade cutting.

Other methods of cutting or forming anode layers 185 and 190, anode tabs 195, cathode layers 175 and separator layers 180 falling within the scope of the present invention include, but are not limited to, steel rule die cutting, laser cutting, water jet cutting and blade cutting.

The preferred low clearance of the die apparatus of the present invention is especially important for cutting thin ductile materials such as cathode foil 70. In addition to improving reliability, burr and debris reduction permits reductions in the thickness of separator layer 180, thereby improving energy density of the capacitor. Angle cutting, where the face of the punch is not held parallel to the opposing floor of the die during the cutting step, is another less preferred method of cutting or forming anode layers 185 and 190, anode tabs 195, cathode layers 175 and separator layers 180 of the present invention.

It is preferred in the present invention to cut or otherwise form separator layer 180 such that its outer periphery conforms closely to that of the corresponding sidewalls of the interior of case 90. In preferred embodiments of the present invention, the periphery of separator layer is disposed within plus or minus 0.009 inches of the corresponding sidewalls of case 90. Such close conformity between the periphery of separator layer 180 and the corresponding internal sidewalls of case 90 has been discovered to provide the advantage of permitting separator layers 180 to immobilize or secure firmly in place electrode assembly 225 in case 90. This immobilization occurs because the separator paper forming separator layers 180 swells after electrolyte is added through fill port ferrule 105 into otherwise assembled and sealed capacitor 265.

In a preferred method of the present invention, foil or separator materials are drawn between the punch and cavity portions of a die having appropriate clearances on a roll. An air or hydraulically actuated press is then most preferably employed to actuate the punch or cavity portion of the die. The punch portion of the die is most preferably formed of hardened tool steel, or has other suitable wear resistant materials or coatings disposed on the cutting surfaces thereof. When the cavity of the die is aligned vertically, the punch portion of the die may travel either upwards or downwards towards the die cavity during a cutting cycle. In the former case, components are cut and drop downwardly into a container for use in subsequent assembly operations. In the latter case, components are cut and may be presented directly to automated assembly equipment, such as robots equipped with vacuum or other pick-up tooling, for subsequent processing. Low clearance dies of the type described herein may be supplied by Top Tool, Inc. of Minneapolis, Minn.

Anode sub-assembly 170 most preferably includes one notched anode layer 190, which facilitates appropriate placement and positioning of anode tab 195 within anode sub-assembly 170. More than one notched anode layer 190 may also be included in anode sub-assembly 170. It is preferred that the remaining anode layers of anode sub-assembly 170 be non-notched anode layers 185. Anode tab 195 is most preferably formed of aluminum strip material. In one preferred embodiment of the present invention, aluminum strip 80 has a purity of about 99.99% aluminum and a lesser degree of anodization than anode foil 65. When anode tab 195 is formed of a non-anodized material, cold welding of anode tab 195 to non-notched anode layers 185 may be accomplished with less force and deflection, more about which we say below. It is preferred that the thickness of anode tab 195 be about equal to that of notched anode layer 190. If more than one notched anode layer 190 is employed in anode sub-assembly 170, a thicker anode tab 195 may be employed.

Figure 13A:
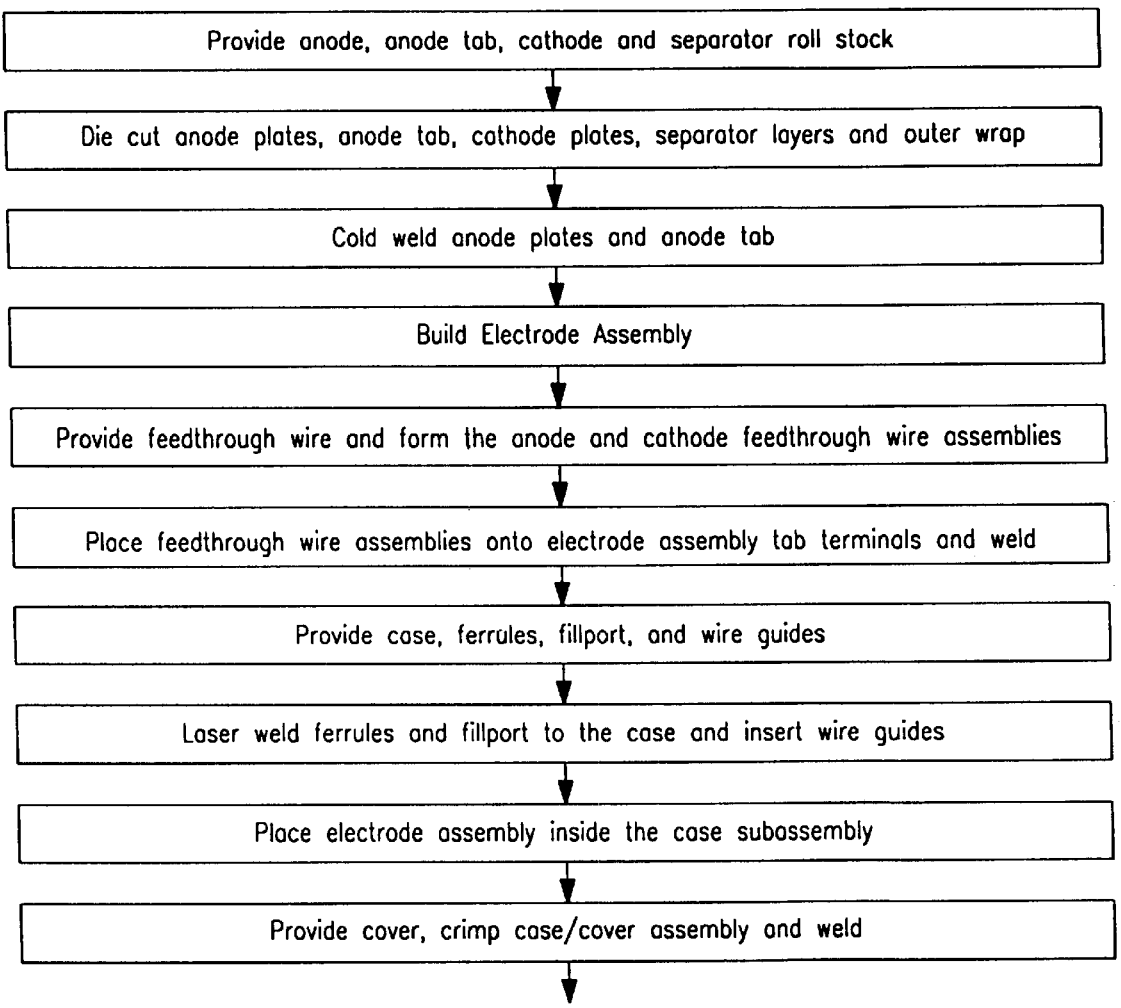
FIG. 13 shows a flow chart of one method of the present invention for making a capacitor of the present invention.
Figure 13B:
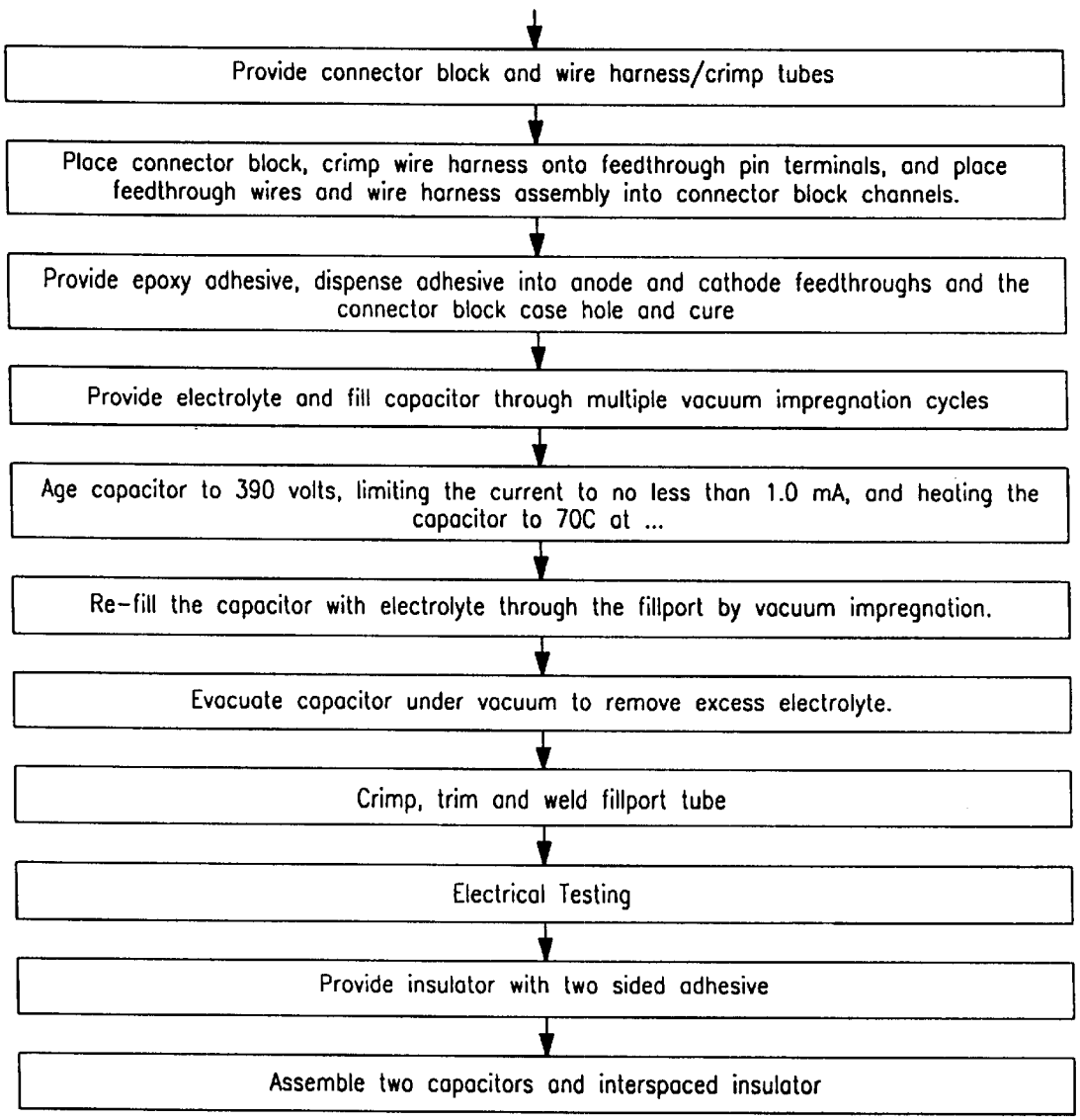

FIG. 13 shows a flow chart that describes generally one method, from beginning to end, of making flat aluminum electrolytic capacitor 265 of the present invention. FIGS. 14 through 20, on the other hand, show specific portions of the method or process described generally in FIG. 13.

Figure 14:
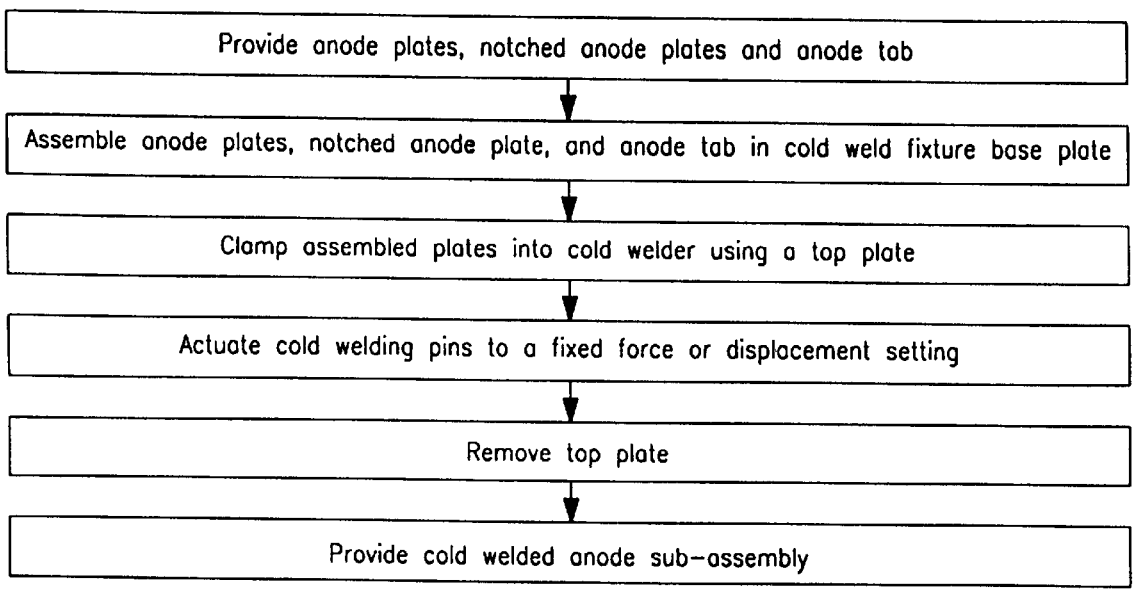
FIG. 14 shows a flow chart of one method of the present invention for making an anode layer of the present invention.

FIG. 14 shows a flow chart of one method of the present invention for making anode layer 170 of the present invention. In FIG. 14, non-notched anode layers 185, notched anode layer 190 and anode tab 195 are provided and assembled within cold welder 202 to form anode sub-assembly 170.

Figure 5A:
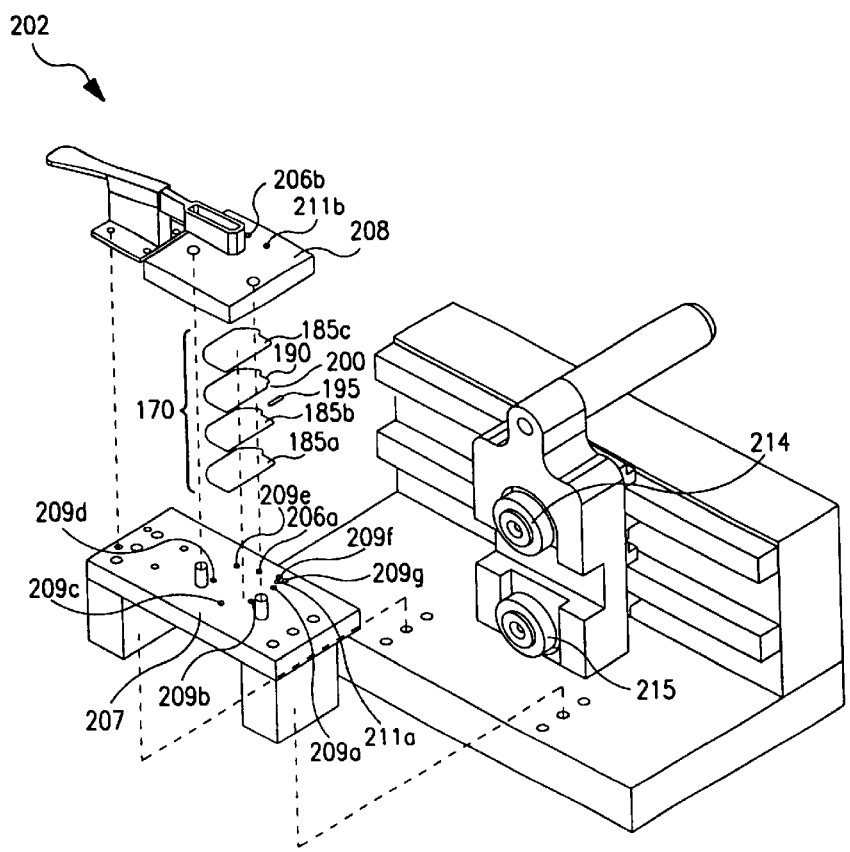
FIG. 5(a) shows an exploded perspective view of one embodiment of a cold welding apparatus in which anode layers of the electrode sub-assembly of FIG. 4 are cold-welded.
Figure 5B:
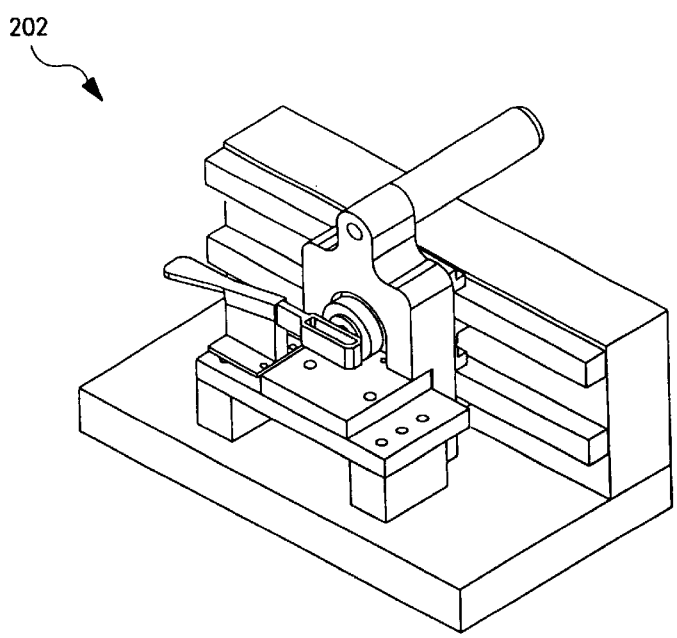
FIG. 5(b) shows an unexploded view of the cold welding apparatus of FIG. 5(a)

Referring now to FIGS. 5(*a*) through 5(*c*), two non-notched anode layers 185*a* and 185*b* are placed on cold welding fixture base layer 207 of cold welding apparatus 202. The various structural members of cold welding apparatus 202 are most preferably formed of precision machined stainless steel or a high strength aluminum alloy. Layers 185*a* and 185*b* are next aligned and positioned appropriately on cold welding fixture base layer 207 using spring loaded alignment pins 209*a* through 209*e*. Pins 209*a* through 209*e* retract upon top layer 208 being pressed downwardly upon layers 185*a* and 185*b* disposed within cold welding cavity 220. See also FIG. 5(*c*), where a cross-sectional view of cold welding apparatus 202 is shown.

Anode layer 190 is similarly disposed within cavity 220, followed by placing anode tab 195 within anode tab notch 200 in notched anode layer 190. Anode tab 195 is most preferably positioned along the periphery of notched anode layer 190 with the aid of additional spring loaded alignment pins 209*f* and 209*g* disposed along the periphery of anode tab 195. Non-notched anode layer 185*c* is then placed atop anode layer 190. Stacked anode sub-assembly 170 is then clamped between top plate 208 and base plate 207. Disposed within base plate 207 are anode layer cold welding pins 206*a* and anode tab cold welding pin 211*a*. Disposed within top plate 208 are anode layer cold welding pin 206*b* and anode tab cold welding pin 211*b*. Base plate 207 and top plate 208 are aligned such that the axes of cold welding pins 206*a* and 206*b* coincide with and are aligned respecting corresponding cold welding pins 211*a* and 211*b*.

Upper actuation apparatus 214 of cold welding apparatus 202 displaces cold welding pins 206*b* and 211*b* downwardly. Lower actuation apparatus 215 displaces cold welding pins 206*a* and 211*a* upwardly. In one embodiment of upper actuation apparatus 214 and lower actuation apparatus 215 of the present invention, pneumatic cylinders are employed to move pins 206*a*, 206*b*, 211*a* and 211*b*. In another embodiment of apparatus 214 and apparatus 215 of the present invention, a pair of rolling wheels is provided that move simultaneously and perpendicularly to the axes of pins 206*a*, 206*b*, 211*a*, and 211*b*. Still other embodiments of apparatus 214 and apparatus 215 of the present invention may employ hydraulic actuators, cantilever beams, dead weights, springs, servomotors electromechanical solenoids, and the like for moving pins 206*a*, 206*b*, 211*a* and 211*b*. Control of actuation apparatus 214 and apparatus 215 respecting pin displacement force magnitude and timing may be accomplished using any one or combination of constant load, constant displacement, solenoid controller, direct or indirect means.

Following clamping with top plate 208, cold welding pins 206*a*, 206*b*, 211*a* and 211*b* are actuated. Cold welds 205 and 210 in anode sub-assembly 170 are formed by compression forces generated when cold weld pins 206*a*, 206*b*, 211*a* and 211*b* are compressed thereagainst. See FIG. 6(*a*), where the preferred regions in which cold welds 205 and 210 are formed are shown. Cold welds 205 and 210 may be described as not only cold welds, but forged welds. This is because the interfacial boundaries between anode layers 185 are deformed in the region of welds 205 and 210, thereby disrupting oxide layers and bringing base metals into direct contact with one another where metallic bonding occurs. Metallic bonding increases the strength of the welds.

In one embodiment of the method of the present invention, a plurality of pneumatic cylinders function simultaneously in upper actuation apparatus 214 and lower actuation apparatus 215 to drive pins 206*a*, 206*b*, 211*a* and 211*b* against anode sub-assembly 170. Anode layer cold weld 205 and anode tab cold weld 210 are most preferably formed under direct constant load conditions, where pneumatic cylinders are pressurized to a predetermined fixed pressure. Anode layer cold weld 205 and anode tab cold weld 210 may also be formed under indirect constant displacement conditions, where pneumatic cylinders are pressurized until a displacement sensor placed across cold welding pins 206a, 206b, 211a or 211b generates a signal having a predetermined value, whereupon those pins are disengaged from sub-assembly 227.

In another embodiment of the method of the present invention, a cantilever beam mechanism is incorporated into upper actuation apparatus 214 and lower actuation apparatus 215. Anode layer cold weld 205 and anode tab cold weld 210 are formed under direct constant displacement conditions, where cantilever beams are actuated and cause upper and lower members 208 and 207 to engage sub-assembly 227 until a hard stop point is reached. An indirect load controlled system may also be employed in apparatus 214 and apparatus 215, where cantilever or other means include a load measuring sensor for controlling the stop point of the cantilever beam, for example, when a predetermined load is measured by the sensor.

The cross-sectional shape of cold weld pins 206a, 206b, 211a and 211b may be square, circular, oval or any other suitable shape. The shape of the ends of cold weld pins 206a, 206b, 211a and 211b may be flat, rounded, domed or any other suitable shape appropriate for selectively controlling the properties of the cold welds produced therein. Likewise, more or fewer than four cold weld pins may be employed in the present invention. The ends of cold weld pins 206a, 206b, 211a and 211b are most preferably rounded or domed and circular in cross-section. In a preferred embodiment of the present invention, cold weld pins 206a, 206b, 211a and 211b have a diameter of about 0.060" and further have a beveled or radiused end. Cold weld pins 206a, 206b, 211a and 211b are preferably made from a high strength material that does not readily deform under the pressures obtained during welding, such as stainless steel, titanium, tool steel or HSLA steel. The ends or sidewalls of cold welding pins 206a, 206b, 211a and 211b may be coated, cladded or otherwise modified to increase wear resistance, deformation resistance or other desirable tribilogical attributes of the pins.

The primary function of cold welds 205 and 210 is to provide electrical interconnections between layers 185a, 185b, 185c and 190 and anode tab 195, while minimizing the overall thickness of anode sub-assembly 170 in the regions of welds 205 and 210. We have discovered that typical prior art commercial cylindrical capacitors exhibit a significant increase in the thickness of the anode layer in the regions of the cold welds. This increase in thickness is typically on the order of about two times the thickness of the tab, or about 0.008 inches. In the case of cylindrical capacitors where only one or two non-coincident tab connections are present, the overall effect on anode layer thickness may be minimal. In a stacked layer design having many more interconnections and welds, however, increases in weld zone thickness have been found to significantly increase the overall thickness of the anode layer and the capacitor.

In one method and corresponding apparatus of the present invention, no or an inappreciable net increase in anode sub-assembly 170 thickness results when cold weld geometries and formation processes are appropriately optimized. Several embodiments of anode-assembly 170 have been found to have no more than about a 20% increase in layer thickness due to the presence of cold welds, as compared to about a 200% increase in thickness resulting from cold welds found in some commercial cylindrical capacitors. In the present invention, two, three, four, five, six or more anode layers 185 and 190 may be cold-welded to form anode sub-assembly 170.

Figure 6A:
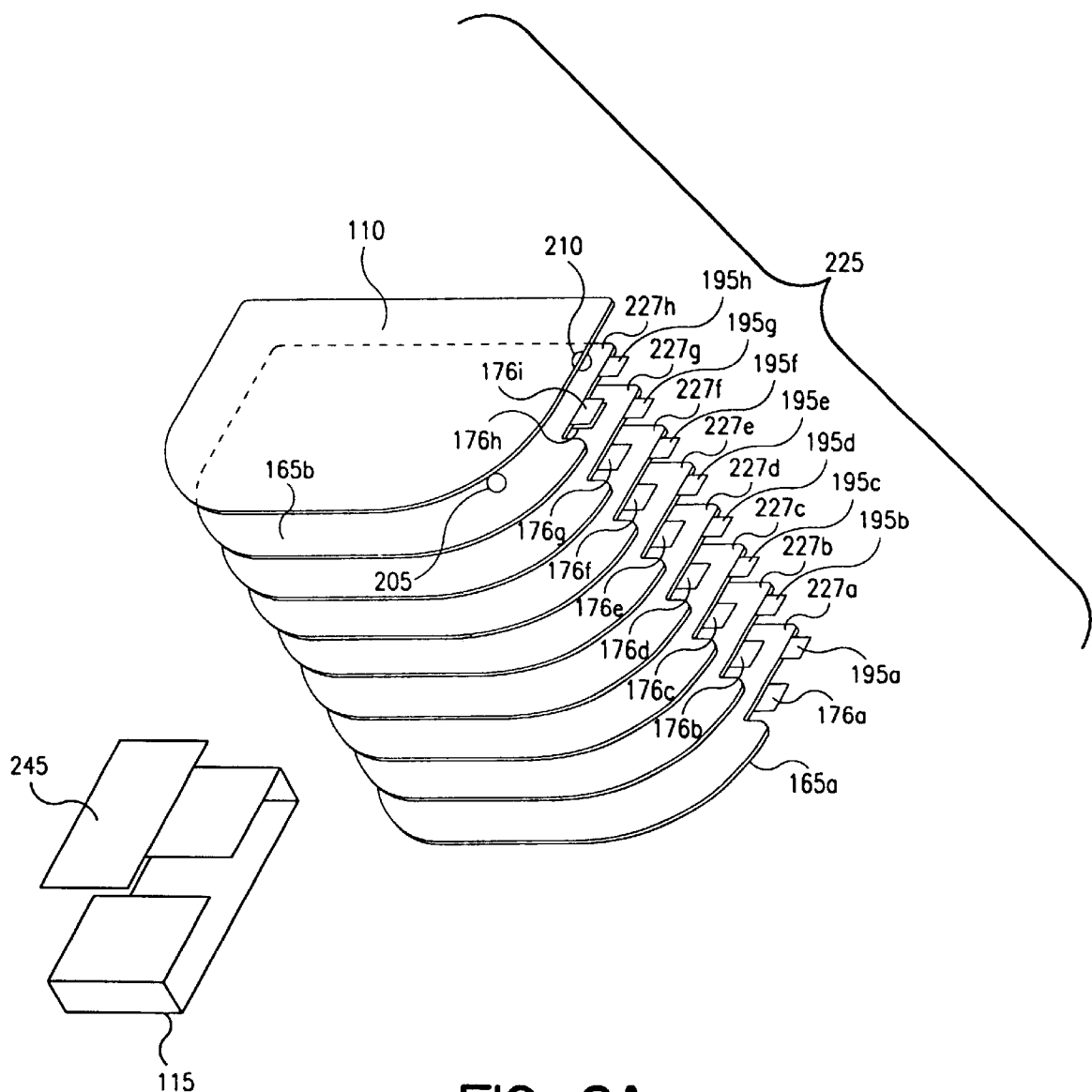
FIG. 6(a) shows an exploded top perspective view of one embodiment of an electrode assembly of a capacitor of the present invention.
Figure 6B:
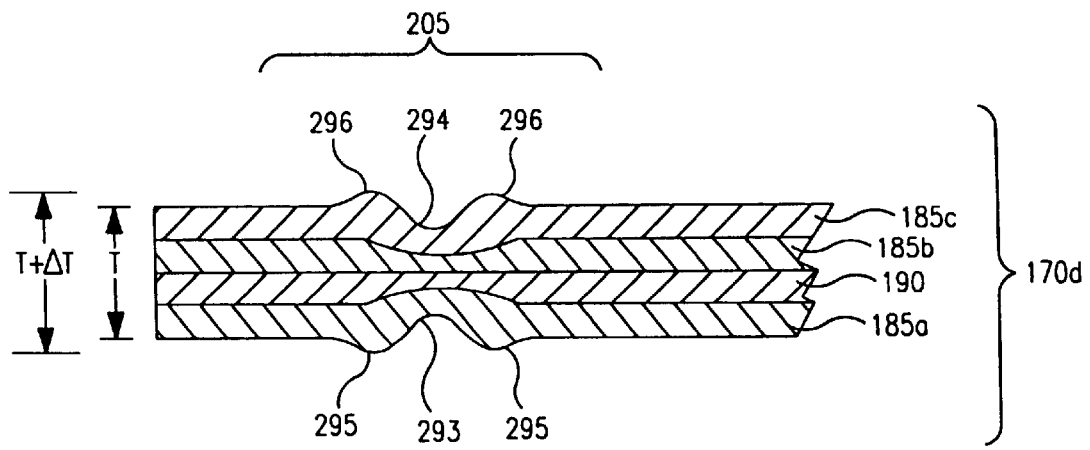
FIG. 6(b) shows a cross-sectional view of a portion of one embodiment of a cold-welded anode assembly of the present invention.

FIG. 6(b) shows a cross-sectional view of a portion of one embodiment of a cold-welded anode assembly of the present invention. Anode layers 185a, 190, 185b and 185c are cold-welded together at weld 205 through the compressive action of pins 206a and 206b mounted in bottom plate 207 and top plate 208, respectively. Pins 206a and 206b form central depressions 293 and 294, respectively, in anode sub-assembly 170d, and further result in the formation of rims 295 and 296, respectively. Rims 295 and 296 project downwardly and upwardly, respectively, from the surrounding surfaces of anode subassembly 170d, thereby increasing the overall thickness T of anode subassembly 170d by $\Delta T$ in respect of the non-cold-welded surrounding regions or portions thereof.

Figure 6C:
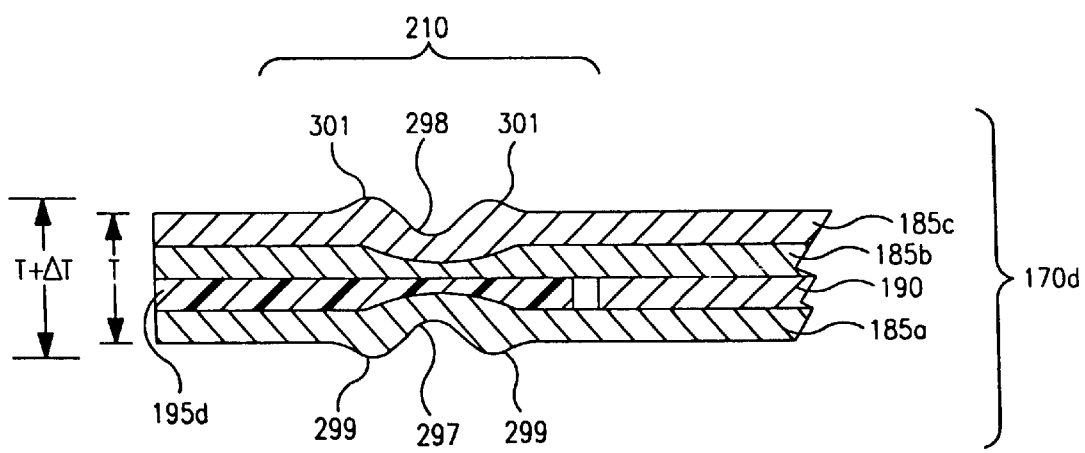
FIG. 6(c) shows a cross-sectional view of another portion of one embodiment of a cold-welded anode assembly of the present invention.

FIG. 6(c) shows a cross-sectional view of another portion of one embodiment of a cold-welded anode assembly of the present invention. Anode layers 185a, 185b, 185c and tab 195d are cold-welded together at weld 210 through the compressive action of pins 211a and 211b mounted in bottom plate 207 and top plate 208, respectively. Pins 211a and 211b form central depressions 297 and 298, respectively, in anode sub-assembly 170d, and further result in the formation of rims 299 and 301, respectively. Rims 299 and 301 project downwardly and upwardly, respectively, from the surface of anode subassembly 170d, thereby increasing overall thickness T of anode subassembly 170d by $\Delta T$ in respect of the non-cold-welded regions thereof.

Anode subassembly 170d has a thickness defined by the equation:

$$T = nt$$

where T is the overall thickness of anode subassembly 170d in non-cold-welded regions, n is the number of anode layers 185 and/or 190 in anode subassembly 170d, and t is the thickness of individual anode layers 185 and/or 190 or anode tab 195. The maximum overall thickness of anode subassembly 170d in the region of cold welds 205 or 210 is then defined by the equation:

$$T + \Delta T = nt + \Delta T$$

We have discovered that it is highly desirable to form anode subassembly such that the ratio $\Delta T/T$ is less than or equal to 0.05, 0.1, 0.15, 0.20, 0.25, 0.30, 0.35, 0.40, 0.45 or 0.50. The lower the value of the ratio $\Delta T/T$, the greater the volumetric efficiency of capacitor 265. Additionally, the overall thickness of capacitor 265 may be reduced when the value of the ratio $\Delta T/T$ is made smaller.

Referring now to FIG. 6(a), we have further discovered that the overall thickness of electrode assembly 225 may be reduced further by staggering or offsetting horizontally the respective vertical locations of tabs 195a through 195h (and corresponding cold welds 210). In this embodiment of the present invention, tabs 195a 195b, for example, are not aligned vertically in respect of one another. Such staggering or offsetting of tabs 195 permits the increases in thickness $\Delta T$ corresponding to each of anode subassemblies 170a through 170h to be spread out horizontally over the perimeter or other portion of electrode assembly 225 such that increases in thickness $\Delta T$ do not accumulate or add constructively, thereby decreasing the overall thickness of electrode assembly 225. Cold welds 205 may similarly be staggered or offset horizontally respecting one another and cold weld 210 to achieve a reduction in overall thickness of electrode assembly 225.

In another embodiment of the present invention, anode sub-assembly 170 comprises a plurality of three, four, five or more anode layers 185 and 190, each sub-assembly most preferably having at least one anode layer having a corresponding anode tab 195 attached thereto or forming a portion thereof, the layers being cold welded together to form anode sub-assembly 170. For example, an anode sub-assembly 170 may comprise six anode layers 185 constructed by cold-welding two separate triple anode layers 185 that were previously and separately cold-welded or otherwise joined together. Attentively, anode sub-assembly 170 layer may comprise seven anode layers constructed by cold-welding together one triple anode layer 185 and one quadruple anode layer 185 that were previously and separately cold-welded or otherwise joined together. In another embodiment of the present invention, multiple notched anode layers 190 may employed in anode sub-assembly 170, thereby permitting the use of a thicker anode tab material 70.

The geometry of base plate 207 and top plate 208 in the regions surrounding cold welding pins 206a, 206b, 211a and 211b has been discovered to affect the properties of cold welds 205 and 210. In a preferred method of the present invention, the mating surfaces of plates 207 and 208 surfaces have no radiused break formed in the perimeters of the pin holes. We have found that the presence of radiused breaks or chamfers in those regions may cause undesired deformation of cold welds 205 and 210 therein. Such deformation may result in an increase in the thickness of anode sub-assembly 170, which may translate directly into an increase in the thickness of capacitor 265. Note further that the increase in thickness so resulting is a multiple of the number of anode sub-assemblies 170 present in electrode assembly 225. In less preferred methods of the present invention radiused breaks or chamfers may be employed in the region of the pin holes in base plate 207 and top plate 208, but appropriate capacitor design accommodations are most preferably made, such as staggering the positions of adjoining stacked cold welds.

Figure 15:
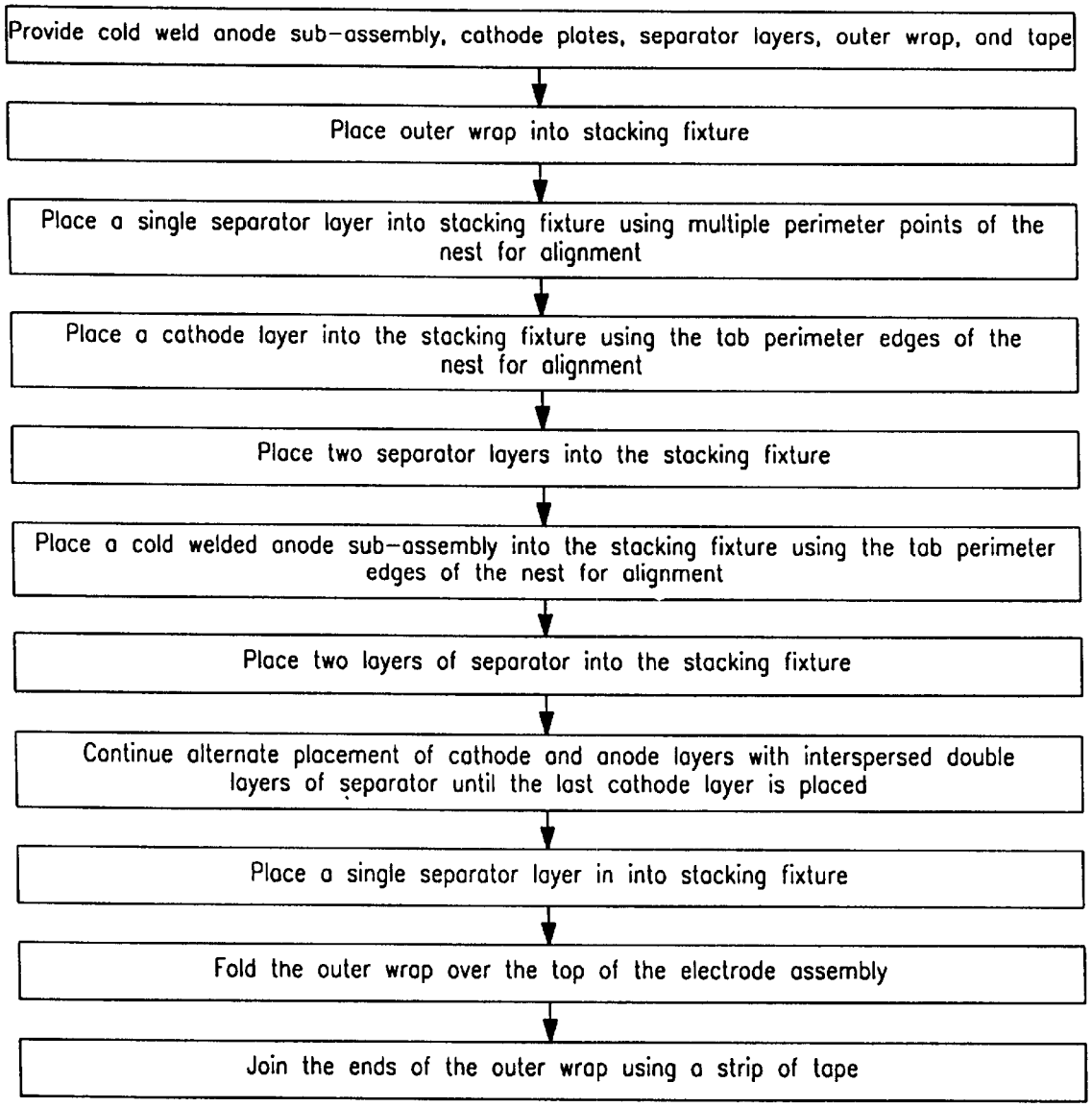
FIG. 15 shows a flow chart of one method of the present invention for making an electrode assembly of the present invention.

As shown in FIG. 14, once cold welding pins 206a, 206b, 211a and 211b have been actuated against anode sub-assembly 170, top plate 208 is removed and cold-welded anode sub-assembly 170 is provided for further stacking of electrode subassembly 227. FIG. 15 shows a flow chart corresponding to one preferred method for making electrode assembly 225 of the present invention. See also FIG. 6(a), where an exploded top perspective view of one embodiment of an electrode assembly 225 of capacitor 265 of the present invention is shown. As illustrated in FIGS. 4, 6(a) and 15, electrode assembly 225 most preferably comprises a plurality of cold-welded anode sub-assemblies 175a through 175h, a plurality of cathode layers 175a through 175l, a plurality of separator layers 180, outer separator layers 165a and 165b, outer wrap 115 and wrapping tape 245.

Outer wrap 115 is most preferably die cut from separator material 75 described supra, but may be formed from a wide range of other suitable materials such as polymeric materials, aluminum, suitable heat shrink materials, suitable rubberized materials and synthetic equivalents or derivatives thereof, and the like.

Wrapping tape 245 is most preferably cut from a polypropylene-backed acrylic adhesive tape, but may also be replaced by a staple, an ultrasonic paper joint or weld, suitable adhesives other than acrylic adhesive, suitable tape other than polypropylene-backed tape, a hook and corresponding clasp and so on.

Outer wrap 115 and wrapping tape 245 together comprise an electrode assembly wrap which has been discovered to help prevent undesired movement or shifting of electrode assembly 225 during subsequent processing. It will now become apparent to one skilled in the art that many means other than those disclosed explicitly herein exist for immobilizing and securing electrode assembly 225 during subsequent processing which accomplish substantially the same function as the electrode assembly wrap comprising outer wrap 115 and wrapping tape 245. Alternative means for immobilizing and securing electrode assembly 225 other than those described hereinabove exist. Such alternative means include, but are not limited to, robotic or other mechanical clamping and securing means not necessarily forming a portion of electrode assembly 225, adhesive electrolytes for forming separator layers 180, and so on.

The stacking process by which electrode assembly 225 is most preferably made begins by placing outer wrap 115 into a stacking fixture followed by placing outer paper or separator layer 165a thereon. Next, cathode layer 175a is placed atop separator layer 165a, followed by separator layers 180a and 180b being disposed thereon. Cold-welded anode sub-assembly 170a is then placed atop separator layer 180b, followed by placing separator layers 180a and 180b thereon, and so on. The placement of alternating cathode layers 175 and anode layers 170 with separator layers 180a and 180b interposed therebetween continues in the stacking fixture until final cathode layer 175h has been placed thereon.

In the embodiment of electrode assembly 225 shown in FIG. 6(a), eight anode sub-assemblies (anode sub-assemblies 170a through 170h) and nine cathode layers (cathode layers 175a through 175i) are illustrated. The voltage developed across each combined anode sub-assembly/separator layer/cathode layer assembly disposed within electrode assembly 225 most preferably ranges between about 360 and about 390 Volts DC. As described below, the various anode sub-assemblies of electrode assembly 225 are typically connected in parallel electrically, as are the various cathode layers of electrode assembly 225.

Consistent with the discussion hereinabove concerning FIG. 4, it will now be understood by one skilled in the art that electrode assembly 225 shown in FIG. 6(a) is merely illustrative, and does not limit the scope of the present invention in any way respecting the number or combination of anode sub-assemblies 170, cathode layers 175, separator layers 180, anode tabs 195, cathode tabs 176, and so on. The number of electrode components is instead determined according to the total capacitance required, the total area of each layer, the specific capacitance of the foil employed and other factors.

In another embodiment of electrode assembly 225 of the present invention, the number of anode layers 185 employed in each anode sub-assembly 170 is varied in the stack. Such a design permits the fabrication of capacitors having the same layer area but nearly continuously varying different and selectable total capacitances that a user may determine by increasing or decreasing the number of anode layers 180 included in selected anode sub-assemblies 170 (as opposed to adding or subtracting full anode/cathode sub-assemblies 227 from electrode assembly 225 to thereby change the total capacitance). Following placement of cathode layer 175l in the stack, outer paper layer 165b is placed thereon, and outer wrap 115 is folded over the top of electrode assembly 225. Wrapping tape 245 is then holds outer wrap 115 in place and secures the various components of electrode assembly 225 together.

The physical dimensions of separator layers 165 and 180 are most preferably somewhat larger than those of anode sub-assemblies 170 and cathode layers 175 to prevent contact of the electrodes with the case wall or electrical shorting between opposing polarity electrode layers due to the presence of burrs, stray or particulate material, debris or imperfections occurring therein. The reliability and functionality of capacitor 265 are compromised if a portion of anode sub-assembly 170 comes into contact with a conducting case wall, if a burr on the periphery of anode sub-assembly 170 or cathode layer 175 comes into contact with an adjoining layer of opposing polarity, or if separator layer 180*a* or 180*b* does not provide sufficient electrical insulation between adjoining opposite-polarity electrode layers and conducting particulate matter bridges the gap therebetween.

The additional separator material most preferably disposed about the periphery of electrode assembly 225 is referred to herein as separator overhang. Decreasing the amount of separator overhang increases the energy density of capacitor 265. It is beneficial from an energy density optimization perspective, therefore, to decrease the amount or degree of separator overhang. The amount of separator overhang required has been discovered to be primarily a function of the stack-up tolerance characteristic of the stacking method employed.

In commercial cylindrical capacitors, we discovered that the amount of separator overhang is typically on the order of 0.050" to 0.100". Fayram et al. in the foregoing '851 patent describe a flat aluminum electrolytic capacitor wherein the housing of the capacitor has at least two internal alignment members. Those alignment members necessarily add volume to the capacitor while taking away from the total amount of "active" electrode material available, thereby decreasing the energy density of the capacitor.

We discovered a method of the present invention for assuring consistent registration of separator layers 165 and 180, anode sub-assemblies 170 and cathode layers 175 in electrode assembly 225: stacking the various elements of electrode assembly 225 using robotic assembly techniques. More particularly, the various electrode and separator layers of electrode assembly 225 are stacked and aligned using an assembly workcell comprising four Seiko 4-axis SCARA Model No. TT8800 and TT8500, or equivalent, to pick up and place the various electrode and separator elements in an appropriate stacking fixture. Other suitable methods of the present invention for stacking and registering electrode and separator layers include cam driven walking beam assembly machine techniques, rotary table machine techniques, multiple station single stacking machine techniques, and the like.

In a preferred method of the present invention, a preformed or cut separator, electrode layer or sub-assembly is presented to a robot arm, which then picks the part up with end-of-arm tooling. A Venturi system produces a vacuum in the end-of-arm tooling. The system creates a vacuum at an appropriate time such that the part is sucked up onto the end-of-arm tooling. The vacuum is next released when the part is placed in the stacking fixture. A direct vacuum system, such as rubber suction cups, or other contact or non-contact pick up robotic or manual assembly methods may also be employed in accordance with other methods of the present invention. The position of the part is robotically translated from the pickup point into the stacking fixture by the robot arm with an accuracy of 5 thousands of an inch or less. After placing the part in the stacking fixture, part alignment is most preferably verified electronically with a SEIKO COGNEX 5400 VISION System, or equivalent, in combination with a SONY XC-75 camera, or equivalent. The camera is mounted on the robot arm to permit the accuracy of part placement to be verified. This system can accurately determine the position of each part or element in electrode assembly 225 to within 0.01 millimeters. Once all layers have been placed in the stacking fixture by the robot arm, the stack is presented for wrapping.

The foregoing methods of the present invention permit precise alignment and stacking of separator layers 165 and 180, anode sub-assemblies 170 and cathode layers 175 in electrode assembly 225, while minimizing the addition of undesirable unused volume to capacitor 265.

We discovered another method for assuring registration of separator layers 165 and 180, anode sub-assembly 170 and cathode layer 175 in electrode assembly 225, wherein alignment elements disposed within the stacking fixture are employed in a manual process which utilizes fixture registration points. In such a method, the stacking fixture has several alignment elements such as posts or sidewalls disposed about its periphery for positioning separator layers 165 and 180. Because cathode layers 175 and anode sub-assemblies 170 do not extend to the periphery of the separator, an alternative means for accurately positioning those electrodes becomes necessary.

Positioning of alternating cathode layers 175 and anode sub-assemblies 170 is most preferably accomplished using alignment elements such as posts or sidewalls disposed about the periphery of cathode tab 176 and anode tab 195. It has been discovered that the accuracy of layer placement and positioning is primarily a function of the length of the electrode tabs. The longer the tab, the less significant the alignment error becomes. Electrode tab length must typically be balanced against the loss of electrode material which occurs during die cutting, which in turn results primarily due to the longer length of cathode tab 176 in respect of the length of anode tab 195. Tabs 176 and 195 may include or contain alignment features therein having any suitable geometry for facilitating registration and positioning in respect of alignment elements. Any additional tab length utilized for registration of the electrode layers is most preferably trimmed from electrode assembly 225 during the process of electrode tab interconnection (more about which we say below).

Another method of the present invention for ensuring registration of separator layers 165 and 180, anode sub-assembly 170 and cathode layer 175 in electrode assembly 225 which does not require the use of internal alignment elements within capacitor 265 is enveloping or covering anode sub-assembly 170 and cathode layer 175 with separator material. In this method of the present invention, separator layers 180*a* and 180*b* are combined into a single die cut piece part that is folded around either anode sub-assembly 170 or cathode layer 175. The free edges of the separator are then secured by doubled-sided transfer tape, another adhesive, stitching or ultrasonic paper welding. Construction of an electrode subassembly in this manner secures and registers anode sub-assembly 170 and cathode layer 175 in respect of the periphery of the separator envelope so formed. The resulting electrode subassembly 227 is then presented for stacking in electrode assembly 225.

Yet another method of the present invention we have found for securing the separator to anode sub-assembly 170 is through the use of pressure bonding techniques. In such a method, separator layer 165 or 180 is pressed into a surface of anode sub-assembly 170 or anode layer 185 over a localized region thereof with sufficient force to rigidly affix the separator paper to anode sub-assembly 170, but not with such great force that a portion of underlying anode sub-assembly 170 is fractured. Other methods of securing all or portions of separator layer 165 or 180 to anode sub-assembly 170 or anode layer 185 include, but are not limited to, stitching, adhesive bonding and ultrasonic paper welding techniques.

Figure 7:
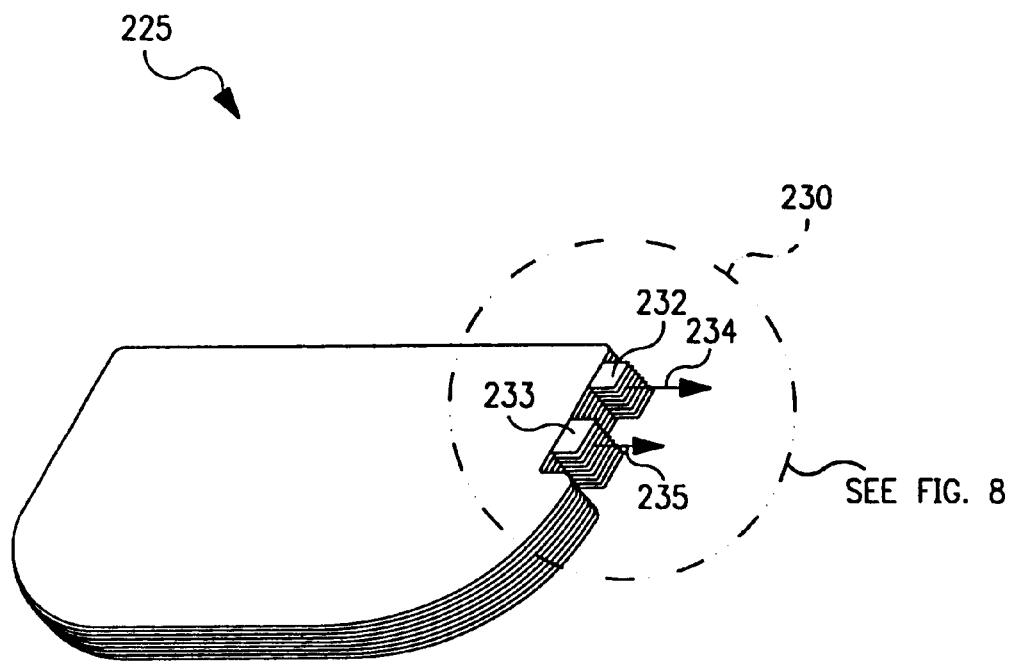
FIG. 7 shows a top perspective view of one embodiment of an electrode assembly of a capacitor of the present invention.
Figure 8:
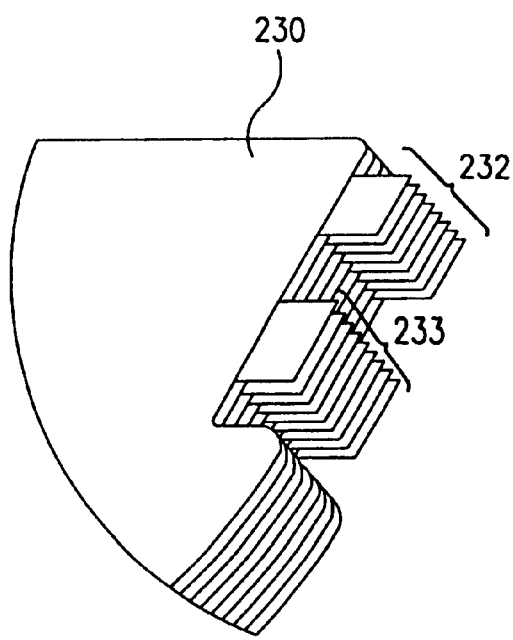
FIG. 8 shows an enlarged view of a portion of the electrode assembly shown in FIG. 7.

FIG. 7 shows a top perspective view of one embodiment of an electrode assembly of a capacitor of the present invention. FIG. 8 shows an enlarged view of a portion of the electrode assembly of FIG. 7. After wrapping electrode assembly 225 with outer wrap 115 and wrapping tape 245, interconnection of anode tabs 232 and cathode tabs 233 with their respective external terminals is most preferably made.

FIG. 9 shows an exploded top perspective view of one embodiment of a capacitor of the present invention employing the electrode assembly of FIGS. 6, 7 and 8 therein. This embodiment of the present invention includes anode feedthrough 120 and cathode feedthrough 125 most preferably having coiled basal portions 121 and 126, respectively. Feedthroughs 120 and 125 provide electrical feedthrough terminals for capacitor 265 and gather anode tabs 232 and cathode tabs 233 within basal portions 121 and 126 for electrical and mechanical interconnection.

Figure 10:
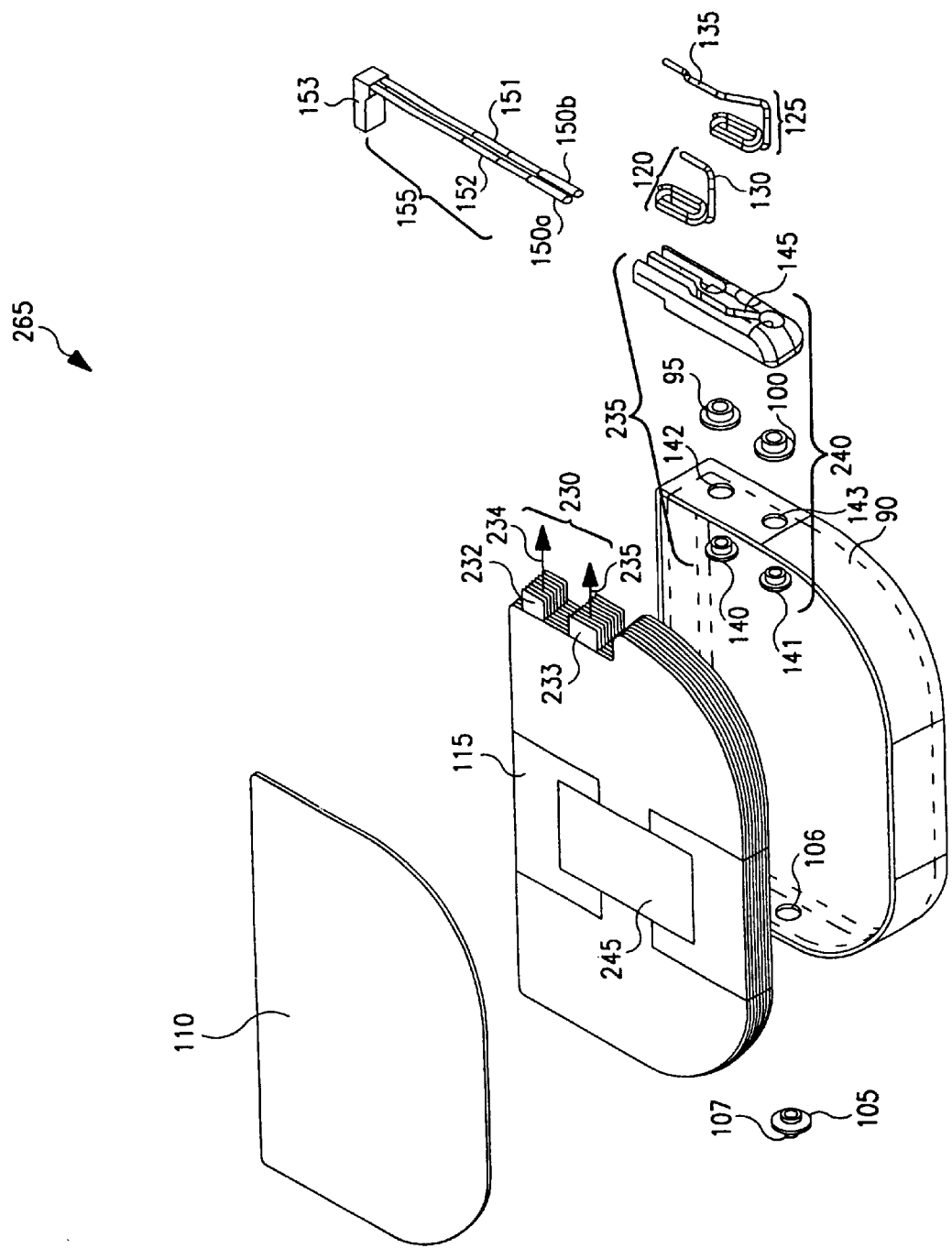
FIG. 10 shows an exploded top perspective view of the partially assembled capacitor of FIG. 9.
Figure 16:
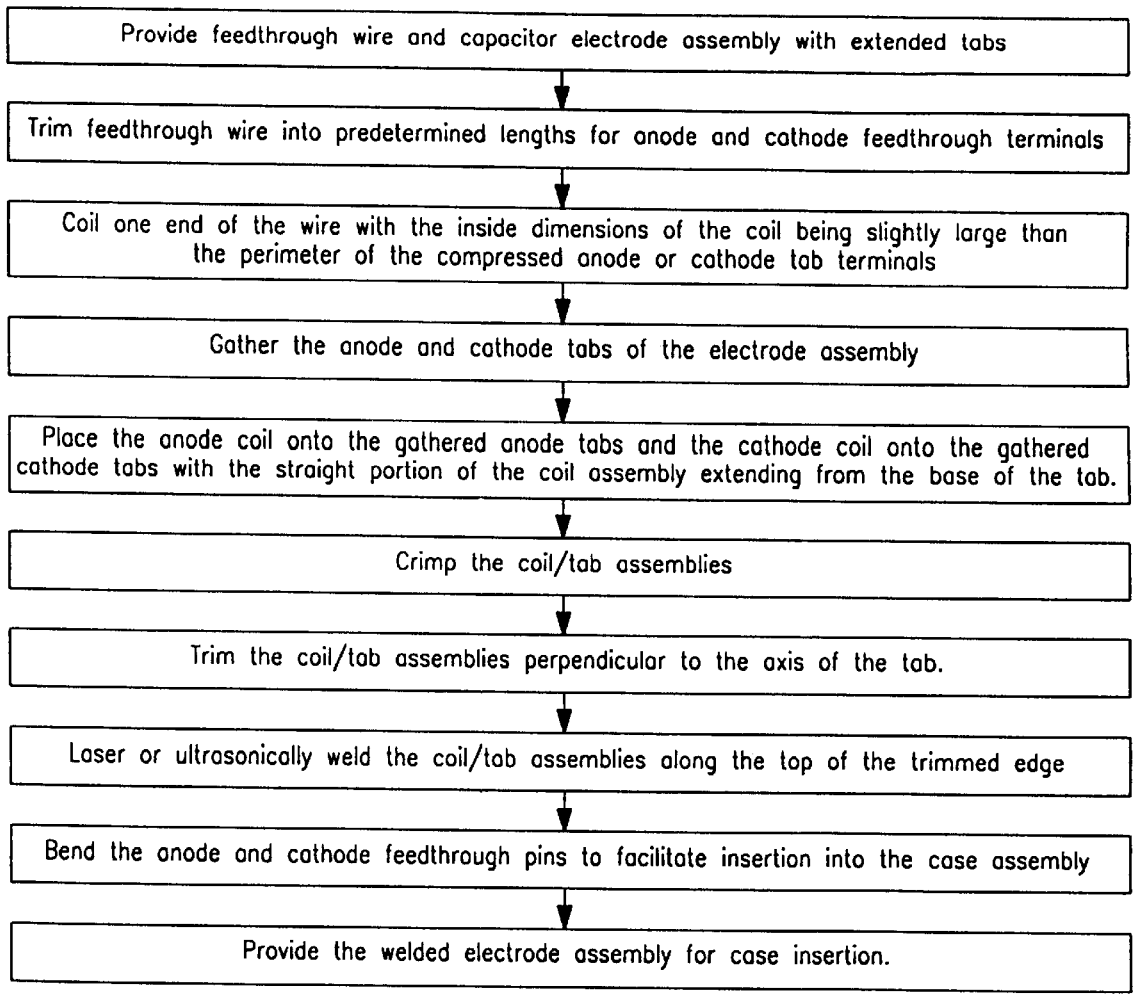
FIG. 16 shows a flow chart of one method of the present invention for making tab interconnections and feedthrough terminal connections of the present invention.

FIG. 16 shows a flow chart corresponding to one method of making tab interconnections and feedthrough terminal connections of the present invention. In such a method, feedthrough wire is first provided for construction of feedthroughs 120 and 125, as shown in FIGS. 9 and 10. In one embodiment of the present invention, a preferred feedthrough wire is aluminum having a purity greater than or equal to 99.99% and a diameter of 0.020 inches. Wire is trimmed to predetermined lengths for use in anode feedthrough 120 or cathode feedthrough 125. One end of the trimmed wire is coiled such that its inside diameter or dimension is slightly larger than the diameter or dimension required to encircle gathered anode tabs 232 or gathered cathode tabs 233.

Anode tabs 232 are next gathered, or brought together in a bundle by crimping, and inside diameter 131 of anode feedthrough coil assembly 120 is placed over anode tabs 232 such that anode feedthrough pin 130 extends outwardly away from the base of anode tabs 232. Similarly, cathode tabs 233 are gathered and inside diameter 136 of cathode feedthrough coil assembly 125 is placed over cathode tabs 233 such that cathode feedthrough pin 135 extends outwardly away from the base of cathode tab 233. Coiled basal portions 121 and 126 of anode and cathode feedthroughs 120 and 125 are then most preferably crimped onto anode and cathode tabs 232 and 233, followed by trimming the distal ends thereof, most preferably such that the crimps so formed are oriented substantially perpendicular to imaginary axes 234 and 235 of tabs 232 and 233. Trimming the distal ends may also, but less preferably, be accomplished at other non-perpendicular angles respecting imaginary axes 234 and 235.

In some methods of the present invention, a crimping force is applied to feedthrough coils 130 and 135 and tabs 232 and 233 throughout a subsequent preferred welding step. In one method of the present invention, it is preferred that the crimped anode and cathode feedthroughs be laser or ultrasonically welded along the top portion of the trimmed edge of the distal ends to anode and cathode tabs 232 and 233.

Following welding of feedthroughs 120 and 125 to anode tabs 232 and cathode tabs 233, respectively, pins 130 and 135 are bent to insertion through feedthrough holes 142 and 143 of case 90.

Many different embodiments of the feedthroughs, and means for connecting the feedthroughs, of the present invention to anode and cathode tabs exist other than those shown explicitly in the Figures. For example, feedthroughs of the present invention include within their scope embodiments comprising basal portions having open sides, forming "U" or "T" shapes in cross-section, forming a coil having a single turn of wire, forming a coil having three or more turns of wire, formed from flattened wire, or basal portions formed from crimping sleeves or layers of metal for connecting feedthrough pins 130 and 135 to anode and cathode tabs 232 and 233.

Figure 17:
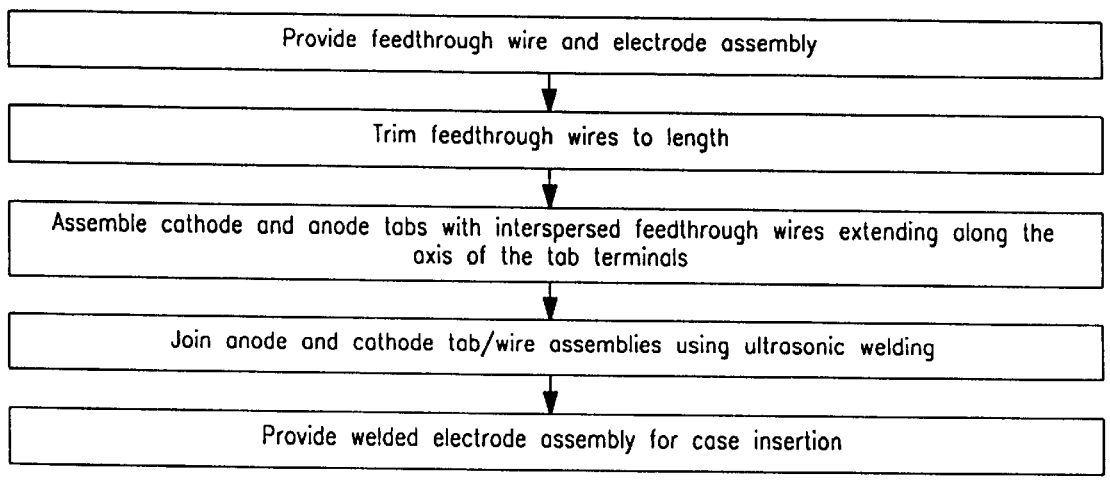
FIG. 17 shows a flow chart of one method of the present invention for making tab interconnections and feedthrough terminal connections of the present invention.

FIG. 17 shows a flow chart corresponding to one method of the present invention for making tab interconnections and feedthrough connections. In this method, anode feedthrough 120 and cathode feedthrough 125 have no coiled portions. Anode tabs 232 and cathode tabs 233 are gathered and trimmed, followed by the basal portions of anode and cathode feedthroughs 120 and 125 being placed propinquant to anode tabs 232 and cathode tabs 233, respectively. The basal portions of feedthroughs 120 and 125 are then joined to anode tabs 232 and cathode tabs 233, respectively, most preferably by ultrasonic welding means.

In yet another method of the present invention, the basal portions of feedthroughs 120 and 125 are flattened to facilitate welding to anode and cathode tabs 232 and 233. In still another method of the present invention, the basal portions of feedthrough pins 130 and 135 are formed such that they engage anode tabs 232 or cathode tabs 233 around the periphery of the tabs by means other than coiling. For example, basal portions 121 and 126 of feedthroughs 120 and 125 may be "flag shaped," and the flag portions thereof may be wrapped around tabs 232 and 233. In yet other methods of the present invention, feedthrough pins 130 and 135 may be attached to anode and cathode tabs 232 and 233 with resistance welds, cold welds, brazing, friction welds, or an additional feedthrough component such as a crimping sleeve may capture and join tabs 232 and 233 for providing electrical and mechanical connections thereto.

It has been discovered that the processes of forming electrical connections between tabs 232 and 233 and feedthrough coil assemblies 120 and 125 can introduce undesirable stress on tabs 176 and 195. The resultant strain induced in those tabs has further been found to manifest itself as tears in cathode layer 175 at the base of cathode tab 176, or as fractures in relatively low strength cold welds 205 or 210 within anode sub-assembly 170. One advantage of the coiled portions of feedthroughs 120 and 125 is that they can provide strain relief between feedthrough pins 130 and 135 and tabs 232 and 233. Thus, the strain relief features of feedthroughs 120 and 125 help minimize or eliminate undesirable stress in feedthrough connections.

The foregoing means for connecting multiple electrode tab elements to feedthroughs may also be employed in other energy storage devices such as batteries, electrochemical cells and cylindrically wound capacitors.

As employed in the specification and claims hereof, the term "laser welding" means, but is not necessarily limited to, a method of welding wherein coherent light beam processing is employed. Other means of coherent light beam processing falling within the scope of the method of the present invention include electron beam or laser welding methods (e.g., Nd:YAG, $CO_2$ processes) having hard or fiber optic beam delivery in pulsed, continuous, or q-switched modes. Still other welding means fall within the scope of the method of the present invention, such as micro metal inert gas welding and micro plasma welding processes.

Table 2 sets forth optimized, preferred processing parameters we have discovered under which various components of capacitor 265 are laser welded to one another. The parameters set forth in Table 2 correspond to those for a Model No. JK702H pulsed Nd:YAG laser welding system having hard optic beam delivery manufactured by Lumonics Laserdyne of Eden Prairie, Minnesota.

Table 3 sets forth a range of parameters under which the same type of laser welding system provides acceptable weld characteristics in accordance with other methods of the present invention.

TABLE 2

Optimized Nd:YAG Laser Welding Parameters

| Weld Type | Optimized Laser Welding Parameters* | | | | |
|---|---|---|---|---|---|
| | Energy per Pulse (Joules/pulse) | Pulse Frequency (Hertz) | Feed Rate (inches/min) | Pulse Width (msec) | Argon Cover Gas (SCFH) |
| Feedthrough Ferrule to Case Tack 1 | 13.5 | 4.5 | 3 | 5 | 35 |
| Feedthrough Ferrule to Case Weld | 9.75 | 20 | 2 | 4.5 | 35 |
| Fillport Ferrule to Case Tack 1 | 13.5 | 4.5 | 3 | 5 | 35 |
| Fillport Ferrule to Case Weld | 15 | 15 | 2 | 6 | 35 |
| Anode Feedthrough Tabs | 8 | 10 | 2 | 5 | 35 |
| Cathode Feedthrough Tabs | 4 | 10 | 2 | 5 | 35 |
| Cover to Case | 7.5 | 40 | 6 | 5.4 | 60 |
| Filltube Seal | 13.5 | 15 | 4 | 7 | 30 |

*Lumonics JK702H Nd:YAG laser having an initial beam diameter of approximately one inch passing through a final focusing lens with a 146 mm focal length (purchased having "160 mm lens", actual fine focal point measured was 146 mm) and a spot size at the joint surface of 0.022 inches. The cover gas was coaxial. It will be understood that variations respecting the manufacturer of the laser, beam delivery optics, the initial beam size, final focusing lens, spot size of the beam and the like fall within the scope of a method of the present invention.

TABLE 3

Generalized Nd:YAG Laser Welding Parameters

| Weld Type | Generalized Laser Welding Parameters* | | | | |
|---|---|---|---|---|---|
| | Energy per Pulse (Joules/pulse) | Pulse Frequency (Hertz) | Feed Rate (inches/min) | Pulse Width (msec) | Argon Cover Gas (SCFH) |
| Feedthrough Ferrule to Case | 2–15 | 3–30 | 1–5 | 3.5–8 | 30–60 |
| Fillport Ferrule to Case | 2–15 | 3–30 | 1–5 | 3.5–8 | 30–60 |
| FeedthroughTabs | 1–10 | 1–20 | 1–7 | 3.5–8 | 30–60 |
| Cover to Case | 5–25 | 10–40 | 1–7 | 3.5–8 | 30–60 |
| Filltube Seal | 8–20 | 5–20 | 1–10 | 3.5–8 | 30–60 |

*Lumonics JK702H Nd:YAG laser having an initial beam diameter of approximately one inch passing through a final focusing lens with a 146 mm focal length (purchased having "160 mm lens", actual fine focal point measured was 146 mm) and a spot size at the joint surface of 0.022 inches. The cover gas was coaxial. It will be understood that variations respecting the manufacturer of the laser, beam delivery optics, the initial beam size, final focusing lens, spot size of the beam and the like fall within the scope of a method of the present invention.

Figure 18:
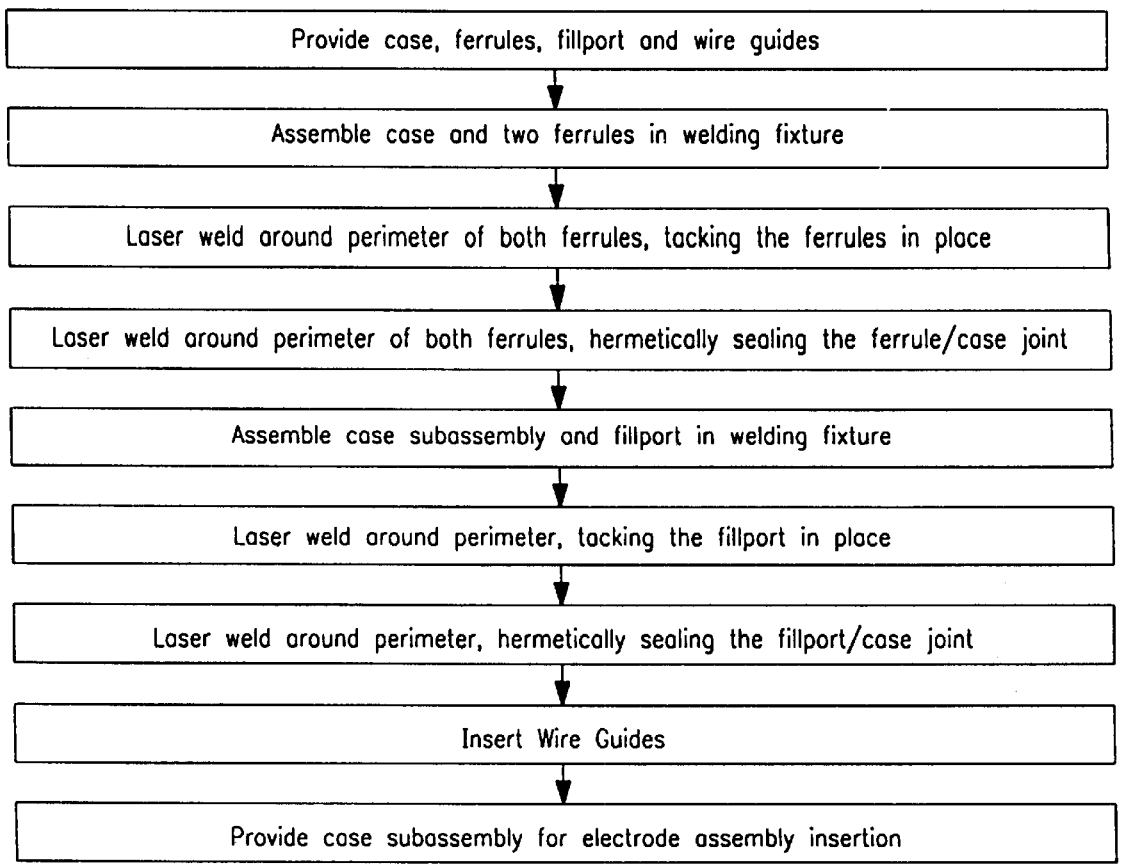
FIG. 18 shows a flow chart of one method of the present invention for making a case sub-assembly of the present invention.

FIG. 10 shows an exploded top perspective view of capacitor 265 of FIG. 9 in a partially assembled state. FIG. 18 shows a flow chart of one method of making case subassembly 108. Case 90, anode ferrule 95, cathode ferrule 100, and fill port ferrule 105 are first provided. Case 90 contains a means for accepting anode ferrule 95 therein, shown in FIGS. 9 and 10 as anode feedthrough ferrule hole 142. Case 90 further contains a means for accepting cathode ferrule 100, shown in FIGS. 9 and 10 as cathode feedthrough ferrule hole 143. Case 90 also includes a means for accepting fill port ferrule 105, shown in FIGS. 9 and 10 as fill port hole 106. In a preferred embodiment of the present invention, case 90 and cover 110 are formed of aluminum. In other embodiments of the present invention, case 90 or cover 110 may be formed of any other suitable corrosion-resistant metal such as titanium or stainless steel, or may alternatively be formed of a suitable plastic, polymeric material or ceramic.

Case 90, cover 110 and capacitor 265 of the present invention may additionally form a case negative capacitor (where can 90 and cover 110 are electrically connected to the cathode layers, and where can 90 and cover 110 are at the same electrical potential as the cathode layers, i.e., at negative potential), or a floating case capacitor (where can 90 and cover 110 are electrically connected neither to the cathode layers nor to the anode sub-assemblies, and where can 90 and cover 110 are at substantially no electrical potential or at an electrical potential that floats with respect to the respective potentials of the cathode layers and the anode sub-assemblies). In some embodiments of the present invention, case 90 or cover 110 may be formed of an electrically non-conductive material or substantially electrically non-conductive material such as a suitable plastic, polymeric or ceramic material.

Ferrules 95, 100 and 105 are most preferably welded to case 90 (or otherwise attached thereto such as by a suitable epoxy, adhesive, solder, glue or the like), and together comprise case subassembly 108. Radial flanges in anode ferrule 95 and cathode ferrule 100 provide a region for making a lap joint between the side wall of case 90 and around the perimeters of feedthrough ferrule holes 142 and 143. In preferred methods of the present invention, a circumferential laser weld is disposed in joint 93, and welding is carried out in two primary steps. First, a series of tack welds is made around the circumference of joint 93. The tack welds are most preferably made either by making adjoining, successive tack welds around the perimeter or by making a first tack weld at a first location along the perimeter, making a second weld diametrically opposed from the first weld along the perimeter, making a third weld adjacent to the first weld, making a fourth weld adjacent to the second weld, and so on. Finally, a final closing weld is made around the hole perimeter to hermetically seal tack welded joint 93.

Table 2 sets forth an optimized set of parameters under which anode ferrule 95 and cathode ferrule 100 are joined to case 90. Table 3 sets forth a range of general parameters under which the same laser welding system provides acceptable weld characteristics for joining anode ferrule 95 and cathode ferrule 100 to case 90.

Figure 20:
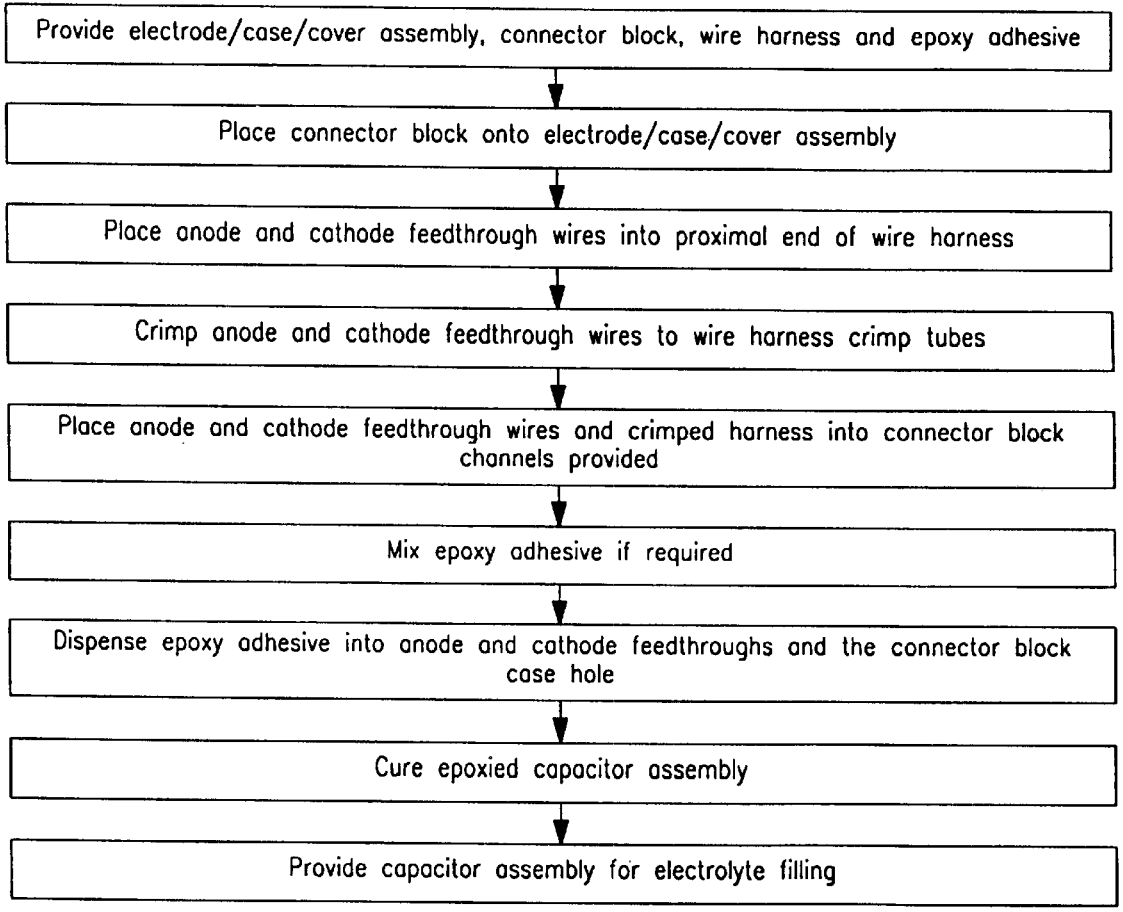
FIG. 20 shows a flow chart of one method of the present invention for sealing a feedthrough of the present invention.
Figure 21A:
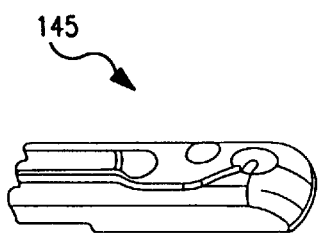
FIGS. 21(a) through 21(e) show perspective, top, cross-sectional, top and cross-sectional views, respectively, of one embodiment of a connector block of the present invention.
Figure 21B:
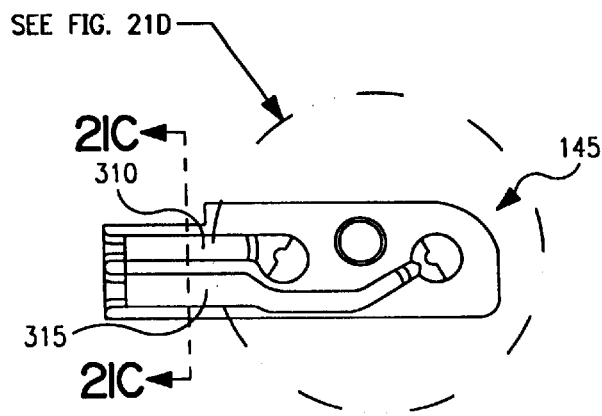
Figure 21D:
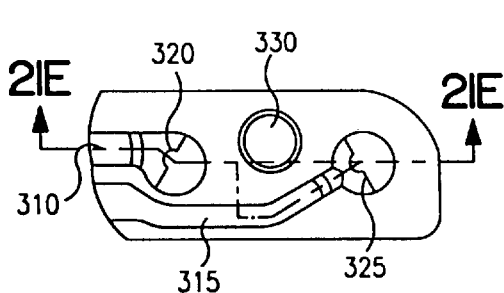
Figure 21C:
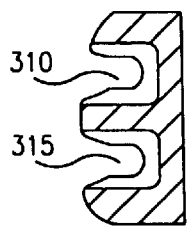
Figure 21E:
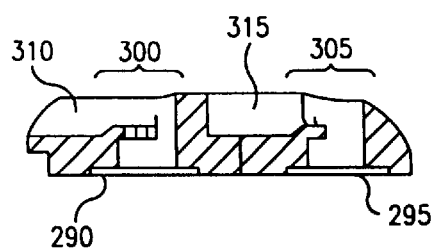

FIG. 18 shows steps for inserting anode wire guide 140 into the inside diameter of anode ferrule 95, and inserting cathode wire guide 141 into the inside diameter of cathode ferrule 100. Wire guides 140 and 141 center pins within the inside diameter of the ferrules to permit anode and cathode pins 130 and 135 to be electrically insulated from the inside surface of case 90, anode ferrule 95, and cathode ferrule 100. Wire guides 140 and 141 may themselves be electrically insulative, and electrical insulation of pins 130 and 135 from case 90 and other components is most preferably enhanced by means of potting adhesive 160. FIG. 20 shows further details concerning one method of the present invention for forming electrical insulation between pins 130 and 135 and anode ferrule 95 and cathode ferrule 100.

Wire guides 140 and 141 most preferably contain annular, ramped, or "snap-in" features formed integrally therein. Those features prevent wire guides 140 and 141 from being pushed out of their respective ferrules during handling, but are most preferably formed such that insertion of wire guides 140 and 141 in their corresponding ferrules may occur using forces sufficiently low so as not to damage case 90 or ferrules 95 or 100 during the inserting step.

Wire guides 140 and 141 may be formed from any of a wide variety of electrically insulative materials that are stable in the environment of an electrolytic capacitor. In one preferred embodiment of the present invention, the material from which wire guides 140 and 141 is made is an injection molded polysulfone known as AMOCO UDEL supplied by Amoco Performance Products of Atlanta, Georgia. In other embodiments of the present invention, wire guides 140 and 141 may be formed from other chemically resistant polymers such as fluoroplastics (e.g., ETFE, PTFE, ECTFE, PCTFE, FEP, PFA or PVDF), fluoroelastomers, polyesters, polyamides, polyethylenes, polypropylenes, polyacetals, polyetherketones, polyarylketones, polyether sulfones, polyphenyl sulfones, polysulfones, polyarylsulfones, polyetherimides, polyimides, poly(amide-imides), PVC, PVDC-PVC copolymers, CPVC, polyfurans, poly (phenylene sulfides), epoxy resins, silicone elastomers, nitrile rubbers, chloroprene polymers, chlorosulfonated rubbers, polysulfide rubbers, ethylene-polypropylene elastomers, butyl rubbers, polyacrylic rubbers, fiber-reinforced plastics, glass, ceramic and other suitable electrically insulative, chemically compatible materials.

As used in the specification and claims hereof, the foregoing acronyms have the following meanings: the acronym "ETFE" means poly(ethylene-co-tetrafluoroethylene); the acronym "PTFE" means polytetrafluoroethylene; the acronym "CTFE" means poly(ethylene-co-chlorotrifluoroethylene); the acronym "PCTFE" means polychlorotrifluoroethylene; the acronym "FEP" means fluorinated ethylene-propylene copolymer; the acronym "PFA" perfluoroalkoxy fluoropolymer; the acronym "PVDF" means polyvinylidene fluoride; the acronym "PVC" means polyvinyl chloride; the acronym "PVDC-PVC" means polyvinylidene chloride-polyvinyl chloride copolymer; and the acronym "CPVC" means chlorinated polyvinyl chloride.

Figure 11:
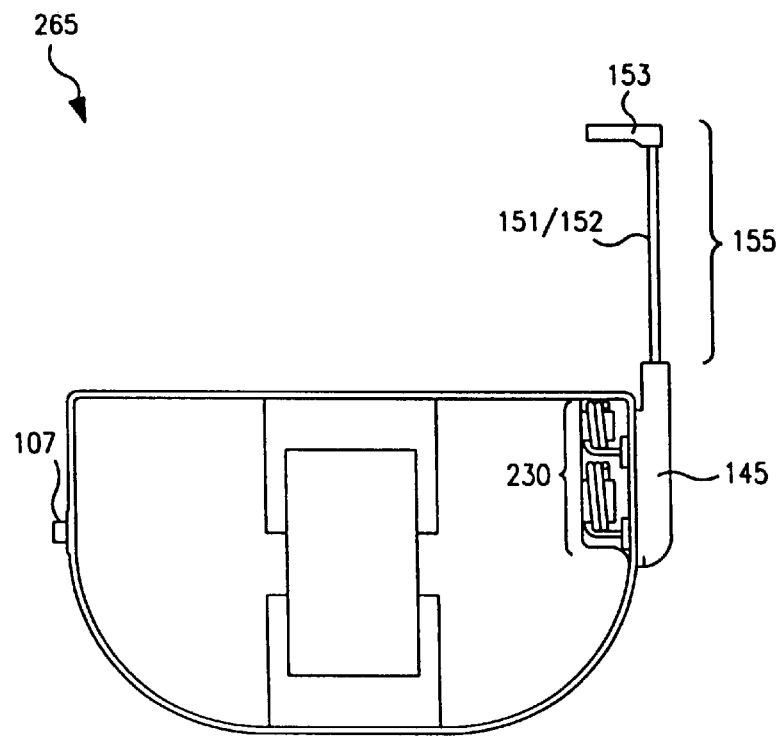
FIG. 11 shows a top view of one embodiment of a fully assembled capacitor of the present invention having no cover 110 disposed thereon.
Figure 12:
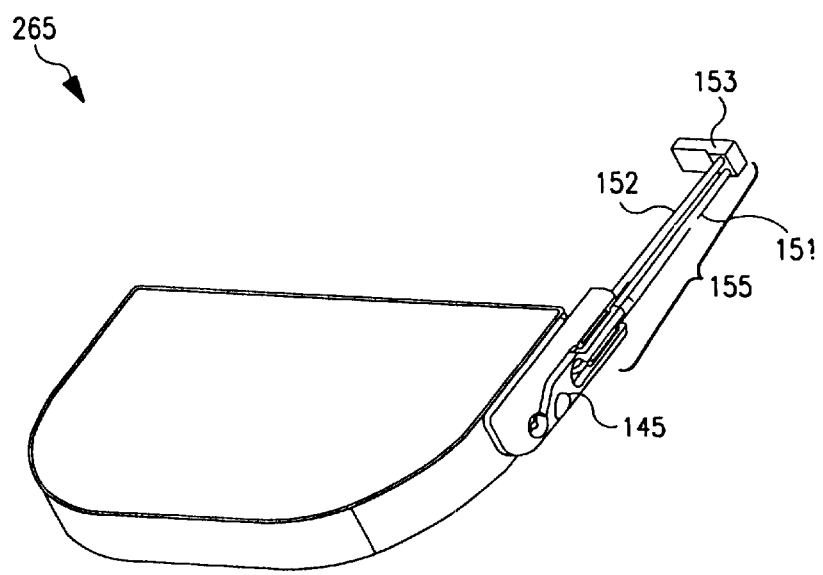
FIG. 12 shows a top perspective view of the capacitor of FIG. 11 having cover 110 disposed thereon.

FIG. 11 shows a top view of one embodiment of assembled capacitor 265 of the present invention with cover 110 not present. Electrode assembly 225 has been inserted into case subassembly 108 through wire guides 140 and 141. In one embodiment of the present invention, the headspace portion of electrode assembly 225 (referred to herein as headspace 230) is insulated from case 90 and cover 110. The means of the present invention by which headspace insulation may be provided include molded, thermally-formed, die cut, or mechanically formed insulating materials and means, where the materials and means are stable in the environment of an electrolytic capacitor. Suitable materials from which headspace insulators may be formed include all those listed hereinabove respecting materials for forming wire guides 140 and 141. Another means of providing headspace insulation is to wrap electrically insulative tape, similar to wrapping tape 245, around headspace 230 to prevent the anode or cathode terminals from contacting case 90 or cover 110.

Figure 26A:
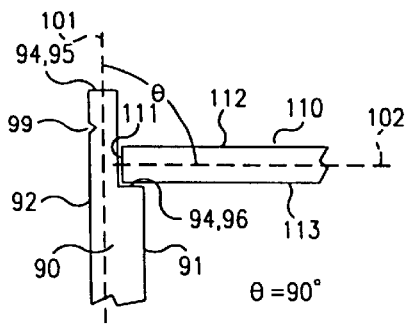
FIGS. 26(a) through 26(p) show various embodiments of the crimp and joint of the case and cover of the present invention.
Figure 26B:
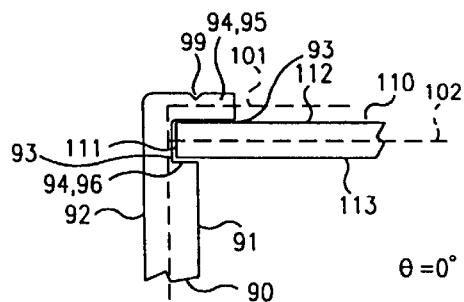
Figure 26C:
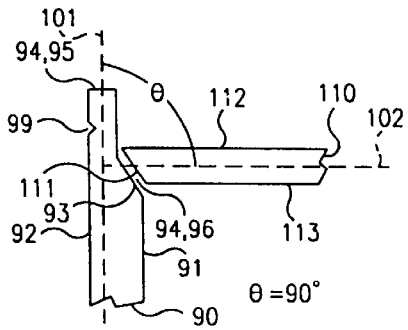
Figure 26D:
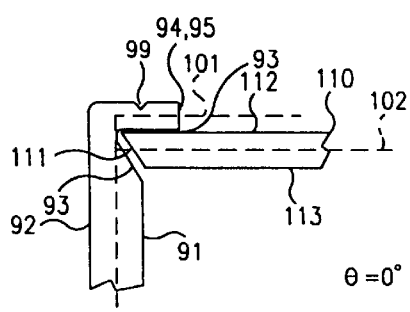
Figure 26E:
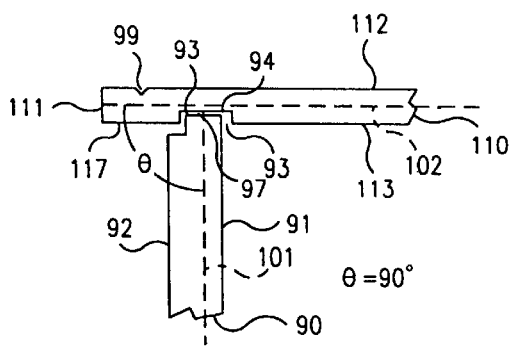
Figure 26F:
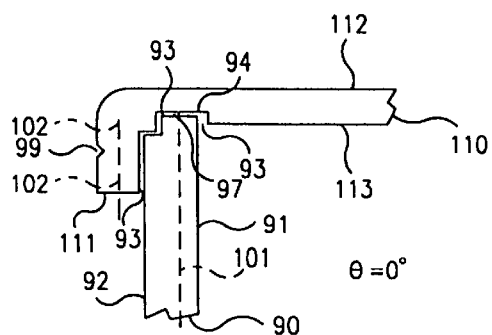
Figure 26G:
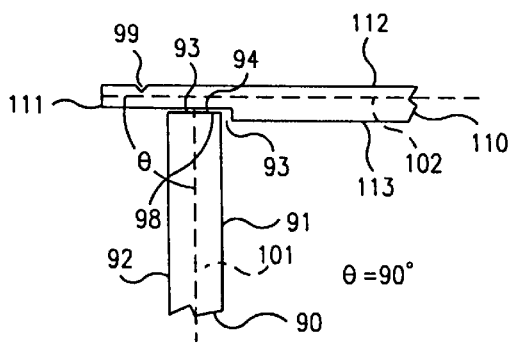
Figure 26H:
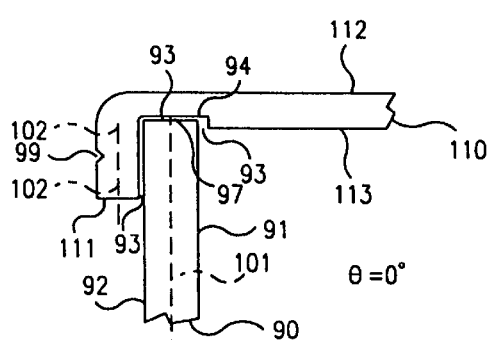
Figure 26I:
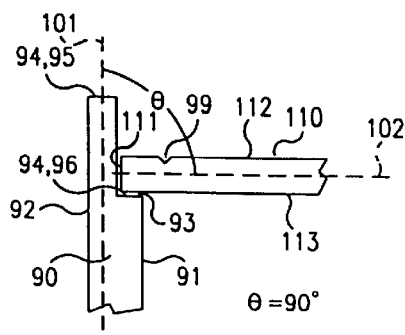
Figure 26J:
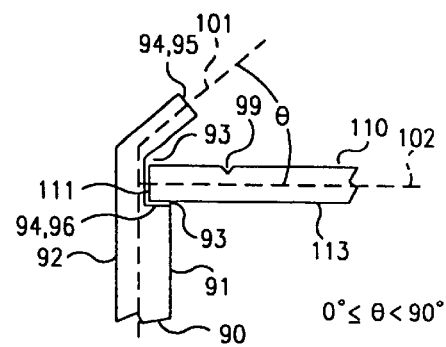
Figure 26K:
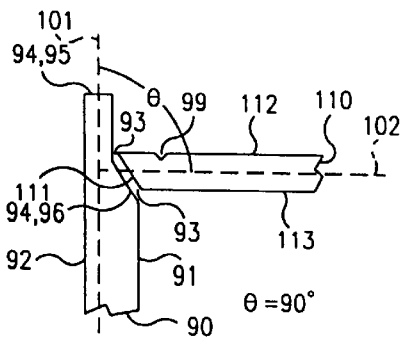
Figure 26L:
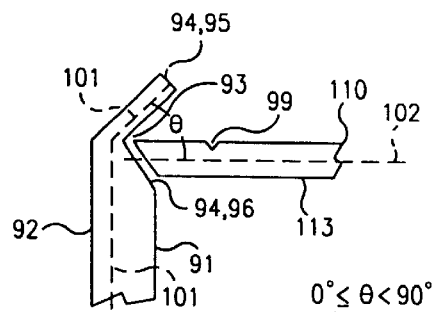
Figure 26M:
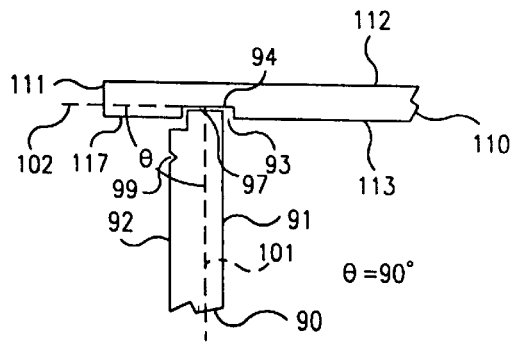
Figure 26N:
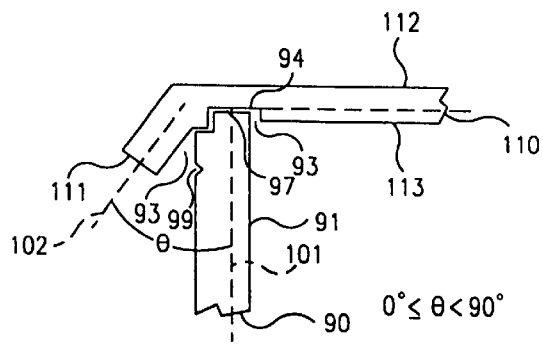
Figure 26O:
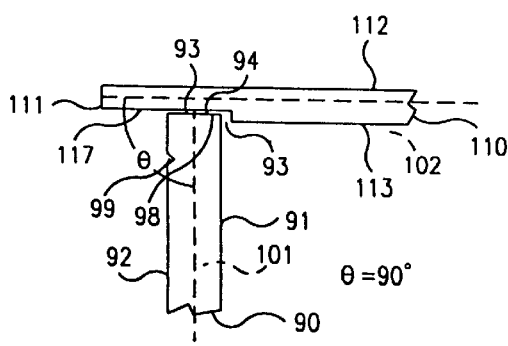
Figure 26P:
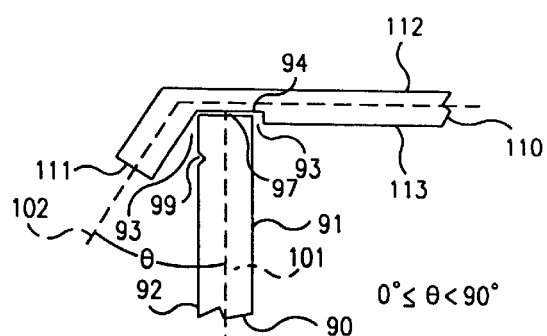

FIGS. 26(a) through 26(p) show different embodiments of joint 93 and the crimp of the present invention. Various types of crimp and joint configurations for joining the cover 110 to case 90 are illustrated in cross-section in those figures.

The inventors of the present invention have discovered that the particular structural configuration of joint 93 is of the utmost importance in respect of the suitable laser weldability thereof. More particularly, it has been discovered that joints for covers of prior art flat capacitors having metal cases and covers and conventional joint structures generally permit laser energy to enter the interior of capacitor 265 through the joints formed between the covers and cases thereof, thereby damaging or heating up components disposed inside case 90. Joints of the prior art which permit such undesired penetration of laser energy inside capacitor 265 were discovered to generally have a common feature: a joint geometry wherein a straight or substantially straight line of sight or portion existed or was disposed through the joint between the interior of the capacitor and the exterior of the capacitor. Joints having no such straight line of sight or portion through the joint between the exterior and interior of the capacitor were found to eliminate or at least diminish substantially the ill effects attending laser energy penetration to the interior of the capacitor.

In one embodiment of the present invention, case 90, cover 110, joint 93, upper edge 94, raised portion 95, stepped portion 96, groove 97, stepped portion 98 and outer edge 111 cooperate with one another to cause laser energy entering joint 93 from the exterior of capacitor 265 to be reflected or scattered to the outside of capacitor 265, and further to be contained or absorbed within joint 93 in such a manner that no or substantially no laser energy penetrates joint 93 and enters the interior of capacitor 265 while simultaneously forming a suitable weld in joint 93 between case 90 and cover 110. This absorption, containment, backscattering or reflecting of laser energy by joint 93 results at least partially from the multiple orientations of joint 93 as it wends its way from the exterior of capacitor 265 to the interior thereof. In other words, and as illustrated in FIGS. 26(a) through 26(p), joint 93 of the present invention has multiple portions that are bent, non-parallel or serpentine respecting one another.

In one method of the present invention for laser welding joint 93, an axis of a laser beam is directed inwardly along or parallel to the surfaces defining a first portion of joint 93 (e.g., parallel to imaginary axis 102 or imaginary axis 101, depending on the particular embodiment of the present invention at hand). Upon entering the first portion of joint 93 or a region propinquant thereto, the laser beam encounters at least a second portion of joint 93 defined by surfaces that are bent or not parallel respecting the surfaces defining the first portion of joint 93. As shown in FIGS. 26(e) through 26(h) and 26(m) through 26(p), joint 93 of the present invention may also have a third portion defined by surfaces that are bent or non-parallel respecting the surfaces defining the second portion of joint 93. Consequently, and providing appropriate parameters are selected by a user for operating the laser welding system of the present invention, no portion of the laser beam impinging upon the first portion of joint 93 may penetrate joint 93 sufficiently far such that the laser beam reaches the interior of capacitor 265 without first being absorbed, reflected or scattered.

In another method of the present invention for laser welding joint 93, an axis of a laser beam is directed inwardly along or parallel to the surfaces defining a second portion of joint 93 (e.g., parallel to imaginary axis 102 or imaginary axis 101, depending on the particular embodiment of the present invention at hand). Upon entering the second portion of joint 93 or a region propinquant thereto, the laser beam encounters at least a first or third portion of joint 93 defined by surfaces that are bent or not parallel respecting the surfaces defining the second portion of joint 93.

FIGS. 26(a) through 26(d) show a first embodiment of joint 93 and the crimp of the present invention, wherein case 90 has inner and outer sidewalls 91 and 92 extending upwardly from a flat planar base of case 90 to form an open end that terminates in upper edge 94 disposed between inner and outer sidewalls 91 and 92. Upper edge 94 most preferably comprises at least one stepped portion 96 and at least one raised portion 95. Substantially planar cover 110 seals the open end of the case, cover 110 having upper and lower surfaces 112 and 113, respectively, separated by outer edge 111. At least portions of outer edge 111 are shaped to engage at least one stepped portion 96 of upper edge 94 such that cover 110 self-registers on case 90 when cover 110 is disposed over the open end of case 90, outer edge 111 is aligned approximately upper edge 94, and cover 90 is placed thereon.

As shown in FIGS. 26(*a*) and 26(*c*), at least one raised portion 95 of upper edge 94 initially extends above upper surface 112 of cover 110 when at least portions of outer edge 111 are placed on and engage at least one stepped portion 96. As shown in FIGS. 26(*b*) and 26(*d*), at least one raised portion 95 is crimped or folded inwardly over or along upper surface 112 of cover 110 to form joint 93 after at least portions of outer edge 111 are placed on and engage the least one stepped portion 96. Next joint 93 is laser welded to hermetically seal cover 110 to case 90.

In the laser welding step, the laser beam may be directed substantially parallel to axes 101 and 102 of FIG. 26(*b*) to form a weld in the first or second portions of joint 93. Alternatively, the laser beam may be directed substantially parallel to axis 101 of FIG. 26(*a*) (i.e., substantially parallel to upstanding sidewalls 91 and 92) after raised portion 95 is crimped over cover 110 such that at least portions of raised portion 95 melt and thereby weld first, second, third or other portions of joint 93 closed. Our laser welding method invention includes within its scope laser welding steps where the laser beam is oriented in directions other than those set forth explicitly above.

In FIGS. 26(*a*) and 26(*c*), imaginary axes 101 and 102 are oriented at an angle theta of about 90 degrees respecting one another, where imaginary axis 101 defines the initial orientation of upper edge 94 and imaginary axis 102 defines the orientation of the plane within which cover 110 is disposed. In FIGS. 26(*b*) and 26(*d*), after upper edge 94 has been crimped or folded inwardly over or along upper surface, imaginary axis 101 is oriented at an angle theta of about 0 degrees respecting imaginary axis 102.

FIGS. 26(*e*) through 26(*f*) show a second embodiment of the crimp and joint 93 of the present invention, where case 90 has inner and outer sidewalls 91 and 92, respectively, extending upwardly from a flat planar base of case 90 to form an open end terminating in upper edge 94 disposed between inner and outer sidewalls 91 and 92. Substantially planar cover 110 seals the open end of case 90. Cover 110 comprises upper and lower surfaces 112 and 113, respectively, separated by outer edge 111. Lower surface 113 of cover 110 has disposed thereon at least one of groove 97 (see FIGS. 26(*e*) and 26(*f*) and stepped portion 98 (see FIGS. 26(*g*) and 26(*h*)). Groove 97 or stepped portion 98 is disposed radially inward from outer edge 111.

At least portions of groove 97 or stepped portion 98 are shaped to engage corresponding portions of upper edge 94 such that groove 97 or stepped portion 98, in combination with upper edge 94, cause cover 110 to self-register on upper edge 94 when cover 110 is disposed over the open end of case 90, groove 97 or stepped portion 98 is aligned approximately with upper edge 94, and cover 110 is placed on upper edge 94. Outer portions 117 of cover 110 extending between outer edge 111 and groove 97 or stepped portion 98 are crimped or folded downwardly over at least portions of outer sidewall 92 of case 90 to form joint 93 after cover 110 is placed on the open end of can 90. Joint 93 is laser welded to hermetically seal cover 110 to case 90.

In the laser welding step, the laser beam may be directed substantially parallel to axes 101 and 102 of FIG. 26(*f*) to form a weld in the first, second or other portions of joint 93. Alternatively, the laser beam may be directed substantially parallel to axis 102 of FIGS. 26(*e*) or 26(*g*) (i.e., substantially parallel to the plane forming cover 110) after outer portion of cover 110 is crimped over outer sidewall 92 such that at least portions of outer portions of cover 110 melt and thereby weld first, second, third or other portions of joint 93 closed. Our laser welding method invention includes within its scope laser welding steps where the laser beam is oriented in directions other than those set forth explicitly above.

In FIGS. 26(*e*) and 26(*g*), imaginary axes 101 and 102 are initially oriented at an angle theta of about 90 degrees respecting one another, where imaginary axis 101 defines the orientation of upper edge 94 and imaginary axis 102 defines the initial orientation of outer edge 111. In FIGS. 26(*f*) and 26(*h*), after outer edge 111 has been crimped or folded downwardly over at least portions of outer sidewall 92, imaginary axis 102 is oriented at an angle theta of about 0 degrees respecting imaginary axis 102.

FIGS. 26(*i*) through 26(*p*) show yet other embodiments of the crimp and joint of the present invention, where the angle theta defining the orientations of imaginary axes 101 and 102 respecting one another after upper edge 94 has been crimped or folded inwardly, or outer edge 111 has been crimped or folded downwardly, is greater than or equal to 0 degrees but less than 90 degrees. The embodiments of the present invention shown in FIGS. 26(*i*) through 26(*p*) have been discovered to be particularly efficacious for providing good access to joint 93 for a laser welding beam.

Note, however, that many variations of the particular cover, case and joint geometries disclosed explicitly herein are possible and fall within the scope of the apparatus and corresponding methods of the present invention. For example, the case and cover of the present invention may form two aluminum-containing half-cases having upwardly and downwardly extending sidewalls, the two half-cases forming two open ends that are subsequently laser welded together. Alternatively, the case and cover may form two substantially planar aluminum-containing members separated by a single or multiple sidewall members, the two planar members being laser welded to the intervening sidewall members.

FIGS. 26(*a*) through 26(*p*) also show registration marks or alignment features 99 disposed on case 90 or cover 110. Registration mark or alignment feature 99 is employed to establish a reference position in joint 93 for the welding apparatus after the case or cover has been crimped or folded, thereby ensuring precise position of the welding apparatus in respect of case 90, cover 110 and joint 93 when a weld is being formed in joint 93. It has been discovered that optimum results are obtained when registration mark 99 is disposed on upper surface 112 of cover 110.

Figure 19:
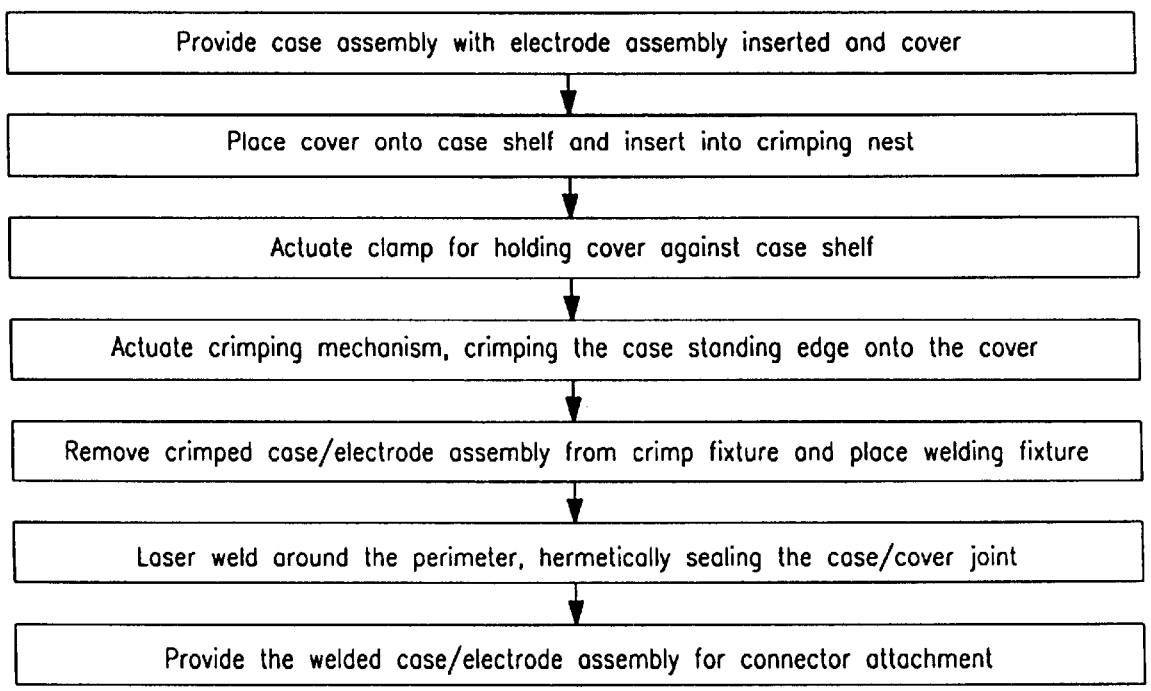
FIG. 19 shows a flow chart of one method of the present invention for sealing a case and cover of the present invention.

FIG. 19 shows a flow chart according to one method of the present invention for sealing case 90 and cover 110. Case subassembly 108 is provided with electrode assembly 225 inserted in case 90. Cover 110 is disposed atop upper edge 94 formed in case 90. In one method of the present invention, raised portion 95 of upper edge 94 extends about 0.014" above upper surface 112 of cover 110 when cover 110 is placed on upper edge 94. The assembly is placed within a crimping mechanism or nest, and a clamp is actuated to hold cover 110 against upper edge 94 and stepped portion 96. The crimping mechanism is actuated to crimp or fold over inwardly raised portion 95 onto, along or over upper surface 112 of cover 110.

In another method of the present invention, crimping of raised portion 95 is accomplished using a die cut to the shape of case 90 and further having angled or ramped sidewalls for engaging and pressing inwardly raised portion 95 over upper surface 112 of cover 110. A crimp may also be formed with a moving crimp apparatus that travels around the perimeter of case 90 while continuously crimping raised portion 95 over upper surface 112 of cover 110. The foregoing methods may be readily adapted to permit the crimping or folding of edge 111 of cover 110 downwardly over outer sidewall 92.

Crimping of raised portion 95 onto cover 110 or outer edge 111 onto sidewall 92 provides several advantages. First, laser welding of cover 110 to case 90 may be accomplished using relatively simple tooling, thereby resulting in short process times. Laser welding often provides a bottleneck in manufacturing process flow when components such as case 90 and cover 110 typically must be aligned precisely respecting one another. The elimination of such alignment steps during the laser welding process has been discovered to help eliminate manufacturing process bottlenecks. Folding or crimping raised portion 95 or outer edge 111 prevents a laser beam from entering the interior of capacitor 265. Instead, a laser beam is forced to couple with the material of case 90 and cover 110 to thereby induce melting. It was discovered that joints 93 not having crimps forming at least a portion thereof may permit a laser beam to damage components inside capacitor 265.

Another advantage of the crimped joint of the present invention is that the crimp provides additional metal in the weld zone. Aluminum, having a high thermal expansion coefficient, is sensitive to cracking upon rapid cooling from the high temperatures characteristic of welding processes. We discovered that the additional metal provided by the crimp decreases cracking sensitivity in joint 93. Joint 93 of the present invention is formed such that imaginary axes 101 and 102 are oriented at an angle theta respecting one another where theta is less than 90 degrees but greater than or equal to 0 degrees. It is notable that crimping of case 90 and cover 110 to one another helps registration of case 90 and cover 110 in respect of one another prior to the welding of at least portions of joint 93 being undertaken.

Crimped case 90 and cover 110 are next removed from the crimp fixture and placed in a welding fixture. A laser weld is made in joint 93 to hermetically seal case 90 to cover 110. Table 2 sets forth an optimized set of parameters under which the crimped case/cover joint may be sealed using a pulsed Nd:YAG laser welding system. Table 3 sets forth a generalized range of conditions under which the same laser welding system provides acceptable results.

In a preferred method of the present invention, machined, stamped, etched or otherwise-formed registration marks or alignment features 99 are disposed on cover 110 or case 90 to permit the relative positions of cover 110 and case 90 to be determined precisely for the laser welding step. Connectors are then attached to the welded case/electrode assembly.

FIG. 20 shows a flow chart according to one method of the present invention for sealing anode feedthrough portion 235 and cathode feedthrough portion 240 of capacitor 265. See also FIG. 10. FIGS. 9 through 12 show various embodiments of the sealing and connector attachments of the present invention in capacitor 265.

FIG. 21 shows several top, perspective and cross-sectional views according to one embodiment of capacitor connector block 145 of the present invention. In preferred embodiments of connector block 145 of the present invention, connector block 145 is disposed atop or otherwise connected to case 90 and/or cover 110, and has wire harness 155 and potting adhesive disposed therein.

A preferred material for forming connector block 145 is an injection molded polysulfone known as AMOCO UDEL supplied by Amoco Performance Products of Atlanta, Georgia. Connector block 140 may also be formed from any suitable chemically resistant thermoplastic polymers such as a flouroplastic (e.g., ETFE, PTFE, ECTFE, or PCTFE, FEP, PFA, PVDF), polyester, polyamide, polyethylene, polypropylene, polyacetal, polyarylketone, polyether sulfone, polyphenyl sulfone, polysulfone, polyarylsulfone, polyetherimides, polyimide, poly(amide-imide), PVC, PVDC-PVC copolymer, CPVC, polyfuran, poly(phenylene sulfide), epoxy resin and fiber reinforced plastic.

In one embodiment of the present invention, connector block 145 is placed on anode ferrule 95 and cathode ferrule 100 by guiding anode feedthrough pin 130 through connector block anode feedthrough hole 300, and then guiding cathode feedthrough pin 135 through connector block cathode feedthrough hole 305. Connector block 145 is next seated flush against the exterior surface of case 90. Anode feedthrough pin 130 is then inserted into anode crimp tube 150b of wire harness 155. Cathode feedthrough pin 135 is then inserted into cathode crimp tube 150a of wire harness 155. Crimp tubes 150a and 150b are then crimped to feedthrough pins 130 and 135.

In other embodiments of the present invention, electrical connections in connector block 145 may be established using techniques such as ultrasonic welding, resistance welding and laser welding. In such joining techniques, the joint geometry may also be a cross-wire weld between feedthrough wire 130 or 135 and harness wire 151 or 152. The present invention includes within its scope an embodiment having case 90 at cathode potential. In such an embodiment of the present invention, a separate cathode terminal connection is most preferably provided to permit additional design flexibility.

The distal or basal portions of crimp tubes 150a and 150b are crimped on insulated anode lead 151 and insulated cathode lead 152, respectively. Insulated leads 151 and 152 are likewise connected to terminal connector 153. Terminal connector 153 may most preferably be connected to electronics module 360. Standard methods of making aluminum electrolytic capacitors do not lend themselves readily to very small crimp connections, especially in miniaturized ICD designs. A method of the present invention permits small crimp connections an interconnection means to be formed, and further permits highly efficient packaging in PCD 10.

In the preferred method described above, connector block 145 and epoxy adhesive provide strain relief to feedthrough pins 130 and 135 and to the feedthrough wire crimp connections, and further provide an epoxy seal between pins 140 and 141, case 90 and ferrules 95 and 100. The crimp tubes may also serve as a connection point for device level assembly. Alternatively, the crimp tubes may be integrated within wire harness 155 prior to capacitor assembly. The wire harness may then serve as a means of routing capacitor electrical connections as desired in, for example, device level assembly steps.

In the embodiment of the present invention shown in FIG. 11, terminal connector 153 forms the female end of a slide contact. In another embodiment of the present invention, terminal connector 153 is connected to other modules by resistance spot welding, ultrasonic wire bonding, soldering, crimping, or other attachment means.

Referring again to FIG. 21, insulated anode lead 151 is inserted into anode block channel 310. Anode feedthrough pin 130 is centered in connector block anode feedthrough hole 300 by anode pin block guide 320. Insulated cathode lead 152 is inserted into cathode block channel 315. Cathode feedthrough pin 135 is centered in connector block cathode feedthrough hole 305 by cathode pin block guide 325. Centering of the pin through the ferrule assures that the pin does not contact the conducting wall of the ferrule, and also permits a more concentric epoxy seal to be formed around the pin. Centering of the pin may also be accomplished through means disposed in or on the epoxy dispensing or curing tools. Once the epoxy has hardened sufficiently, the centering tool is removed.

When employed, a potting adhesive is mixed and dispensed through connector block feedthrough holes 300 and 305 and block channels 310 and 315. Such an adhesive may also be dispensed through connector block hole 330 between connector block 145 and case 90. Adhesive bonding between block 145 and case 90 enhances structural stability of capacitor 265. The epoxy is then cured and capacitor 265 is filled with electrolyte.

The life of capacitor 265 may be appreciably shortened if solvent vapor or electrolyte fluid escapes from the interior of capacitor 265. Moreover, if capacitor 265 leaks electrolyte, the electrolyte may attack the circuits to which capacitor 265 is connected, or may even provide a conductive pathway between portions of that circuit. The present invention provides a beneficial means for preventing the escape of solvent and solvent vapor from capacitor 265. More particularly, capacitor 265 most preferably includes hermetic laser welded seams between joint case 90 and cover 110, and between ferrules 95,100, and 105 and case 90. Additionally, anode feedthrough portion 235 and cathode feedthrough portion 240 most preferably have an adhesive seal disposed therein for sealing the ferrule walls and the feedthrough wires.

The epoxy adhesive or potting material of the present invention is most preferably chemically resistant to the electrolyte employed in capacitor 265 and adheres well to surrounding surfaces. Adhesion promotion (such as by chemical deposition, etching, corona or plasma treatment of the polymeric wire guide of a polymeric case) may be employed to maximize the reliability of capacitor 265. In one preferred embodiment of the present invention, an aliphatic epoxy such as CIBA-Geigy Araldite 2014 is employed. Other suitable potting adhesives include chemically resistant thermoplastic hot melt materials such as polyamides, polyesters, polyurethanes, epoxies, and polyethylene-vinyl acetates, UV curable resins such as acrylates and methacrylates, and other thermosetting resins such as aliphatic and aromatic epoxies, silicones, polyamides, polyesters and polyurethanes. Many suitable potting adhesives may be thermally cured or cured with ultraviolet light. A focused IR procedure may be employed in some instances to minimize cure time and localize heat.

Since hermeticity is desirable in feedthrough assemblies of the present invention, the method by which the feedthrough seals are made should be predictable, uniform, reliable and produce high-quality hermetic seals. In a preferred method of the present invention, an epoxy adhesive is employed which has few or no voids and cracks and completely or substantially completely adheres to the surrounding pin, ferrule wall and wire guide components. Filling of the ferrule hole with sealing adhesive may be accomplished in several ways, depending largely on the viscosity of the pofting agent selected. A balance in viscosity characteristics of the sealing adhesive has been found to be desirable. More particularly, it is desired that the sealing adhesive be thin enough to fill without voids forming and to wet the surface, yet thick enough not to escape around or through the wire guide. The potting adhesive may be B-staged and inserted as a plug; likewise a hot melt adhesive may be applied in similar fashion. Subsequent heating completes curing of the sealing adhesive. In a preferred method of the present invention, CIBA Geigy Araldite 2014 epoxy is mixed with a static mix tube and dispensed within 45 minutes. The assembly is cured in an oven for 30 minutes at 90 degrees Celsius.

In another embodiment of the present invention, connector block 145, ferrules 95 and 100, and wire guides 140 and 141 are formed from a single molded component formed of a suitable chemically resistant thermoplastic or thermoset material that is sealed to case 90 using a potting adhesive. Channels or voids may be included in the basal portions of connector block 145 to permit potting adhesive to flow between those basal portions and case 90. Such a seal between the case and connector block 145 may replace the aforementioned laser welded seal between the ferrule and the case. Such a sealing method eliminates the requirement for several components and removes several processing steps, leading perhaps to significant manufacturing cost reductions.

Referring again to FIG. 13, capacitor 265 is filled with electrolyte. The electrolyte may be any suitable liquid electrolyte for high voltage electrolytic capacitors. In a preferred embodiment of the present invention, the electrolyte is an ethylene glycol based electrolyte having an adipic acid solute. It is contemplated in the present invention that other electrolytes suitable for use in high voltage capacitors may also be employed.

In accordance with a preferred method of the present invention, capacitor 265 is filled with a suitable liquid electrolyte via fill port tube 107 in multiple vacuum impregnation cycles. The capacitor and the electrolyte are placed in a vacuum chamber with fill port tube 107 connected to the electrolyte by a temporary tube. Multiple vacuum impregnation cycles are then performed at pressures exceeding the vapor pressure of the electrolyte. In a less preferred method of the present invention, capacitor 265 is filled with electrolyte by immersing capacitor 265 in the electrolyte or by vacuum-filling capacitor 265 with a metered filling machine. Note, however, that a single vacuum impregnation cycle falls within the scope of at least one method of the present invention.

Fill port tube 107 of the present invention provides a means for filling capacitor 265. In preferred embodiments of the present invention, fill port tube 107 includes helium leak verification capabilities and easy sealing characteristics. The hermeticity of capacitor 265 is preferably measured using a helium leak test. A helium leak testing apparatus forms a seal around the tube of fill port tube 107. The testing apparatus then pulls a vacuum on the interior of sealed capacitor 265, and the gas pulled from the interior of capacitor 265 is directed past a tuned mass spectrometer. Next, the exterior of capacitor 265 is exposed to helium gas, and the leak rate for helium through the materials and joints within capacitor 265 is determined by the mass spectrometer. This measure of leaktightness or hermeticity provides a means of assuring the quality of the joints being made.

In another embodiment of the present invention, "bombing" or filling of the interior of capacitor 265 with helium gas is accomplished immediately prior to sealing of fill port ferrule 105. The exterior of sealed capacitor 265 is then monitored under vacuum conditions with a tuned mass spectrometer to determine the rate of helium leakage past the materials and joints of capacitor 265.

Once capacitor 265 is filled with electrolyte, it is preferred that an aging process be undertaken. Aging is generally accomplished by applying a current through the capacitor terminals and gradually raising the voltage across those terminals from zero to the peak aging voltage of the capacitor (usually between about 360 and about 390 Volts DC). Once the aging voltage is attained, capacitor 265 is held at that voltage until the leakage current stabilizes at an acceptably low value. It is preferred that capacitor 265 be aged until a voltage of about 370 Volts is attained during a current limiting process.

In one preferred method of the present invention, the aging process is carried out with the voltage set at 370 Volts and the current limited to about 1.5 mA (for capacitor 265 having a capacitance of 214 microfarads). We have also found that it is beneficial to increase the temperature of the aging system at higher voltages. In one preferred method of the present invention, the temperature is increased to about 70 degrees Celsius when the voltage reaches 230 Volts. After aging to 370 Volts, the capacitors are most preferably permitted to continue aging with the voltage held at 370 Volts until the leakage current decreases to a predetermined value, a predetermined time at 370 Volts has elapsed, or until a predetermined rate of decrease in leakage current has been obtained.

Figure 22:
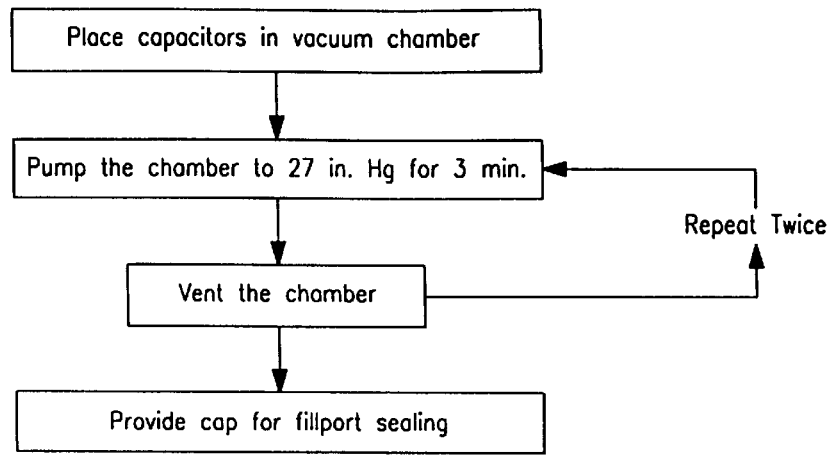
FIG. 22 shows a flow chart of one method of the present invention for vacuum treating an aged capacitor of the present invention.

Following aging, post aging vacuum treatment or filling of the capacitor contributes to significant improvements in capacitance and equivalent series resistance (ESR). FIG. 22 shows a flow chart describing one method of vacuum treating the aged capacitor. The aged capacitor is placed inside a vacuum chamber and held at 27 inches of mercury for three minutes. The chamber is vented and then held at 27 inches of mercury for three minutes for two additional cycles. The capacitor is then provided for fill port sealing.

Figure 23:
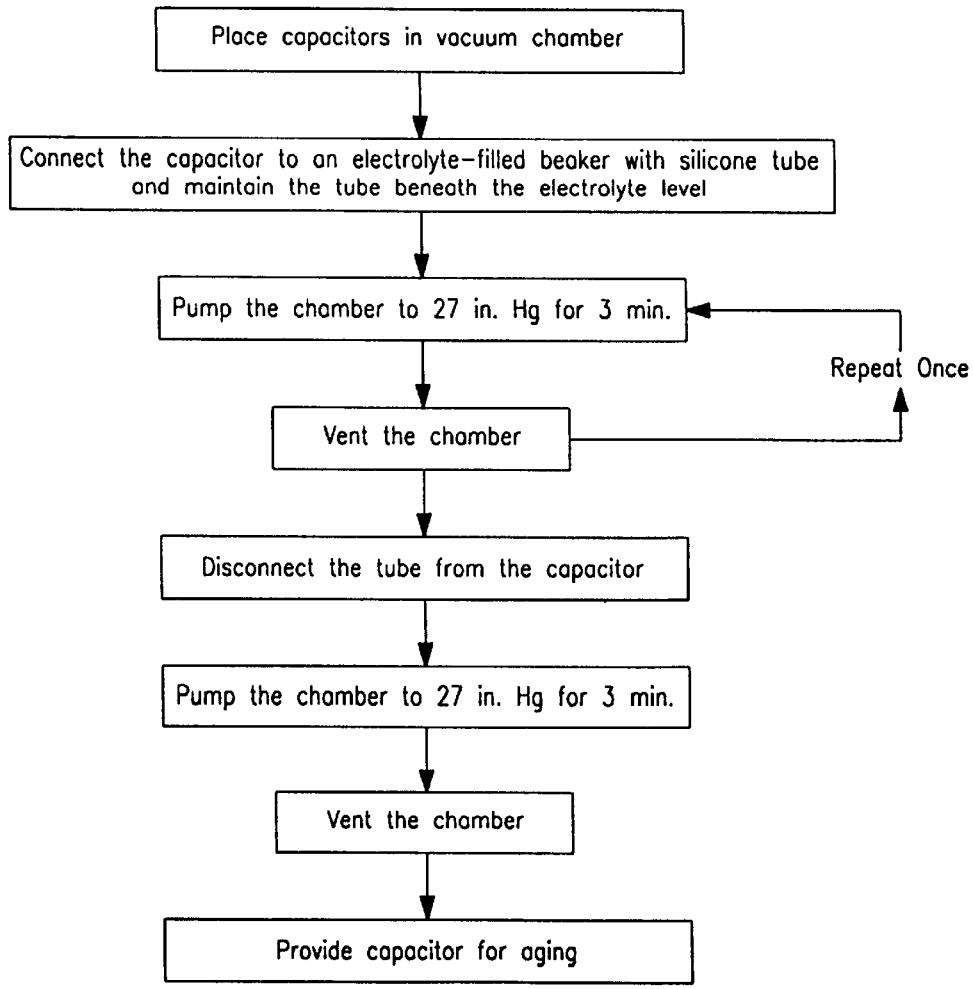
FIG. 23 shows a flow chart of one method of the present invention for refilling an aged capacitor of the present invention.

FIG. 23 shows a flow chart describing a preferred method for a vacuum refilling operation after aging. Aged capacitor 265 is placed inside a vacuum chamber, a temporary fill tube connected to fill port tube 107 being immersed in electrolyte. The chamber is then held at 27 inches of mercury for three minutes and vented. This step is repeated once with the temporary tube in the electrolyte and a second time with the temporary tube out of the electrolyte. The third cycle is intended to draw excess electrolyte from capacitor 265. Fillport ferrule tube 107 is now ready for sealing.

Figure 24:
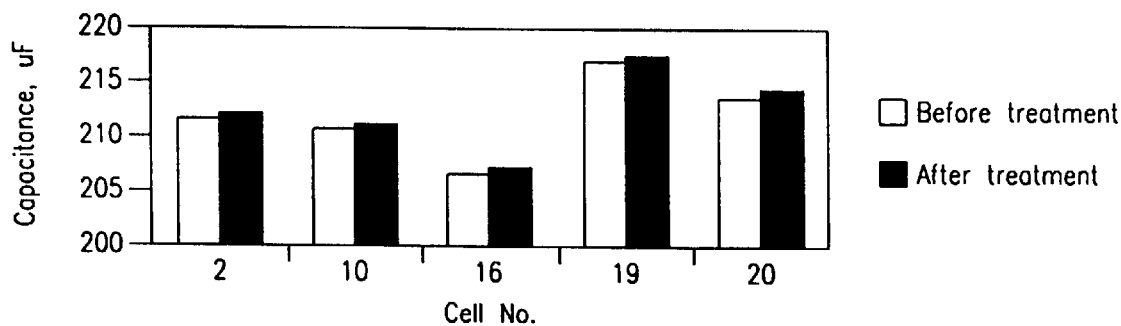
FIG. 24 shows comparative capacitance data for prior art capacitors and capacitors made according to the methods of FIGS. 22 and 23.
Figure 25:
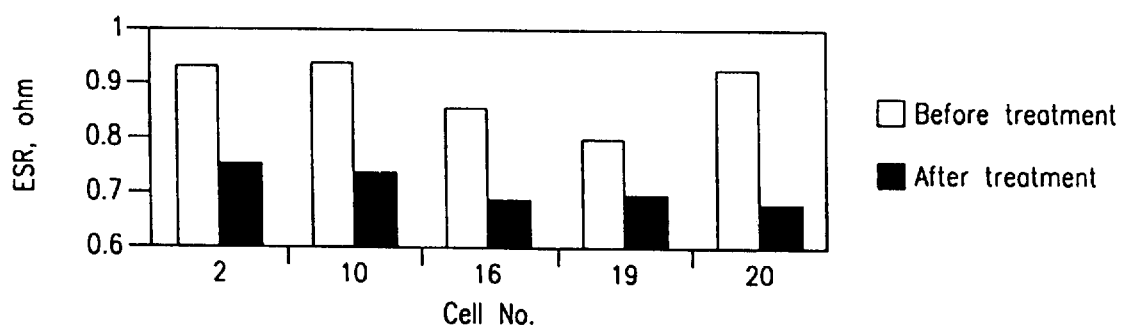
FIG. 25 shows comparative equivalent series resistance (ESR) data for prior art capacitors and capacitors made according to the methods of FIGS. 22 and 23.

FIG. 24 is a graph showing the increase in capacitance of five capacitors following the vacuum refilling operation of FIG. 23. The noted increase in capacitance is on the order of about 1 to about 2 microfarads (~0.3%). FIG. 25 is a graph showing the decrease in ESR of the same five capacitors after the vacuum refilling operation of FIG. 23. The noted decrease in ESR is on the order of about 0.2 ohms (~20%). The vacuum treatments are believed to remove entrapped gas that evolves during aging and refilling, and are also believed to replace electrolyte lost during aging, thereby permitting the microstructural pores of the anode and separator layers to be substantially fully filled and saturated with electrolyte. Excess electrolyte may also be removed through vacuum cycling with the fill tube pointing downwardly.

After vacuum refilling, distal end 106 of fill port tube 107 is most preferably crimped shut mechanically by pliers or other suitable means such as compression rollers or welding. The crimped or closed joint so formed is next most preferably trimmed with side cutter metal shears or in a metal die, and sealed. It is an advantage of the present invention that the fill port thereof may be closed and sealed quickly at minimum cost without any requirement for additional high tolerance, expensive piece parts or components for sealing fill tube 197.

Sealing of fill port tube 107 is most preferably accomplished using joining techniques such as ultrasonic welding, cold welding or laser welding. See, for example, Tables 2 and 3. Sealing of fill port tube 107 may also be accomplished by glueing, epoxying, or any other suitable means. For example, fill port tube 107 may be sealed by inserting a compression-fit spherical ball into a corresponding spherical recess disposed inside fill port tube 107 or ferrule 105. The ball is most preferably formed from a metal, plastic or ceramic material that is stable in the capacitor electrolyte. Dimensional control of the fill port tube or ferrule inside diameter in respect of the diameter of the ball is critical to controlling the quality of the seal being made. Ideally, the ball fits in the inside diameter in as tight an interference fit as possible without damaging the fill port ferrule weld or deforming case 90 to any significant extent. The "ball" need not conform to a spherical geometry, and may be a fitting that is cylindrically, conically or otherwise-shaped.

Still another method for sealing fill port ferrule 105 is to integrate a hydrogen permeable membrane seal into or propinquant to fill port ferrule 105 that does not permit electrolyte components to escape through fill port tube 107 but that does permit hydrogen gas evolved through charge and discharge of capacitor 265 to escape from the interior thereof. By sealing fill port tube 107 with a barrier having sufficient chemical resistance, but that is selective to hydrogen gas (such as some silicones, polyphenylene oxides, cellulose acetates and triacetates and polysulfones), no electrolyte is lost. Several potting adhesives (such as epoxy or silicone) have the foregoing chemical resistance and hydrogen permeability properties and thus are suitable for use in the present invention. Those adhesives most preferably seal feedthroughs while permitting hydrogen gas to escape from otherwise hermetically sealed capacitor 265.

In yet another embodiment of the present invention, the seal of fill port tube 107 is be a simple adhesive strip disposed over distal end 106 of fill port tube 107, similar to the types of seals employed in commercial ethylene glycol coolant canisters.

Figure 28A:
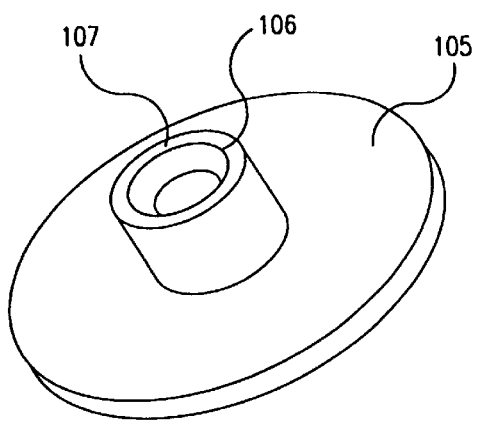
FIGS. 28(a) through 28(c) show various views of a liquid electrolyte fill port ferrule tube and fill port ferrule of the present invention.
Figure 28B:
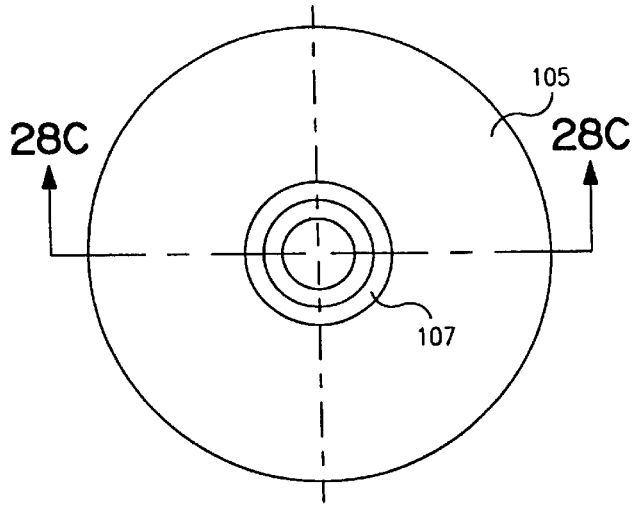
Figure 28C:
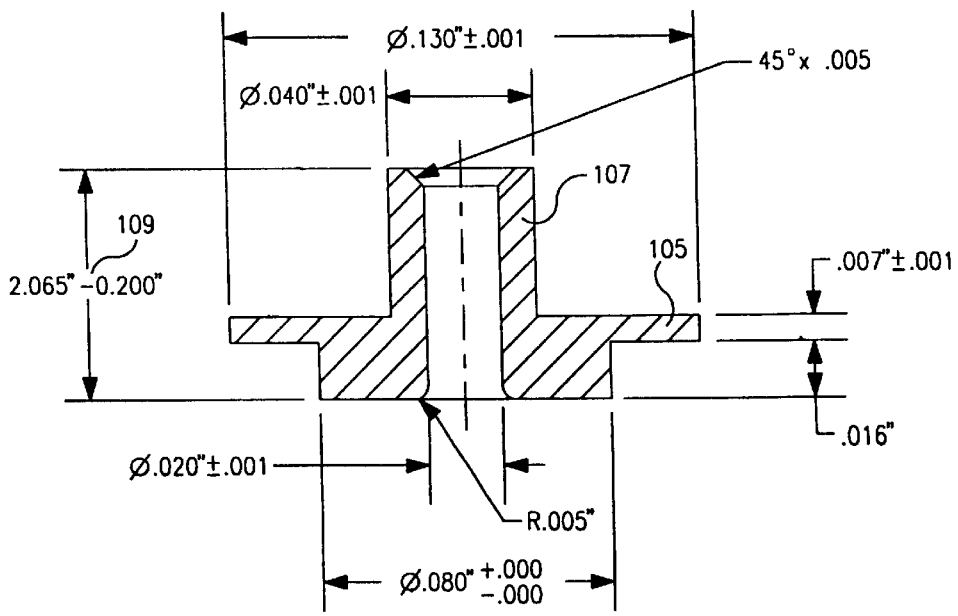

It is preferred that fill port ferrule 105 and fill port tube 107 form a single integrated piece of metal, although components 105 and 107 may form separate non-integral components and may further be formed of materials other than metal, such as ceramic or plastic. Fill port ferrule 105 fits within and is sealingly engaged to an opening disposed in the sidewall of case 90 or in cover 110. Additionally, height 109 of fill port tube 107 shown in FIG. 28(c) is most preferably about 0.200 inches with respect to the embodiment of capacitor 265 shown in the drawings hereof, although other heights 109 are contemplated in the present invention such as 0.065 inches, 0.300 inches, and so on.

It is preferred that height 109 be sufficiently great to accommodate a fitting of a helium leaktightness testing apparatus, the fitting being fitted in sealing engagement over the fill tube. It is preferred that an O-ring be disposed between the fitting and the fill tube as a vacuum of about 50 Tor is pulled on the interior of capacitor 265. Helium gas is then emitted about and around capacitor 265, cover 110, case 90, joint 93 between cover 110 and case 90, connector block 145, ferrule 105, tube 107 and other components while the helium leaktightness testing apparatus tests gas and molecules evacuated from the interior of capacitor 265 for the presence of helium gas which has leaked from the exterior of capacitor 265 into the interior thereof.

A tuned mass spectrometer is most preferably included in the helium leaktightness testing apparatus. The spectrometer is sensitive to the presence of helium atoms or molecules. An example of such an apparatus is a LEYBOLD INFICON Model No. UL-200 Helium Leaktester manufactured in East Syracuse, N.Y. An O-ring having a leaktightness rating of about $1\times10^{-9}$ cm$^3$/sec. is most preferably employed in conjunction with the fill tube and the fitting of the leaktightness testing apparatus. A typical fail point specification for the leaktightness testing apparatus when employed with the capacitor of the present invention is about $1\times10^{-9}$ cm$^3$/sec.

Figure 27A:
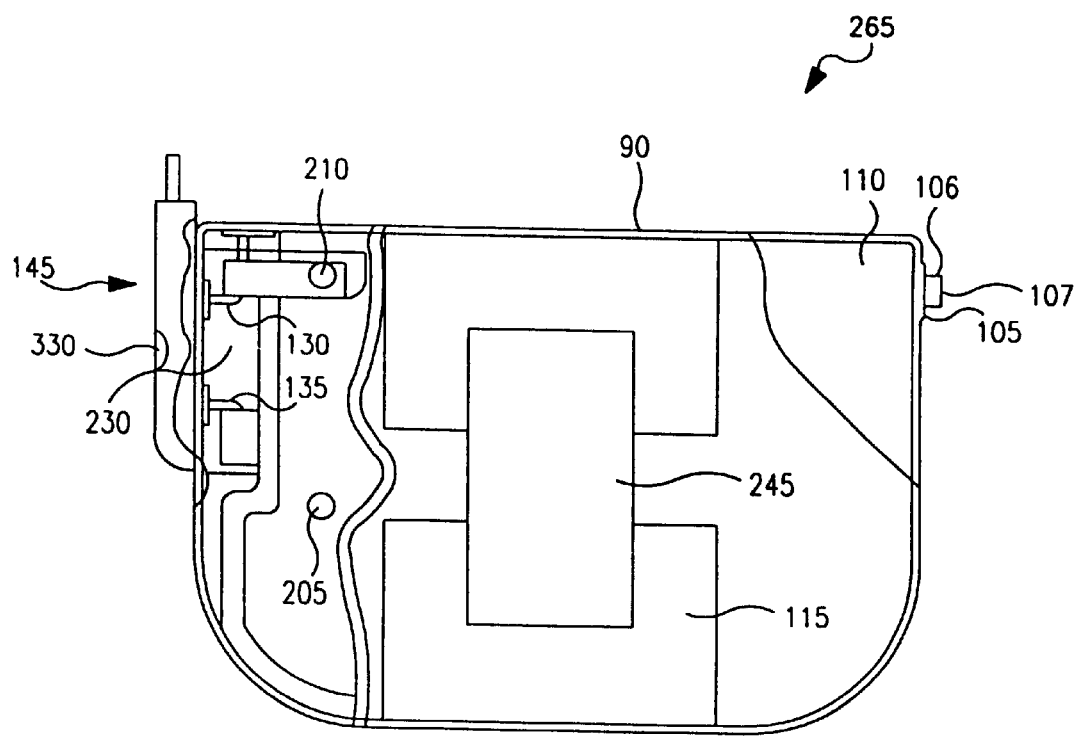
FIG. 27(a) shows a top view of a capacitor of the present invention with a portion of its cover removed.
Figure 27B:
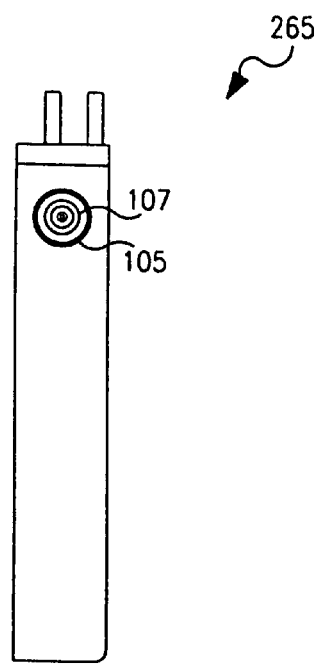
FIG. 27(b) shows an end view of the capacitor of FIG. 27(a)

FIG. 27(a) shows a top view of capacitor 265 with a portion of cover 90 removed and a portion of electrode assembly 225 exposed therewithin. Fill port ferrule tube 107 projects outwardly from an end of case 90 from fill port ferrule 105. FIG. 27(b) shows an end view of capacitor 265 of FIG. 27(a), and a corresponding end view of fill port tube 107 and fill port ferrule 105. FIGS. 28(a) through 28(c) show various views of one embodiment of liquid electrolyte fill port tube 107 and fill port ferrule 105 of the present invention.

In another embodiment of fill port tube 107 of the present invention, case 90 is formed of a suitable metal, and a fill port tube 107 is extruded from, punched in or otherwise integrally formed in a sidewall or other portion of case 90. Such a design eliminates the need for fill port ferrule 105 disposed in a wall or surface of case 90. For example, a tapered punch may be employed to initially punch a small diameter hole in a sidewall of case 90, followed by causing the punch to travel through the hole, causing metal from sidewall 90 to be extruded outwardly from the sidewall, and forming an outwardly projecting cylindrically or otherwise shaped fill port tube 107.

Once sealed, the capacitor is electrically tested. Applications in implantable defibrillators may require two capacitors to be connected in series. In this case an insulator is provided by a two sided adhesive being disposed between the capacitors. Two capacitors are joined along opposing faces with the insulator/adhesive strip disposed therebetween. The pair of capacitors is then provided for assembly in PCD 10. See FIGS. 3(a) through 3(h).

The scope of the present invention is not limited to defibrillation or cardioversion applications, or to applications where a human heart is defibrillated, but includes similar applications in other mammalians and mammalian organs. Those of ordinary skill will now appreciate that the method and device of the present invention are not limited to aluminum electrolytic capacitors for implantable medical devices, but extend to non-aluminum or partially-aluminum electrolytic capacitors for implantable medical devices, as well as to methods and corresponding capacitors and power sources for non-implantable medical devices and for electronic devices generally.

Additionally, although only a few exemplary embodiments of the present invention have been described in detail above, those skilled in the art will appreciate readily that many modifications are possible in the exemplary embodiments without materially departing from the novel teachings and advantages of the invention. Accordingly, all such modifications are intended to be included within the scope of the present invention as defined in the following claims.

The preceding specific embodiments are illustrative of the practice of the invention. It is to be understood, therefore, that other expedients known to those skilled in the art or disclosed herein, may be employed without departing from the invention or the scope of the appended claims.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

All patents and printed publications disclosed hereinabove are hereby incorporated by reference herein into the specification hereof, each in its respective entirety.

We claim:
1. An hermetically sealed implantable medical device, comprising:
  (a) an hermetically sealed housing;
  (b) an energy source disposed within the housing;
  (c) a substantially flat electrolytic capacitor connected to the energy source and disposed within the housing, the capacitor comprising:
    (1) at least one flat cathode layer formed of cathode foil and having a first perimeter of a first overall length, the cathode layer having top and bottom surfaces and at least a first cathode means for connecting projecting from the first perimeter at a first predetermined perimeter location;
    (2) a plurality of flat anode layers formed of anode foil, the plurality of anode layers forming an anode subassembly having top and bottom surfaces, at least one of the plurality of anode layers being a first anode layer having a second perimeter of a second overall length and at least a second anode means for connecting projecting from the second perimeter at a second predetermined perimeter location;
    (3) at least a first separator layer formed of separator material, the first separator layer defining a third perimeter having a third physical dimension;
    (4) a first cathode feedthrough means for connecting to the first cathode connecting means, the first cathode feedthrough means having a cathode feedthrough pin extending therefrom;
    (5) a second anode feedthrough means for connecting to the second anode connecting means, the second anode feedthrough means having an anode feedthrough pin extending therefrom;
    (6) a case having sidewalls extending upwardly from a flat planar base to form an open end;
  wherein the at least one cathode layer, the plurality of anode layers and the first separator layer are vertically stacked to form an electrode assembly such that the first separator layer is disposed between the at least one cathode layer and the anode sub-assembly, the first cathode connecting means is aligned with a first predetermined registration position in the electrode assembly, the second anode connecting means is aligned with a second predetermined registration position in the electrode assembly, the first cathode feedthrough connecting means is connected to the first cathode connecting means, the second anode connecting means is connected to the second anode connecting means, and the cover is sealingly disposed over the open end of the case.

2. The implantable medical device of claim 1, further comprising a second cathode layer formed of cathode foil and having a third perimeter, and a second separator layer formed of separator material, the second cathode layer having top and bottom surfaces and at least a third cathode means for connecting projecting from the third perimeter at a third predetermined perimeter location, the second cathode layer and the second separator layer being included within the electrode assembly such that the second separator layer is disposed between the anode sub-assembly and the second cathode layer, the first cathode connecting means and the third cathode connecting means being vertically aligned such that the first predetermined registration location of the electrode assembly coincides vertically with the third predetermined registration location of the electrode assembly, the first cathode feedthrough connecting means being connected to the first cathode connecting means and the third cathode connecting means.

3. The implantable medical device of claim 1, further comprising a third separator layer formed of separator material and a second anode sub-assembly having top and bottom surfaces and comprising a plurality of anode layers formed of anode foil, at least one of the plurality of anode layers of the second anode sub-assembly being a fourth anode layer having a fourth perimeter, at least a fourth anode means for connecting projecting from the fourth perimeter at a fourth predetermined perimeter location, vertically stacking the second anode sub-assembly and the third separator layer in the stacked electrode assembly such that the third separator later is disposed between the at least one cathode layer and the second anode sub-assembly, and vertically aligning the second anode means for connecting and the fourth anode means for connecting such that the second predetermined registration location of the electrode assembly coincides vertically with the fourth predetermined registration location of the electrode assembly, the second anode feedthrough connecting means being connected to the second anode connecting means and the fourth anode connecting means.

4. The implantable medical device of claim 1, wherein the first cathode feedthrough means for connecting to the first cathode connecting means is a proximal end of the cathode feedthrough pin, the proximal end of the cathode feedthrough pin being coiled around the first cathode connecting means.

5. The implantable medical device of claim 1, wherein the first anode feedthrough means for connecting to the first anode connecting means is a proximal end of the anode feedthrough pin, the proximal end of the anode feedthrough pin being coiled around the first anode connecting means.

6. The implantable medical device of claim 1, wherein the first cathode feedthrough means for connecting to the first cathode connecting means is selected from the group consisting of a crimp, a cold weld, a laser weld, an ultrasonic weld and a resistance weld.

7. The implantable medical device of claim 1, wherein the first anode feedthrough means for connecting to the first anode connecting means is selected from the group consisting of a crimp, a cold weld, a laser weld, an ultrasonic weld and a resistance weld.

8. The implantable medical device of claim 1, wherein the first cathode feedthrough means for connecting to the first cathode connecting means further comprises an intermediate strain relief component disposed between the proximal end of the first cathode feedthrough means for connecting to the first cathode connecting means and the cathode feedthrough pin.

9. The implantable medical device of claim 1, wherein the first anode feedthrough means for connecting to the first anode connecting means further comprises an intermediate strain relief component disposed between the proximal end of the first anode feedthrough means for connecting to the first anode connecting means and the anode feedthrough pin.

10. The device of claim 1, wherein the cathode layer is formed from aluminum cathode foil.

11. The implantable medical device of claim 1, wherein the anode layers are formed of through-etched aluminum anode foil.

12. The implantable medical device of claim 1, wherein each anode layer has a specific capacitance selected from the group consisting of at least about 0.3 microfarads/cm$^2$, at least about 0.5 microfarads/cm$^2$, and at least about 0.8 microfarads/cm$^2$.

13. The implantable medical device of claim 1, wherein each anode layer has a thickness selected from the group consisting of from about 20 micrometers to about 300 micrometers, from about 40 micrometers to about 200 micrometers, from about 60 micrometers to about 150 micrometers, and from about 70 micrometers to about 140 micrometers.

14. The implantable medical device of claim 1, wherein the cathode layer is formed from a highly etched cathode foil.

15. The implantable medical device of claim 1, wherein the cathode layer is formed from a aluminum cathode foil having a specific capacitance selected from the group consisting of at least about 100 microfarads/cm$^2$, at least about 200 microfarads/cm$^2$, at least about 250 microfarads/cm$^2$, and at least about 300 microfaradslcm$^2$.

16. The implantable medical device of claim 1, wherein the cathode layer is formed from aluminum foil having a thickness selected from the group consisting of from about 10 micrometers to about 200 micrometers, from about 15 micrometers to about 150 micrometers, from about 20 micrometers to about 100 micrometers, from about 25 micrometers to about 75 micrometers, and about 30 micrometers.

17. The implantable medical device of claim 1, wherein the anode sub-assembly comprises a plurality of non-notched anode layers and at least to one notched anode layer.

18. The implantable medical device of claim 1, wherein the anode layers in the anode sub-assembly are cold welded together.

19. The implantable medical device of claim 1, wherein at the first separator layer is pressure bonded to the anode sub-assembly.

20. The implantable medical device of claim 1, wherein the top and bottom surfaces of the anode sub-assembly are covered by the first separator layer and a second separator layer.

21. The implantable medical device of claim 1, wherein the separator layer has a perimeter extending beyond the perimeter of the anode sub-assembly.

22. The implantable medical device of claim 1, wherein the implantable medical device is selected from the group consisting of a PCD, an AID, an ICD, a defibrillator, an implantable pulse generator and a pacemaker.

23. The implantable medical device claim 1, wherein the energy source is selected from the group consisting of a battery, an electrochemical cell, a primary electrochemical cell, a secondary or rechargeable electrochemical cell, an electrochemical cell comprising a lithium-containing anode, an electrochemical cell comprising a silver vanadium oxide-containing cathode, an electrochemical cell comprising a $(CF_n)_x$-containing cathode, an electrochemical cell comprising a cathode containing a mixture of silver vanadium oxide and $(CF_n)_x$, a spirally wound electrochemical cell, an electrochemical cell having a plurality of plate-shaped electrodes, and an electrochemical cell having at least one serpentine electrode disposed therewithin.

24. The implantable medical device of claim 1, wherein the plurality of anode layers is connected electrically to the case.

25. The implantable medical device of claim 1, wherein the at least one cathode layer is electrically connected to the case.

26. The implantable medical device of claim 1, wherein the case is connected electrically to neither the at least one cathode layer nor to the plurality of anode layers.

27. The implantable medical device of claim 1, wherein the electrode assembly is secured by means for securing the electrode assembly to prevent electrode assembly movement or shifting.

28. The implantable medical device of claim 27, wherein the means for securing the electrode assembly comprises an electrode wrap and corresponding adhesive strip.

29. The implantable medical device of claim 1, wherein at least portions of the first separator layer are secured together at the periphery thereof to corresponding portions of a second separator layer by at least one of crimping, stitching, adhesive bonding, ultrasonic paper welding or direct pressure bonding.

30. The implantable medical device of claim 1, wherein the case is formed of aluminum or aluminum alloy.

31. The implantable medical device of claim 1, wherein the at least one cathode layer has no holes for registration disposed therethrough.

32. The implantable medical device of claim 1, wherein the plurality of flat anode layers have no holes for registration disposed therethrough.

33. A method of making an hermetically sealed implantable medical device, comprising the steps of
   (a) providing a housing for the implantable medical device;
   (b) providing and disposing an energy source within the housing;
   (c) providing components for a substantially flat electrolytic capacitor, comprising the steps of:
      (i) providing at least one flat cathode layer formed of cathode foil and having a first perimeter of a first overall length, the cathode layer having top and bottom surfaces and at least a first cathode means for connecting projecting from the first perimeter at a first predetermined perimeter location;
      (ii) providing a plurality of flat anode layers formed of anode foil, the plurality of anode layers forming an anode sub-assembly having top and bottom surfaces, at least one of the plurality of anode layers being a first anode layer having a second perimeter of a second overall length and at least a second anode means for connecting projecting from the second perimeter at a second predetermined perimeter location;
      (iii) providing at least a first separator layer formed of separator material, the first separator layer defining a third perimeter having a third physical dimension;
      (iv) providing a first cathode feedthrough means for connecting to the first cathode connecting means, the first cathode feedthrough means having a cathode feedthrough pin extending therefrom;
      (v) providing a second anode feedthrough means for connecting to the second anode connecting means, the second anode feedthrough means having an anode feedthrough pin extending therefrom;
      (vi) providing a case having sidewalls extending upwardly from a flat planar base to form an open end;
      (vii) providing a cover for sealing the open end of the case;
   (d) assembling the components of the capacitor such that the at least one cathode layer, the plurality of anode layers and the first separator layer are vertically stacked in the case, the first separator layer being disposed between the at least one cathode layer and the anode sub-assembly, the first cathode connecting means being aligned with a first predetermined registration position in the electrode assembly, the second anode connecting means being aligned with a second predetermined registration position in the electrode assembly, the first cathode feedthrough connecting means being connected to the first cathode connecting means, the second anode connecting means being connected to the second anode connecting means, the cover being sealingly disposed over the open end of the case;
   (e) placing the capacitor in the housing and connecting the energy source to the capacitor, and
   (f) hermetically sealing the housing of the implantable medical device.

34. The method of claim 33, wherein the steps of providing and assembling capacitor components further comprise the steps of providing a second cathode layer formed of cathode foil and having a third perimeter, and providing a second separator layer formed of separator material, the second cathode layer having top and bottom surfaces and at least a third cathode means for connecting projecting from the third perimeter at a third predetermined perimeter location, vertically stacking the second cathode layer and the second separator in the electrode assembly such that the second separator layer is disposed between the anode sub-assembly and the second cathode layer, vertically aligning the first cathode connecting means and the third cathode connecting such that the first predetermined registration location of the electrode assembly coincides vertically with the third predetermined registration location of the electrode assembly, and connecting the first cathode feedthrough connecting means to the first cathode connecting means and the third cathode connecting means.

35. The method of claim 33, wherein the steps of providing and assembling capacitor components further comprise the steps of providing a second separator layer formed of separator material, providing a second anode sub-assembly having top and bottom surfaces and comprising a plurality of anode layers formed of anode foil, at least one of the plurality of anode layers of the second anode sub-assembly being a fourth anode layer having a fourth perimeter, providing at least a fourth anode means for connecting projecting from the fourth perimeter at a fourth predetermined perimeter location, vertically stacking the second anode sub-assembly and the second separator layer in the stacked electrode assembly such that the second separator layer is disposed between the at least one cathode layer and the second anode sub-assembly, and vertically aligning the second anode means for connecting and the fourth anode means for connecting such that the second predetermined registration location of the electrode assembly coincides vertically with the fourth predetermined registration location of the electrode assembly, and connecting the second anode feedthrough connecting means to the second anode connecting means and the fourth anode connecting means.

36. The method of claim 33, wherein the assembling step further comprises the step of connecting the first cathode feedthrough connecting means to the first cathode connecting means by placing a coiled proximal end of the cathode feedthrough pin over and around the first cathode connecting means.

37. The method of claim 33, wherein the assembling step further comprises the step of connecting the first anode feedthrough connecting means to the first anode connecting means by placing a coiled proximal end of the anode feedthrough pin over and around the first anode connecting means.

38. The method of claim 33, wherein the assembling step further comprises the step of connecting the first cathode feedthrough means to the first cathode connecting means by crimping, cold welding, laser welding, ultrasonically welding or resistance welding the feedthrough means to the connecting means.

39. The method of claim 33, wherein the assembling step further comprises the step of connecting the first anode feedthrough means to the first anode connecting means by crimping, cold welding, laser welding, ultrasonically welding or resistance welding the feedthrough means to the connecting means.

40. The method of claim 33, wherein the assembling step further comprises placing and connecting an intermediate strain relief component between a proximal end of the first cathode feedthrough means for connecting to the first cathode connecting means and the cathode feedthrough pin.

41. The method of claim 33, wherein the assembling step further comprises placing and connecting an intermediate strain relief component between a proximal end of the first anode feedthrough means for connecting to the first anode connecting means and the anode feedthrough pin.

42. The method of claim 33, wherein the cathode layer providing step is preceded by a step of forming the at least one cathode layer to have no holes for registration disposed therethrough.

43. The method of claim 33, wherein the plurality of flat anode layer providing step is preceded by a step of forming the plurality of anode layers to have no holes for registration disposed therethrough.

* * * * *